United States Patent
Mahour et al.

(10) Patent No.: US 11,739,358 B2
(45) Date of Patent: Aug. 29, 2023

(54) ENZYMATIC METHOD FOR PREPARATION OF UDP-GALACTOSE

(71) Applicant: Max-Planck-Gesellschaft zur Förderung der Wissenschaften e.V., Munich (DE)

(72) Inventors: Reza Mahour, Leipzig (DE); Thomas F. T. Rexer, Magdeburg (DE)

(73) Assignee: Max-Planck-Gesellschaft zur Förderung der Wissenschaften e.V., Munich (DE)

( * ) Notice: Subject to any disclaimer, the term of this patent is extended or adjusted under 35 U.S.C. 154(b) by 0 days.

(21) Appl. No.: 17/755,650

(22) PCT Filed: Sep. 30, 2020

(86) PCT No.: PCT/EP2020/077396
§ 371 (c)(1),
(2) Date: May 4, 2022

(87) PCT Pub. No.: WO2021/089251
PCT Pub. Date: May 14, 2021

(65) Prior Publication Data
US 2022/0389469 A1 Dec. 8, 2022

(30) Foreign Application Priority Data
Nov. 5, 2019 (EP) ..................... 19207016

(51) Int. Cl.
*C12P 19/30* (2006.01)
*C12N 9/12* (2006.01)
*C12N 9/10* (2006.01)
*C12N 9/14* (2006.01)
*C12N 11/08* (2020.01)
*C12N 11/087* (2020.01)
*C12P 19/18* (2006.01)
*C12P 21/00* (2006.01)

(52) U.S. Cl.
CPC .......... *C12P 19/305* (2013.01); *C12N 9/1205* (2013.01); *C12N 9/1229* (2013.01); *C12N 9/1241* (2013.01); *C12Y 207/01006* (2013.01); *C12Y 207/04001* (2013.01); *C12Y 207/04014* (2013.01); *C12Y 207/07009* (2013.01)

(58) Field of Classification Search
None
See application file for complete search history.

(56) References Cited

U.S. PATENT DOCUMENTS

2002/0150968 A1   10/2002   Wang et al.

OTHER PUBLICATIONS

Ebrecht et al., "The UDP-glucose pyrophosphorylase from *Giardia lamblia* is redox regulated and exhibits promiscuity to use galactose-1-phosphate" *Biochimica Et Biophysica ACTA* (2015) 1850(1): 88-96.

Mahour et al., "Establishment of a five-enzyme cell-free cascade for the synthesis of uridine diphosphate N-acetylglucosamine" Journal of Biotechnology (2018) 283:120-129.

Muthana et al., "Efficient one-pot multienzyme synthesis of UDP-sugars using a promiscuous UDP-sugar pyrophosphorylase from *Bifidobacterium longum* (BLUSP)" Chemical Communications (2012) 48(21):2728-2730.

International Search Report and Written Opinion dated Jan. 20, 2021 for PCT Application No. PCT/EP2020/077396, filed Sep. 30, 2020.

Datta et al., "Enzyme immobilization: an overview on techniques and support material" Biotech, (2013) 3:1-9.

Koizumi et al., "Large-scale production of UDP-galactose and globotriose by coupling metabolically engineered bacteria" Nature Biotechnology (1998) 16:847-850.

Koszelewski et al., "Immobilization of w-transaminases by encapsulation in a sol-gel/celite matrix" J. Mol. Catalysis B: Enzymatic (2010) 63:39-44.

Kulinich et al., "Human milk oligosaccharides: The role in the fine-tuning of innate immune responses" Carbohydrate Research (2016) 432:62-70.

Li et al. "Simple defined autoinduction medium for high-level recombinant protein production using T7-based *Escherichia coli* expression systems" Applied Microbiology and Biotechnology (2011) 91:1203-1213.

Li et al. "A highly efficient galactokinase from *Bifidobacterium infantis* with broad substrate specificity" Carbohydrate Research (2012) 355:35-39.

Liu et al. "Combined biosynthetic pathway for de novo production of UDP-galactose: catalysis with multiple enzymes immobilized on agarose beads." ChemBioChem (2002) 3:348-355.

Martin et al., "Characterization of free and immobilized (S)-aminotransferase for acetophenone production" Appl. Microbiol. Biotechnol. (2007) 76:843-851.

Mateo et al., "Epoxy Sepabeads: A Novel Epoxy Support for Stabilization of Industrial Enzymes via Very Intense Multipoint Covalent Attachment" Biotechnology Progress (2002) 18: 629-634.

Rexer et al. "One pot synthesis of GDP-mannose by a muiti-enzyme cascade for enzymatic assembly of lipid-linked oligosaccharides." Biotechnology and Bioengineering (2018) 115:192-205.

Warnock et al. "In vitro galactosylation of human IgG at 1 kg scale using recombinant galactosyltransferase" Biotechnology and Bioengineering (2005) 92(7):831-842.

(Continued)

*Primary Examiner* — Suzanne M Noakes
*Assistant Examiner* — Jae W Lee
(74) *Attorney, Agent, or Firm* — Knobbe Martens Olson & Bear LLP

(57) ABSTRACT

The present invention relates to an enzyme-catalyzed process for producing UDP-galactose from low-cost substrates uridine monophosphate and D-galactose in a single reaction mixture. The process can be operated (semi)continuously or in batch mode. The process can be extended to uridine as starting material instead of uridine monophosphate. Further, the process can be adapted to produce galactosylated molecules and biomolecules including saccharides, proteins, peptides, glycoproteins or glycopeptides, particularly human milk oligosaccharides (HMO) and (monoclonal) antibodies.

15 Claims, 17 Drawing Sheets

Specification includes a Sequence Listing.

(56) References Cited

OTHER PUBLICATIONS

Truppo et al., "Development of an Improved Immobilized CAL-B for the Enzymatic Resolution of a Key Intermediate to Odanacatib" Org. Process Res. Dev. (2011) 15:1033-1035.
Yi et al., "Covalent immobilization of ω-transaminase from Vibrio fluvialis JS17 on chitosan beads" Process Biochemistry (2007) 42: 895-898.
Zdarta et al., "A General Overview of Support Materials for Enzyme Immobilization: Characteristics, Properties, Practical Utility" Catalysts (2018) 8:92.

Figure 4
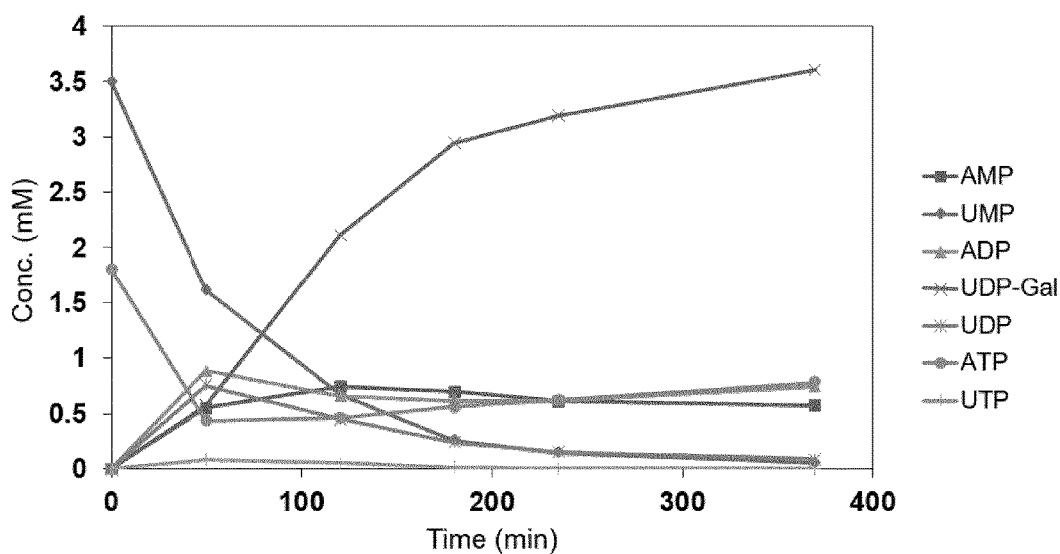
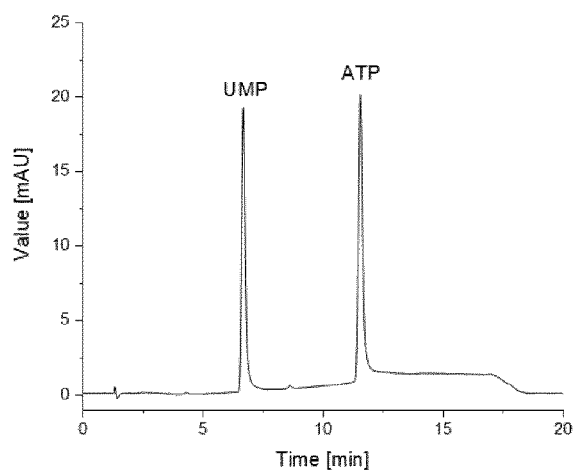
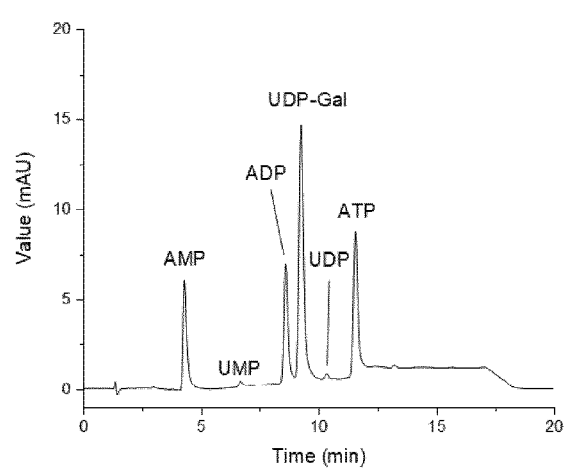

Figure 5
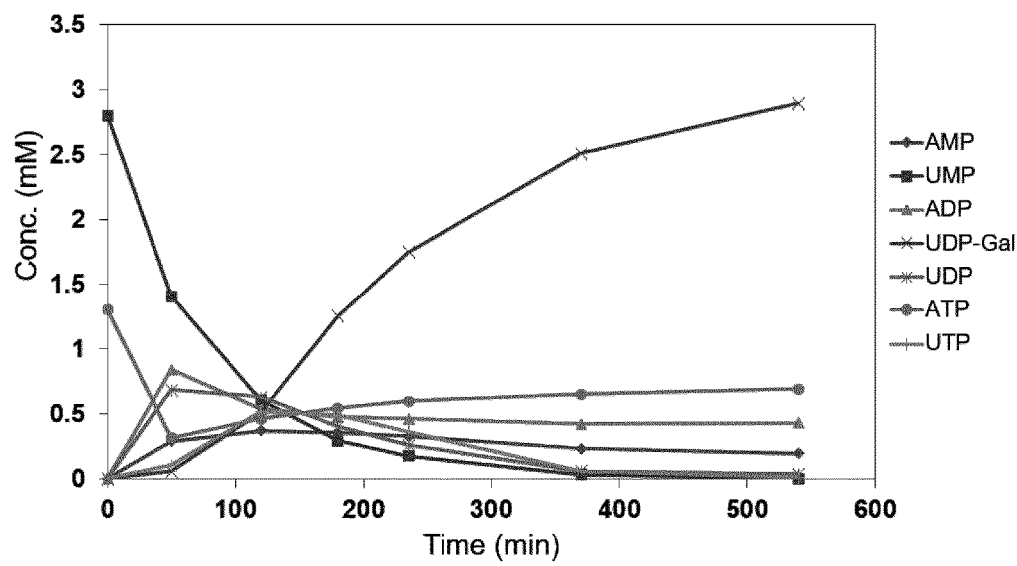
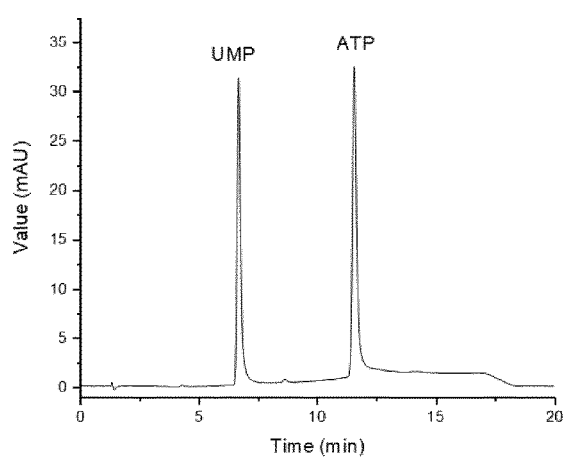
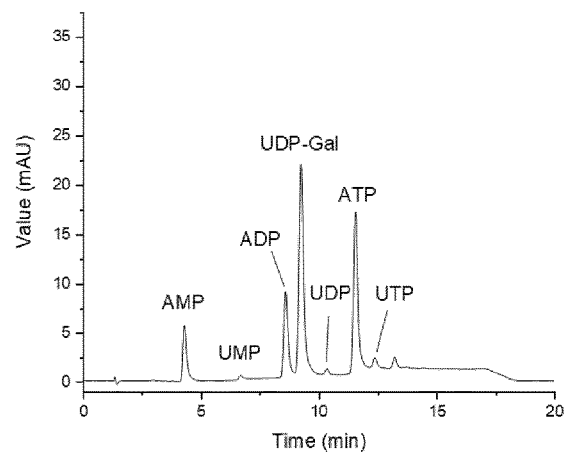

Figure 10
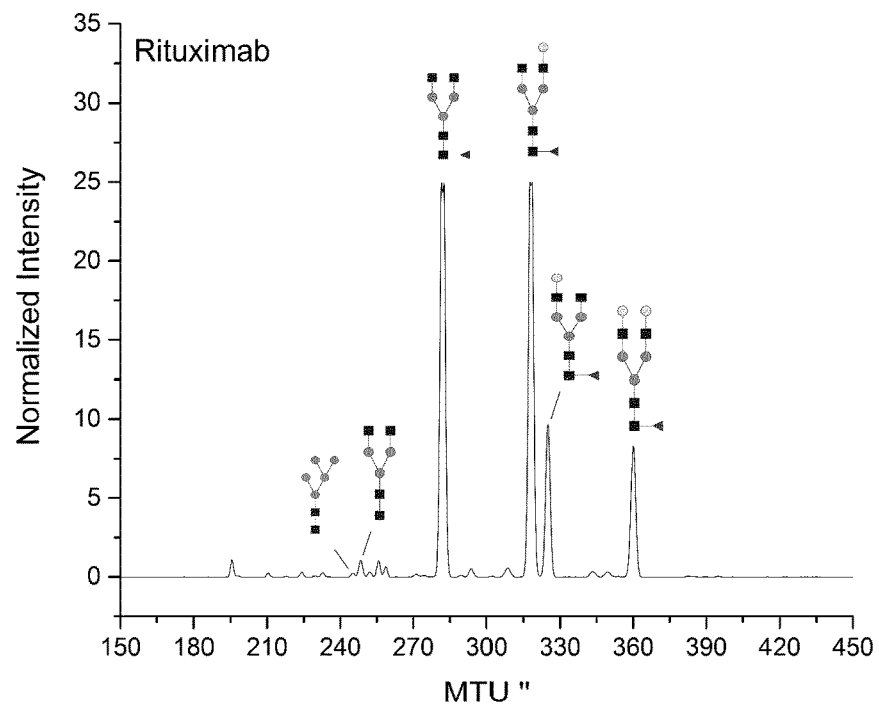
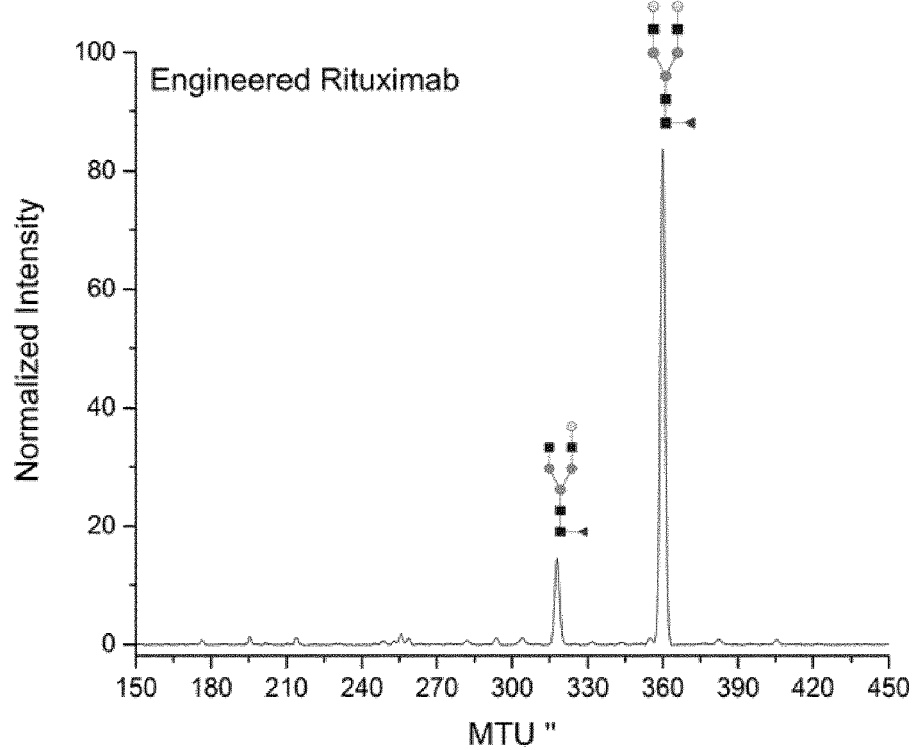

Figure 14

| | Name | Abbreviation | Structure |
|---|---|---|---|
| 1 | Lacto-N-biose | LNB | Galβ1,3GlcNAc |
| 2 | Lacto-N-triose | II | GlcNAcβ1,3Galβ1,4Glc |
| 3 | 3'-Galactosyllactose | 3'GalLac | Galβ1,3Galβ1,4Glc |
| 4 | Lacto-N-tetraose | LNT | Galβ1,3GlcNAcβ1,3Galβ1,4Glc |
| 5 | Lacto-N-neotetraose | LNnT | Galβ1,4GlcNAcβ1,3Galβ1,4Glc |
| 6 | Lacto-N-neohexaose | LNnH | Galβ1,4GlcNAcβ1,3(Galβ1,4GlcNAcβ1,6)Galβ1,4Glc |
| 7 | Lacto-N-hexaose | LNH | Galβ1,3GlcNAcβ1,3(Galβ1,4GlcNAcβ1,6)Galβ1,4Glc |
| 8 | Lacto-N-neooctaose | LNnO | Galβ1,4GlcNAcβ1,3(Galβ1,4GlcNAcβ1,3Galβ1,4GlcNAcβ1,6)Galβ1,4Glc |
| 9 | Lacto-N-neooctaose | LNnO isomer | Galβ1,4GlcNAcβ1,3(Galβ1,4GlcNAcβ1,3Galβ1,4GlcNAcβ1,6)Galβ1,4Glc |
| 10 | para-Lacto-N-neohexaose | p-LNnH | Galβ1,4GlcNAcβ1,3Galβ1,4GlcNAcβ1,3Galβ1,4GlcNAcβ1,3Galβ1,4Glc |
| 11 | Lacto-N-neodecaose | LNnD isomer | Galβ1,4GlcNAcβ1,3(Galβ1,4GlcNAcβ1,3(Galβ1,4GlcNAcβ1,6)Gal-β1,4GlcNAcβ1,3)Galβ1,4Glc |
| 12 | 2'-fucosyllactose | 2'FL | Fucα1,2Galβ1,4Glc |
| 13 | 2',3-Difucosyllactose | 2'3FL or DFL | Fucα1,2Galβ1,4(Fucα1,3)Glc |
| 14 | Lacto-N-fucopentaose I | LNFP I | Fucα1,2Galβ1,3GlcNAcβ1,3Galβ1,4Glc |
| 15 | Lacto-N-fucopentaose II | LNFP II | Galβ1,3(Fucα1,4)GlcNAcβ1,3Galβ1,4Glc |
| 16 | Lacto-N-fuconeopentaose III | LNFP III | Galβ1,4(Fucα1,3)GlcNAcβ1,3Galβ1,4Glc |
| 17 | Lacto-N-difucohexaose I | LNDFH I | Fucα1,2Galβ1,3(Fucα1,4)GlcNAcβ1,3Galβ1,4Glc |
| 18 | F-p-Lacto-N-neohexaose | F-p-LNnH or IFLNH III | Galβ1,4(Fucα1,3)GlcNAcβ1,3Galβ1,4GlcNAcβ1,3 Galβ1,4Glc |
| 19 | F-Lacto-N-neohexaose I | F-LNnH I | Galβ1,4(Fucα1,3)GlcNAcβ1,3Galβ1,4(Fucα1,3)GlcNAcβ1,6)Galβ1,4Glc |
| 20 | F-Lacto-N-neohexaose II | F-LNnH II | Galβ1,4(Fucα1,3)GlcNAcβ1,3(Galβ1,4)GlcNAcβ1,6)Galβ1,4Glc |
| 21 | DF-Lacto-N-neohexaose | DF-LNnH | Galβ1,4(Fucα1,3)GlcNAcβ1,3(Galβ1,4(Fucα1,3)GlcNAcβ1,6)Galβ1,4Glc |
| 22 | α1,2-Fucosylated lacto-N-neohexaose I | 1,2F-LNnH I | Galβ1,4GlcNAcβ1,3(Fucα1,2Galβ1,4GlcNAcβ1,6)Galβ1,4Glc |

Figure 14 continued

| # | Name | Abbrev. | Structure |
|---|---|---|---|
| 23 | α1,2-Difucosylated lacto-N-neohexaose | 1,2DF-LNnH | Fucα1,2Galβ1,4GlcNAcβ1,3(Fucα1,2Galβ1,4GlcNAcβ1,6)Galβ1,4Glc |
| 24 | α1,2-1,3Difucosylated lacto-N-neohexaose I | 1,2-1,3DF-LNnH I | Galβ1,4GlcNAcβ1,3(Fucα1,2Galβ1,4(Fucα1,3)GlcNAcβ1,6)Galβ1,4Glc |
| 25 | α1,2-1,3Difucosylated lacto-N-neohexaose II | 1,2-1,3DF-LNnH II | Fucα1,2Galβ1,4(Fucα1,3)GlcNAcβ1,3(Galβ1,4GlcNAcβ1,6)Galβ1,4Glc |
| 26 | α1,2-1,3Trifucosylated lacto-N-neohexaose I | 1,2-1,3TriF-LNnH I | Galβ1,4(Fucα1,3)GlcNAcβ1,3(Fucα1,2Gal-β1,4(Fucα1,3)GlcNAcβ1,6)Galβ1,4Glc |
| 27 | α1,2-1,3Trifucosylated lacto-N-neohexaose II | 1,2-1,3TriF-LNnH II | Fucα1,2Galβ1,4(Fucα1,3)GlcNAc-β1,3(Galβ1,4(Fucα1,3)GlcNAcβ1,6)Galβ1,4Glc |
| 28 | α1,2-1,3Tetrafucosylated lacto-N-neohexaose | 1,2-1,3TF-LNnH | Fucα1,2Galβ1,4(Fucα1,3)GlcNAcβ1,3(Fucα1,2Gal-β1,4(Fucα1,3)GlcNAcβ1,6)Galβ1,4Glc |
| 29 | 3-Fucosyllactose | 3FL | Galβ1,4Fucα1,3Glc |
| 30 | Lacto-N-neofucopentaose I | LNnFP I | Fucα1,2Galβ1,4GlcNAcβ1,3Galβ1,4Glc |
| 31 | Lacto-N-neofucopentaose V | LNnFP V | Galβ1,4GlcNAcβ1,3Galβ1,4(Fucα1,3)Glc |
| 32 | Lacto-N-neofucopentaose II | LNnFP II | Galβ1,4(Fucα1,3)GlcNAcβ1,3Galβ1,4Glc |
| 33 | Lacto-N-neodifucohexaose II | LNnDFH II | Galβ1,4GlcNAcβ1,3Galβ1,4(Fucα1,3)GlcNAcβ1,3 Galβ1,4(Fucα1,3)Glc |
| 34 | Lacto-N-difucohexaose II | LNDFH II | Galβ1,3(Fucα1,4)GlcNAcβ1,3Galβ1,4(Fucα1,3) Glc |
| 35 | α1,3-fucosylated lacto-N-triose II | | GlcNAcβ1,3Galβ1,4(Fucα1,3)Glc |
| 36 | Difucosylated para-Lacto-N-neohexaose | | Galβ1,4GlcNAcβ1,3Galβ1,4(Fucα1,3)GlcNAcβ1,3Galβ1,4(Fucα1,3)Glc |
| 37 | α2,3-Sialyllactose | 3'SL | NeuAcα2,3Galβ1,4Glc |
| 38 | α2,3-Sialyl-lacto-N-biose | 3'SLNB | NeuAcα2,3Galβ1,3GlcNAc |
| 39 | α2,6-Sialyllactose | 6'SL | NeuAcα2,6Galβ1,4Glc |
| 40 | α2,6-Sialyllacto-N-tetraose | LST a | NeuAcα2,6Galβ1,3GlcNAcβ1,3Galβ1,4Glc |
| 41 | α2,6-Sialyllacto-N-neotetraose | LST c | NeuAcα2,6Galβ1,4GlcNAcβ1,3Galβ1,4Glc |
| 42 | α2,6-Sialyllacto-N-neohexaose | S-LNnH II | NeuAcα2,6Galβ1,4GlcNAcβ1,3(Galβ1,4GlcNAcβ1,6)Galβ1,4Glc |

A

Figure 16 continued
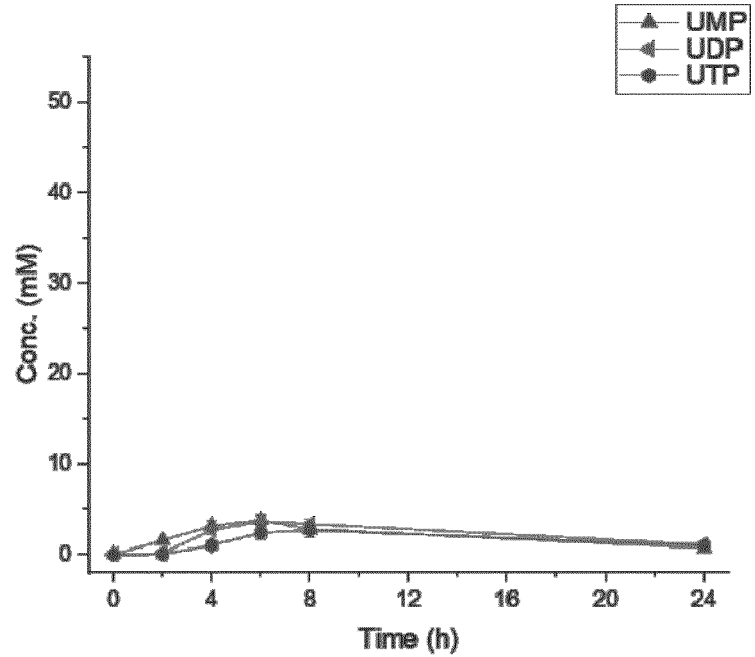
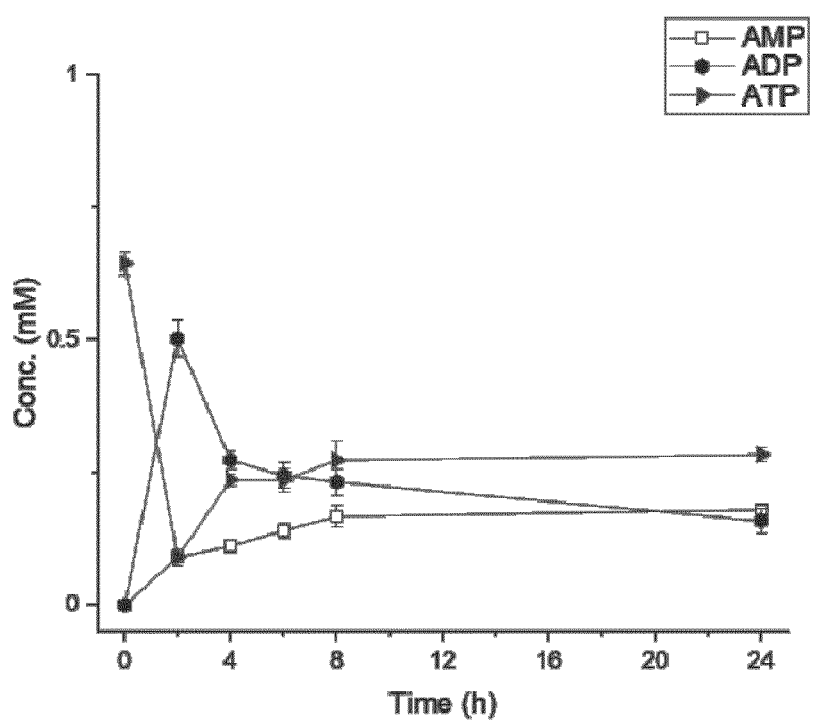

Figure 17
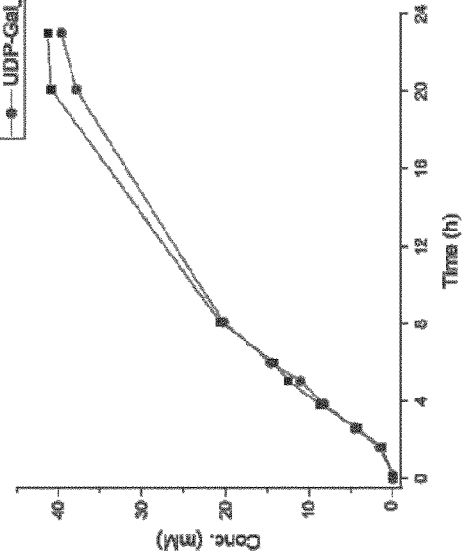
A
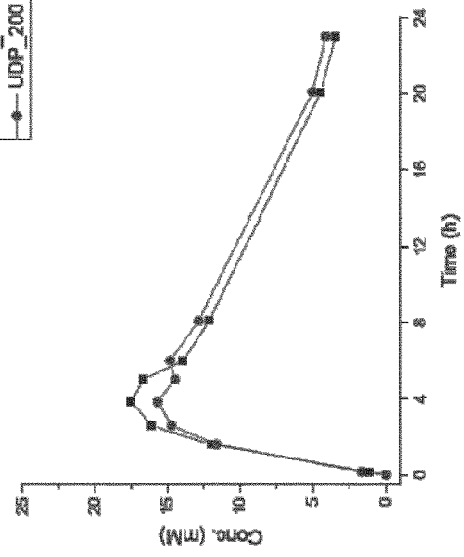
B
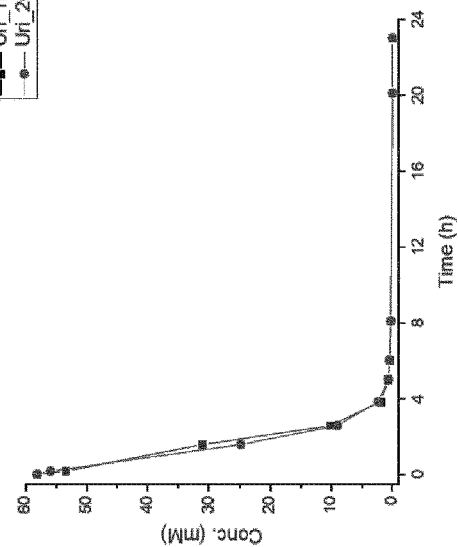
C
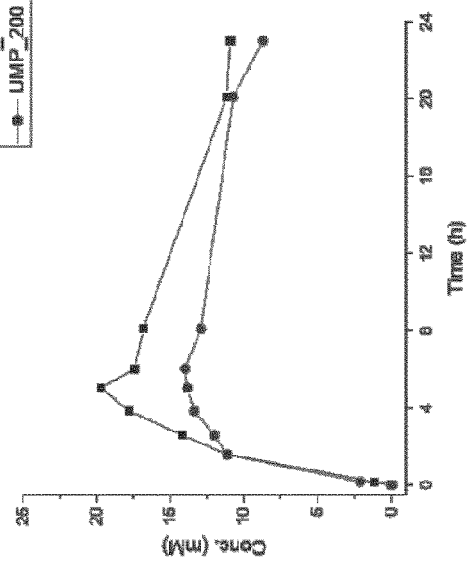
D

Figure 17 continued
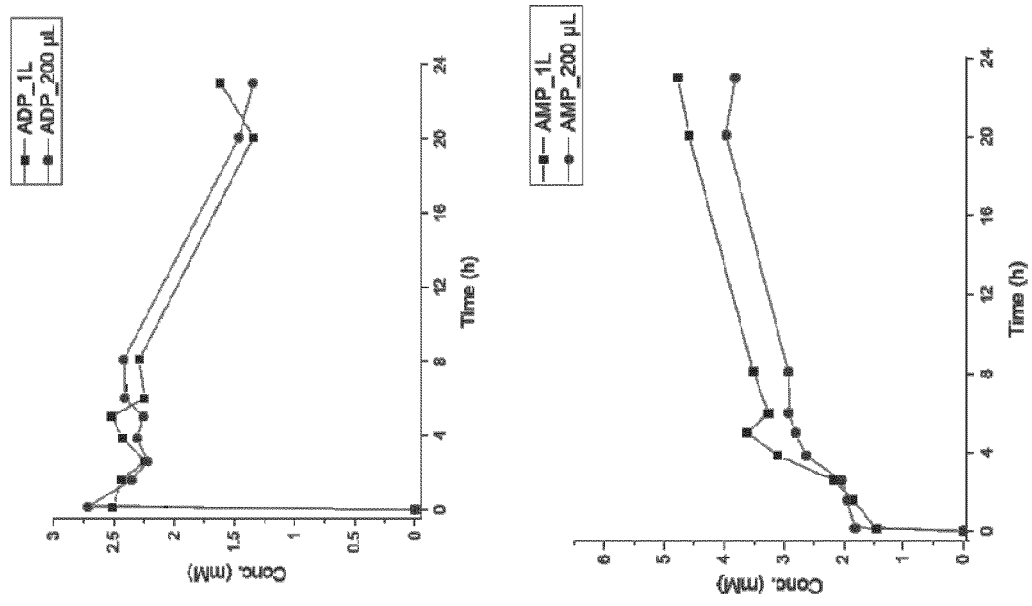
E
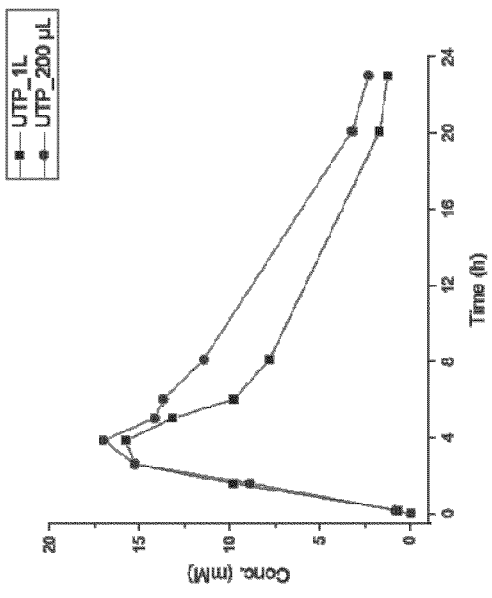
F
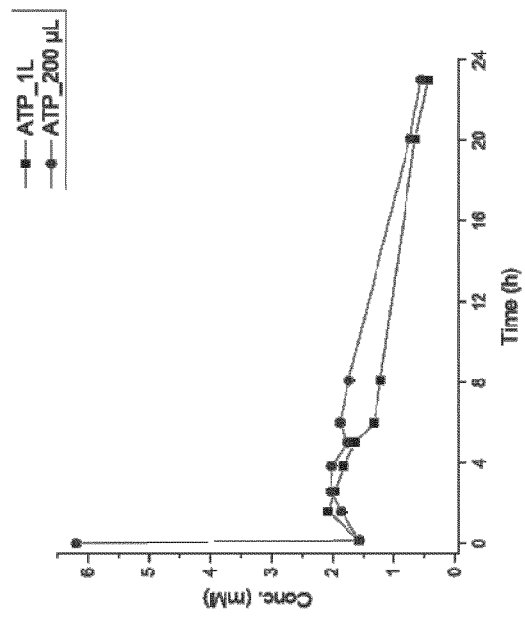
G
H

Figure 18
A
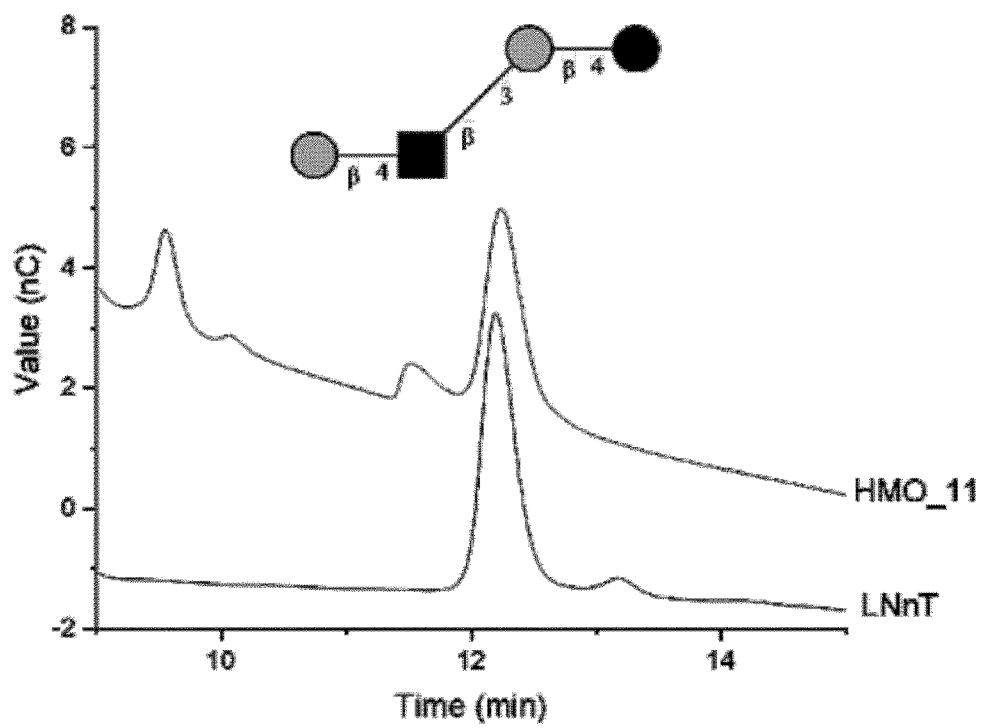
B
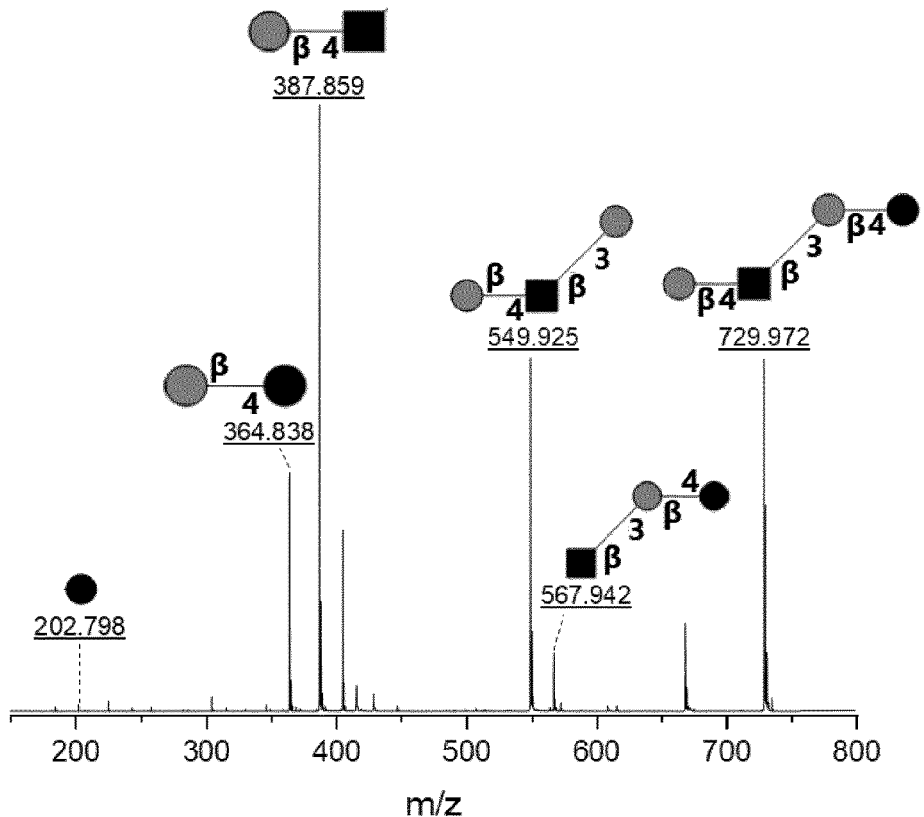

SEQUENCE LISTING

```
<160> NUMBER OF SEQ ID NOS: 9

<210> SEQ ID NO 1
<211> LENGTH: 416
<212> TYPE: PRT
<213> ORGANISM: Bifidobacterium infantis ATCC 15697
<220> FEATURE:
<223> OTHER INFORMATION: galactokinase

<400> SEQUENCE: 1

Met Thr Ala Val Glu Phe Ile Glu Pro Leu Thr His Glu Glu Gly Val
1               5                   10                  15

Ser Gln Ala Thr Lys Leu Phe Val Asp Thr Tyr Gly Ala Ala Pro Glu
            20                  25                  30

Gly Val Trp Ala Ala Pro Gly Arg Val Asn Leu Ile Gly Glu His Thr
        35                  40                  45

Asp Tyr Asn Ala Gly Leu Cys Leu Pro Ile Ala Leu Pro His Arg Thr
    50                  55                  60

Phe Ile Ala Leu Lys Pro Arg Glu Asp Thr Lys Val Arg Val Val Ser
65                  70                  75                  80

Gly Val Ala Pro Asp Lys Val Ala Glu Ala Asp Leu Asp Gly Leu Lys
                85                  90                  95
```

```
Ala Arg Gly Val Asp Gly Trp Ser Ala Tyr Pro Thr Gly Val Ala Trp
            100                 105                 110

Ala Leu Arg Gln Ala Gly Phe Asp Lys Val Lys Gly Phe Asp Ala Ala
            115                 120                 125

Phe Val Ser Cys Val Pro Leu Gly Ser Gly Leu Ser Ser Ala Ala
130                 135                 140

Met Thr Cys Ser Thr Ala Leu Ala Leu Asp Asp Val Tyr Gly Leu Gly
145                 150                 155                 160

Tyr Gly Asp Ser Asp Ala Gly Arg Val Thr Leu Ile Asn Ala Ala Ile
                165                 170                 175

Lys Ser Glu Asn Glu Met Ala Gly Ala Ser Thr Gly Gly Leu Asp Gln
            180                 185                 190

Asn Ala Ser Met Arg Cys Thr Glu Gly His Ala Leu Leu Leu Asp Cys
            195                 200                 205

Arg Pro Glu Leu Thr Pro Leu Glu Asn Val Ser Gln Gln Glu Phe Asp
            210                 215                 220

Leu Asp Lys Tyr Asn Leu Glu Leu Val Val Asp Thr Gln Ala Pro
225                 230                 235                 240

His Gln Leu Asn Asp Gly Gln Tyr Ala Gln Arg Arg Ala Thr Cys Glu
                245                 250                 255

Glu Ala Ala Lys Ile Leu Gly Val Ala Asn Leu Arg Val Thr Ala Asp
            260                 265                 270

Gly Ile Ser Lys Ala Asp Asp Gln Phe Gln Ala Leu Lys Glu Thr Leu
            275                 280                 285

Asp Ala Leu Pro Asp Glu Thr Met Lys Lys Arg Val Arg His Val Val
            290                 295                 300

Thr Glu Ile Glu Arg Val Arg Ser Phe Val Arg Ala Phe Ala Gln Gly
305                 310                 315                 320

Asp Ile Lys Ala Ala Gly Arg Leu Phe Asn Ala Ser His Asp Ser Leu
                325                 330                 335

Ala Ala Asp Tyr Glu Val Thr Val Pro Glu Leu Asp Ile Ala Val Asp
            340                 345                 350

Val Ala Arg Lys Asn Gly Ala Tyr Gly Ala Arg Met Thr Gly Gly Gly
            355                 360                 365

Phe Gly Gly Ser Ile Ile Ala Leu Val Asp Lys Gly Gln Gly His Glu
370                 375                 380

Ile Ala Gln Lys Ile Ala Asp Arg Phe Glu Lys Glu Gly Phe Asn Ala
385                 390                 395                 400

Pro Arg Ala Leu Pro Ala Phe Ala Ala Ser Ala Ser Arg Glu Ala
                405                 410                 415

<210> SEQ ID NO 2
<211> LENGTH: 202
<212> TYPE: PRT
<213> ORGANISM: Arabidopsis thaliana
<220> FEATURE:
<223> OTHER INFORMATION: uridine monophosphate kinase

<400> SEQUENCE: 2

Met Gly Ser Val Asp Ala Ala Asn Gly Ser Gly Lys Lys Pro Thr Val
1               5                   10                  15

Ile Phe Val Leu Gly Gly Pro Gly Ser Gly Lys Gly Thr Gln Cys Ala
            20                  25                  30

Tyr Ile Val Glu His Tyr Gly Tyr Thr His Leu Ser Ala Gly Asp Leu
        35                  40                  45
```

```
Leu Arg Ala Glu Ile Lys Ser Gly Ser Glu Asn Gly Thr Met Ile Gln
     50                  55                  60

Asn Met Ile Lys Glu Gly Lys Ile Val Pro Ser Glu Val Thr Ile Lys
 65                  70                  75                  80

Leu Leu Gln Lys Ala Ile Gln Glu Asn Gly Asn Asp Lys Phe Leu Ile
                 85                  90                  95

Asp Gly Phe Pro Arg Asn Glu Asn Arg Ala Ala Phe Glu Lys Val
                100                 105                 110

Thr Glu Ile Glu Pro Lys Phe Val Leu Phe Asp Cys Pro Glu Glu
            115                 120                 125

Glu Met Glu Lys Arg Leu Leu Gly Arg Asn Gln Gly Arg Glu Asp Asp
            130                 135                 140

Asn Ile Glu Thr Ile Arg Lys Arg Phe Lys Val Phe Leu Glu Ser Ser
145                 150                 155                 160

Leu Pro Val Ile His Tyr Tyr Glu Ala Lys Gly Lys Val Arg Lys Ile
                165                 170                 175

Asn Ala Ala Lys Pro Ile Glu Ala Val Phe Glu Glu Val Lys Ala Ile
                180                 185                 190

Phe Ser Pro Glu Ala Glu Lys Val Glu Ala
            195                 200

<210> SEQ ID NO 3
<211> LENGTH: 301
<212> TYPE: PRT
<213> ORGANISM: Ruegeria pomeroyi
<220> FEATURE:
<223> OTHER INFORMATION: polyphosphate kinase 3

<400> SEQUENCE: 3

Met Asn Arg Asn Gly Ser Thr Lys Asp Pro Arg Arg Met Thr Gly Ala
  1               5                  10                  15

Ala Thr Gly Glu Ile Ser Arg Tyr Phe Asn Asp Lys Ala Pro Lys Asp
                 20                  25                  30

Ile Arg Arg Ala Ile Glu Lys Ala Asp Lys Asp Ile Leu Ser Thr
             35                  40                  45

Thr Tyr Pro Tyr Asp Ala Glu Met Thr Ala Lys Asp Tyr Arg Ala Gln
 50                  55                  60

Met Glu Ala Leu Gln Ile Glu Leu Val Lys Leu Gln Ala Trp Ile Lys
 65                  70                  75                  80

Gln Ser Gly Ala Arg Val Ala Leu Leu Phe Glu Gly Arg Asp Ala Ala
                 85                  90                  95

Gly Lys Gly Gly Thr Ile Lys Arg Phe Arg Glu Asn Leu Asn Pro Arg
                100                 105                 110

Gly Ala Arg Val Val Ala Leu Ser Lys Pro Thr Glu Ala Glu Arg Ser
            115                 120                 125

Gln Trp Tyr Phe Gln Arg Tyr Ile Gln His Leu Pro Ser Ala Gly Glu
            130                 135                 140

Leu Val Phe Tyr Asp Arg Ser Trp Tyr Asn Arg Gly Val Val Glu His
145                 150                 155                 160

Val Phe Gly Trp Cys Asp Glu Glu Gln Arg Glu Arg Phe Phe Arg Gln
                165                 170                 175

Val Met Pro Phe Glu His Asp Leu Val Asp Asp Gly Ile His Leu Phe
                180                 185                 190

Lys Phe Trp Leu Asn Val Gly Arg Ala Glu Gln Leu Arg Arg Phe His
                195                 200                 205
```

```
Asp Arg Glu Arg Asp Pro Leu Lys Gln Trp Lys Leu Ser Pro Val Asp
        210                 215                 220
Ile Ala Gly Leu Asp Lys Trp Glu Ala Tyr Thr Thr Ala Ile Ser Gln
225                 230                 235                 240
Thr Leu Thr Arg Ser His Ser Asp Arg Ala Pro Trp Thr Val Ile Arg
                245                 250                 255
Ser Asp Lys Lys Arg Ala Arg Leu Ala Ala Ile Arg Thr Val Leu
            260                 265                 270
Ser Gly Ile Asp Tyr Asp Asn Lys Asp Arg Ala Ala Val Gly Gln Pro
        275                 280                 285
Asp Ala Ala Ile Cys Gly Gly Pro Asp Ile Trp Asp Ala
290                 295                 300
```

<210> SEQ ID NO 4
<211> LENGTH: 302
<212> TYPE: PRT
<213> ORGANISM: E. coli K-12 MG1655
<220> FEATURE:
<223> OTHER INFORMATION: glucose 1-phosphate uridylyltransferase

<400> SEQUENCE: 4

```
Met Ala Ala Ile Asn Thr Lys Val Lys Lys Ala Val Ile Pro Val Ala
1               5                   10                  15
Gly Leu Gly Thr Arg Met Leu Pro Ala Thr Lys Ala Ile Pro Lys Glu
            20                  25                  30
Met Leu Pro Leu Val Asp Lys Pro Leu Ile Gln Tyr Val Val Asn Glu
        35                  40                  45
Cys Ile Ala Ala Gly Ile Thr Glu Ile Val Leu Val Thr His Ser Ser
    50                  55                  60
Lys Asn Ser Ile Glu Asn His Phe Asp Thr Ser Phe Glu Leu Glu Ala
65                  70                  75                  80
Met Leu Glu Lys Arg Val Lys Arg Gln Leu Leu Asp Glu Val Gln Ser
                85                  90                  95
Ile Cys Pro Pro His Val Thr Ile Met Gln Val Arg Gln Gly Leu Ala
            100                 105                 110
Lys Gly Leu Gly His Ala Val Leu Cys Ala His Pro Val Val Gly Asp
        115                 120                 125
Glu Pro Val Ala Val Ile Leu Pro Asp Val Ile Leu Asp Glu Tyr Glu
    130                 135                 140
Ser Asp Leu Ser Gln Asp Asn Leu Ala Glu Met Ile Arg Arg Phe Asp
145                 150                 155                 160
Glu Thr Gly His Ser Gln Ile Met Val Glu Pro Val Ala Asp Val Thr
                165                 170                 175
Ala Tyr Gly Val Val Asp Cys Lys Gly Val Glu Leu Ala Pro Gly Glu
            180                 185                 190
Ser Val Pro Met Val Gly Val Val Glu Lys Pro Lys Ala Asp Val Ala
        195                 200                 205
Pro Ser Asn Leu Ala Ile Val Gly Arg Tyr Val Leu Ser Ala Asp Ile
    210                 215                 220
Trp Pro Leu Leu Ala Lys Thr Pro Pro Gly Ala Gly Asp Glu Ile Gln
225                 230                 235                 240
Leu Thr Asp Ala Ile Asp Met Leu Ile Glu Lys Glu Thr Val Glu Ala
                245                 250                 255
Tyr His Met Lys Gly Lys Ser His Asp Cys Gly Asn Lys Leu Gly Tyr
            260                 265                 270
```

Met Gln Ala Phe Val Glu Tyr Gly Ile Arg His Asn Thr Leu Gly Thr
            275                 280                 285

Glu Phe Lys Ala Trp Leu Glu Glu Met Gly Ile Lys Lys
    290                 295                 300

<210> SEQ ID NO 5
<211> LENGTH: 175
<212> TYPE: PRT
<213> ORGANISM: Pasteurella multocida subsp. multocida str. Pm70
<220> FEATURE:
<223> OTHER INFORMATION: inorganic diphosphatase

<400> SEQUENCE: 5

Met Gly Leu Glu Thr Val Pro Ala Gly Lys Ala Leu Pro Asp Asp Ile
1               5                   10                  15

Tyr Val Val Ile Glu Ile Pro Ala Asn Ser Asp Pro Ile Lys Tyr Glu
            20                  25                  30

Val Asp Lys Glu Ser Gly Ala Leu Phe Val Asp Arg Phe Met Ala Thr
        35                  40                  45

Ala Met Phe Tyr Pro Ala Asn Tyr Gly Tyr Val Asn Asn Thr Leu Ser
    50                  55                  60

Leu Asp Gly Asp Pro Val Asp Val Leu Val Pro Thr Pro Tyr Pro Leu
65                  70                  75                  80

Gln Pro Gly Ser Val Ile Arg Cys Arg Pro Val Gly Val Leu Lys Met
                85                  90                  95

Thr Asp Glu Ala Gly Ser Asp Ala Lys Val Val Ala Val Pro His Ser
            100                 105                 110

Lys Leu Thr Lys Glu Tyr Asp His Ile Lys Asp Val Asn Asp Leu Pro
        115                 120                 125

Ala Leu Leu Lys Ala Gln Ile Gln His Phe Phe Glu Ser Tyr Lys Ala
    130                 135                 140

Leu Glu Ala Gly Lys Trp Val Lys Val Asp Gly Trp Glu Gly Val Asp
145                 150                 155                 160

Ala Ala Arg Gln Glu Ile Leu Asp Ser Phe Glu Arg Ala Lys Lys
                165                 170                 175

<210> SEQ ID NO 6
<211> LENGTH: 304
<212> TYPE: PRT
<213> ORGANISM: Pseudomonas aeruginosa
<220> FEATURE:
<223> OTHER INFORMATION: 1-domain polyphosphate kinase 2

<400> SEQUENCE: 6

Met Asp Ser Tyr Gly Asp Thr Ser Gly Arg Ile Gly Arg Asp Trp Leu
1               5                   10                  15

Asp Arg His Asp Glu Glu Leu Glu Gln Glu Leu Leu Asp Asp Glu Leu
            20                  25                  30

Asn Leu Asp Glu Leu Phe Gly Pro Glu Gln Glu Asp Ala Pro Gly Glu
        35                  40                  45

Leu Ser Arg Arg Arg Tyr Phe Arg Glu Leu Phe Arg Leu Gln Arg Glu
    50                  55                  60

Leu Val Lys Leu Gln Asn Trp Val Val His Thr Gly His Lys Val Val
65                  70                  75                  80

Ile Leu Phe Glu Gly Arg Asp Ala Ala Gly Lys Gly Gly Val Ile Lys
                85                  90                  95

Arg Ile Thr Gln Arg Leu Asn Pro Arg Val Cys Arg Val Ala Ala Leu

```
                100             105             110
Pro Ala Pro Asn Asp Arg Glu Gln Thr Gln Trp Tyr Phe Gln Arg Tyr
            115             120             125

Val Ser His Leu Pro Ala Gly Gly Glu Ile Val Leu Phe Asp Arg Ser
    130             135             140

Trp Tyr Asn Arg Ala Gly Val Glu Arg Val Met Gly Phe Cys Asn Asp
145             150             155             160

Glu Gln Tyr Glu Glu Phe Phe Arg Ser Val Pro Glu Phe Glu Lys Met
                165             170             175

Leu Ala Arg Ser Gly Ile Gln Leu Leu Lys Tyr Trp Phe Ser Ile Ser
            180             185             190

Asp Ala Glu Gln His Leu Arg Phe Leu Ser Arg Ile His Asp Pro Leu
        195             200             205

Lys Gln Trp Lys Leu Ser Pro Met Asp Leu Glu Ser Arg Arg Arg Trp
    210             215             220

Glu Ala Tyr Thr Lys Ala Lys Glu Thr Met Leu Glu Arg Thr His Ile
225             230             235             240

Pro Glu Ala Pro Trp Trp Val Val Gln Ala Asp Asp Lys Lys Arg Ala
                245             250             255

Arg Leu Asn Cys Ile His His Leu Leu Gln Gln Met Pro Tyr Arg Glu
            260             265             270

Val Pro Gln Pro Pro Val His Leu Pro Glu Arg Leu Arg His Ala Asp
        275             280             285

Tyr Val Arg His Pro Thr Pro Gly Glu Ile Ile Val Pro Glu Val Tyr
    290             295             300

<210> SEQ ID NO 7
<211> LENGTH: 496
<212> TYPE: PRT
<213> ORGANISM: Pseudomonas aeruginosa
<220> FEATURE:
<223> OTHER INFORMATION: 2-domain polyphosphate kinase 2

<400> SEQUENCE: 7

Met Phe Glu Ser Ala Glu Val Gly His Ser Ile Asp Lys Asp Thr Tyr
1               5               10              15

Glu Lys Ala Val Ile Glu Leu Arg Glu Ala Leu Leu Glu Ala Gln Phe
            20              25              30

Glu Leu Lys Gln Gln Ala Arg Phe Pro Val Ile Ile Leu Ile Asn Gly
        35              40              45

Ile Glu Gly Ala Gly Lys Gly Glu Thr Val Lys Leu Leu Asn Glu Trp
    50              55              60

Met Asp Pro Arg Leu Ile Glu Val Gln Ser Phe Leu Arg Pro Ser Asp
65              70              75              80

Glu Glu Leu Glu Arg Pro Pro Gln Trp Arg Phe Trp Arg Arg Leu Pro
                85              90              95

Pro Lys Gly Arg Thr Gly Ile Phe Phe Gly Asn Trp Tyr Ser Gln Met
            100             105             110

Leu Tyr Ala Arg Val Glu Gly His Ile Lys Glu Ala Lys Leu Asp Gln
        115             120             125

Ala Ile Asp Ala Ala Glu Arg Phe Glu Arg Met Leu Cys Asp Glu Gly
    130             135             140

Ala Leu Leu Phe Lys Phe Trp Phe His Leu Ser Lys Lys Gln Leu Lys
145             150             155             160

Glu Arg Leu Lys Ala Leu Glu Lys Asp Pro Gln His Ser Trp Lys Leu
```

```
            165                 170                 175
Ser Pro Leu Asp Trp Lys Gln Ser Glu Val Tyr Asp Arg Phe Val His
            180                 185                 190

Tyr Gly Glu Arg Val Leu Arg Arg Thr Ser Arg Asp Tyr Ala Pro Trp
            195                 200                 205

Tyr Val Val Glu Gly Ala Asp Glu Arg Tyr Arg Ala Leu Thr Val Gly
            210                 215                 220

Arg Ile Leu Leu Glu Gly Leu Gln Ala Ala Leu Ala Thr Lys Glu Arg
225                 230                 235                 240

Ala Lys Arg Gln Pro His Ala Ala Pro Leu Val Ser Ser Leu Asp Asn
            245                 250                 255

Arg Gly Leu Leu Asp Ser Leu Asp Leu Gly Gln Tyr Leu Asp Lys Asp
            260                 265                 270

Ala Tyr Lys Glu Gln Leu Ala Ala Glu Gln Ala Arg Leu Ala Gly Leu
            275                 280                 285

Ile Arg Asp Lys Arg Phe Arg Gln His Ser Leu Val Ala Val Phe Glu
            290                 295                 300

Gly Asn Asp Ala Ala Gly Lys Gly Gly Ala Ile Arg Arg Val Thr Asp
305                 310                 315                 320

Ala Leu Asp Pro Arg Gln Tyr His Ile Val Pro Ile Ala Ala Pro Thr
            325                 330                 335

Glu Glu Glu Arg Ala Gln Pro Tyr Leu Trp Arg Phe Trp Arg His Ile
            340                 345                 350

Pro Ala Arg Arg Gln Phe Thr Ile Phe Asp Arg Ser Trp Tyr Gly Arg
            355                 360                 365

Val Leu Val Glu Arg Ile Glu Gly Phe Cys Ala Pro Ala Asp Trp Leu
            370                 375                 380

Arg Ala Tyr Gly Glu Ile Asn Asp Phe Glu Glu Gln Leu Ser Glu Tyr
385                 390                 395                 400

Gly Ile Ile Val Val Lys Phe Trp Leu Ala Ile Asp Lys Gln Thr Gln
            405                 410                 415

Met Glu Arg Phe Lys Glu Arg Glu Lys Thr Pro Tyr Lys Arg Tyr Lys
            420                 425                 430

Ile Thr Glu Glu Asp Trp Arg Asn Arg Asp Lys Trp Asp Gln Tyr Val
            435                 440                 445

Asp Ala Val Gly Asp Met Val Asp Arg Thr Ser Thr Glu Ile Ala Pro
450                 455                 460

Trp Thr Leu Val Glu Ala Asn Asp Lys Arg Phe Ala Arg Val Lys Val
465                 470                 475                 480

Leu Arg Thr Ile Asn Asp Ala Ile Glu Ala Ala Tyr Lys Lys Asp Lys
            485                 490                 495

<210> SEQ ID NO 8
<211> LENGTH: 416
<212> TYPE: PRT
<213> ORGANISM: Bifidobacterium longum
<220> FEATURE:
<223> OTHER INFORMATION: galactokinase

<400> SEQUENCE: 8

Met Thr Ala Val Glu Phe Ile Glu Pro Leu Thr His Glu Glu Gly Val
1               5                   10                  15

Ser Gln Ala Thr Lys Leu Phe Val Asp Thr Tyr Gly Ala Ala Pro Glu
            20                  25                  30

Gly Val Trp Ala Ala Pro Gly Arg Val Asn Leu Ile Gly Glu His Thr
```

```
                35                  40                  45
Asp Tyr Asn Ala Gly Leu Cys Leu Pro Ile Ala Leu Pro His Arg Thr
 50                  55                  60

Phe Ile Ala Leu Lys Pro Arg Glu Asp Thr Lys Val Arg Val Val Ser
 65                  70                  75                  80

Asp Val Ala Pro Asp Lys Val Ala Glu Ala Asp Leu Asp Gly Leu Lys
                 85                  90                  95

Ala Arg Gly Val Asp Gly Trp Ser Ala Tyr Pro Thr Gly Val Ala Trp
                100                 105                 110

Ala Leu Arg Gln Ala Gly Phe Asp Lys Val Lys Gly Phe Asp Ala Ala
                115                 120                 125

Phe Val Ser Cys Val Pro Leu Gly Ser Gly Leu Ser Ser Ala Ala
                130                 135                 140

Met Thr Cys Ser Thr Ala Leu Ala Leu Asp Asp Val Tyr Gly Leu Gly
145                 150                 155                 160

Tyr Gly Asp Ser Asp Ala Gly Arg Val Thr Leu Ile Asn Ala Ala Ile
                165                 170                 175

Lys Ser Glu Asn Glu Met Ala Gly Ala Ser Thr Gly Gly Leu Asp Gln
                180                 185                 190

Asn Ala Ser Met Arg Cys Thr Ala Gly His Ala Leu Leu Leu Asp Cys
                195                 200                 205

Arg Pro Glu Leu Thr Pro Leu Glu Asn Val Ser Gln Gln Glu Phe Asp
                210                 215                 220

Leu Asp Lys Tyr Asn Leu Glu Leu Leu Val Val Asp Thr Gln Ala Pro
225                 230                 235                 240

His Gln Leu Asn Asp Gly Gln Tyr Ala Gln Arg Arg Ala Thr Cys Glu
                245                 250                 255

Glu Ala Ala Lys Ile Leu Gly Val Ala Asn Leu Arg Val Thr Ala Asp
                260                 265                 270

Gly Ile Ser Lys Ala Asp Asp Gln Phe Gln Ala Leu Lys Glu Thr Leu
                275                 280                 285

Asp Ala Leu Pro Asp Glu Thr Met Lys Lys Arg Val Arg His Val Val
                290                 295                 300

Thr Glu Ile Glu Arg Val Arg Ser Phe Val Arg Ala Phe Ala Gln Gly
305                 310                 315                 320

Asp Ile Lys Ala Ala Gly Arg Leu Phe Asn Ala Ser His Asp Ser Leu
                325                 330                 335

Ala Ala Asp Tyr Glu Val Thr Val Pro Glu Leu Asp Ile Ala Val Asp
                340                 345                 350

Val Ala Arg Lys Asn Gly Ala Tyr Gly Ala Arg Met Thr Gly Gly Gly
                355                 360                 365

Phe Gly Gly Ser Ile Ile Ala Leu Val Asp Lys Gly Arg Ser Gln Glu
                370                 375                 380

Val Ala Gln Lys Ile Ala Asp Glu Phe Glu Lys Gln Gly Phe His Ala
385                 390                 395                 400

Pro Arg Ala Leu Ala Ala Tyr Ala Ala Pro Ser Ala Ser Arg Glu Ala
                405                 410                 415
```

```
<210> SEQ ID NO 9
<211> LENGTH: 213
<212> TYPE: PRT
<213> ORGANISM: Escherichia coli K-12
<220> FEATURE:
<223> OTHER INFORMATION: uridine/cytidine kinase

<400> SEQUENCE: 9

Met Thr Asp Gln Ser His Gln Cys Val Ile Ile Gly Ile Ala Gly Ala
1               5                   10                  15

Ser Ala Ser Gly Lys Ser Leu Ile Ala Ser Thr Leu Tyr Arg Glu Leu
            20                  25                  30

Arg Glu Gln Val Gly Asp Glu His Ile Gly Val Ile Pro Glu Asp Cys
        35                  40                  45

Tyr Tyr Lys Asp Gln Ser His Leu Ser Met Glu Glu Arg Val Lys Thr
    50                  55                  60

Asn Tyr Asp His Pro Ser Ala Met Asp His Ser Leu Leu Leu Glu His
65                  70                  75                  80

Leu Gln Ala Leu Lys Arg Gly Ser Ala Ile Asp Leu Pro Val Tyr Ser
                85                  90                  95

Tyr Val Glu His Thr Arg Met Lys Glu Thr Val Thr Val Glu Pro Lys
            100                 105                 110

Lys Val Ile Ile Leu Glu Gly Ile Leu Leu Leu Thr Asp Ala Arg Leu
        115                 120                 125

Arg Asp Glu Leu Asn Phe Ser Ile Phe Val Asp Thr Pro Leu Asp Ile
    130                 135                 140

Cys Leu Met Arg Arg Ile Lys Arg Asp Val Asn Glu Arg Gly Arg Ser
145                 150                 155                 160

Met Asp Ser Val Met Ala Gln Tyr Gln Lys Thr Val Arg Pro Met Phe
                165                 170                 175

Leu Gln Phe Ile Glu Pro Ser Lys Gln Tyr Ala Asp Ile Ile Val Pro
            180                 185                 190

Arg Gly Gly Lys Asn Arg Ile Ala Ile Asp Ile Leu Lys Ala Lys Ile
        195                 200                 205

Ser Gln Phe Phe Glu
    210
```

US 11,739,358 B2

ENZYMATIC METHOD FOR PREPARATION OF UDP-GALACTOSE

The present application is the national phase entry of PCT Application No. PCT/EP2020/077396, filed Sep. 30, 2020, which claims priority to EP Application No. 19207016.7, filed Nov. 5, 2019, both of which are incorporated by reference in their entireties.

REFERENCE TO SEQUENCE LISTING

The present application is filed with a Sequence Listing in Electronic format. The Sequence Listing is provided as a file entitled ABK001022APC.txt, created Apr. 20, 2022, which is approximately 25 kb in size. The information in the electronic format of the sequence listing is incorporated herein by reference in its entirety.

FIELD OF THE INVENTION

The present invention relates to an enzyme-catalyzed process for producing UDP-galactose from low-cost substrates uridine monophosphate and D-galactose in a single reaction mixture. Said process can be operated (semi)continuously, in batch or fed-batch mode or any other mode of operation. Further, said process can be adapted to produce galactosylated molecules and biomolecules including saccharides, particularly human milk oligosaccharides (HMO), proteins, glycoproteins, particularly antibodies, glycopeptides, and bioconjugates, particularly carbohydrate conjugate vaccines and antibody-drug conjugates.

BACKGROUND OF THE INVENTION

Uridine 5'-diphospho-α-D-galactose (UDP-galactose or UDP-Gal) is a key substrate for a large number of biotechnological applications and food technology. It is the substrate for the galactosylation of therapeutic antibodies which are used to treat autoimmune diseases. Moreover, UDP-galactose is needed for the production of carbohydrate vaccines and in the growing field of personalized medicine, i.e. preparation of glyconanomaterials for drug delivery. In infant food (human milk), galactosylated oligosaccharides comprise an important component of human milk oligosaccharides and, thus, there is a high demand to include galactosylated sugars in synthetically produced dairy products for infants (Carbohydrate Research 432 (2016) 62-70).

However, in spite of the high demand for UDP-galactose (in the order of tons per year), the availability of UDP-galactose is very limited, even for researchers. Up to now, the price of UDP-galactose is about 2,000 USD per gram. Due to the high price of UDP-galactose not only basic and applied research activities are hampered but also industrial applications are hindered.

Bioprocess engineering strategies to synthesize UDP-galactose can be classified into in vivo and in vitro processes: Microorganisms are metabolically engineered in order to produce UDP-galactose, either intracellulary or extracellularly, as part of their metabolism. However, low yields, high levels of unwanted by-products, the required time for cell line design and the complicated scale up are drawbacks. Taking into account regulatory aspects, specifically for infant food, application of genetically modified organisms (GMOs) can severely delay the approval process.

U.S. patent application Ser. No. 09/757,846 and Liu et al. (ChemBioChem, 2002, 3, 348-355) disclose methods for in vitro production of glycoconjugates using sugar nucleotide producing enzymes and a glycosyltransferase. UDP-Gal was prepared by a 7 enzyme cascade starting from expensive glucose 1-phosphate and UDP-glucose in an overall yield of 35%. The enzymes are immobilized on Ni NTA agarose beads, which are impractical for larger scale synthesis. The enzymes are weakly bound on the agarose beads and rapidly washed off in reaction mixtures of high ionic strength which are necessary for an optimal UDP-Gal production. Leaching of enzymes can severely hamper validation processes, specifically for food and pharma applications and makes it necessary to recharge the beads after each use. Further, nickel ions, which are toxic in large amounts, are released from the beads to the solution; thereby making their use in the synthesis of HMOS most likely impossible. In addition, Ni agarose beads are not mechanically robust; due to their softness they cannot be used in stirred tank reactors since the high shear rates cause agarose beads to degrade, or in large scale column packing due to compression. The release of galactose from degraded agarose beads may cause substrate poisoning of enzymes.

Koizumo et al. (Nature Biotech. 1998, 16, 847) report on a similar UDP-Gal synthesis which uses glucose 1-phosphate in addition to galactose and orotic acid as starting material. Transfer of UTP to galactose was achieved with two enzymes GalT and GalU. The process was performed in presence of 10% (v/v) xylene and a low reaction yield of 29% from galactose was achieved after 21 hours. High concentrations of biomass were used which hampers the large scale application due to significant mass transfer limitations. Moreover, xylene is of modest acute toxicity.

Muthana et al. (Chem. Commun., 2012, 48, 2728-2730) report on a one-pot multienzyme synthesis of UDP-sugars from monosaccharides and UTP using a promiscuous UDP-sugar pyrophosphorylase (USP, EC 2.7.7.64) from *Bifidobacterium longum* (BLUSP).

There is a long-felt need for a method of producing UDP-galactose in a cost-effective manner starting from low cost and readily available substrates.

Thus, it is the objective of the present invention to provide a cost-effective and efficient method for the preparation of UDP-galactose.

The objective of the present invention is solved by the teaching of the independent claims. Further advantageous features, aspects and details of the invention are evident from the dependent claims, the description, the figures, and the examples of the present application.

DESCRIPTION OF THE INVENTION

In biochemistry nucleotide sugars are well known as active forms of monosaccharides and in glycosylation reactions nucleotide sugars are known to act as glycosyl donors. Glycosyltransferases (GTFs) are enzymes that catalyze the transfer of saccharide moieties from activated nucleotide sugars to nucleophilic glycosyl acceptor molecules. Thus, in biochemistry the glycosylation reactions are catalyzed by glycosyltransferases.

In order to act as glycosyl donors it is essential that the respective monosaccharides are present in a highly energetic form, like for example in form of nucleotide sugars, particularly nucleotide diphospho sugars derived from uridine diphosphate, guanosine diphosphate or cytosine diphosphate and so on. Examples of well known nucleotide sugars are UDP-glucose, UDP-galactose, UDP-GlcNAc, UDP-GalNAc, UDP-xylose, UDP-glucuronic acid, GDP-mannose and GDP-fucose. It is well known that the conversion of simple monosaccharides into activated nucleotide sugars can be achieved by enzyme catalyzed reaction of a nucleoside triphosphate (NTP) and a glycosyl monophosphate, wherein the glycosyl monophosphate contains a phosphate group at the anomeric carbon.

In order to obtain a nucleoside diphosphate (NDP)-monosaccharide the used monosaccharide needs to be converted into a glycosyl monophosphate derivative. In general, said reaction can be accomplished by applying specific enzymes like phosphotransferases and additionally phosphomutases, if required, to obtain the desired monosaccharide-1-phosphate. Phosphotransferases are enzymes classified under EC number 2.7 that catalyze phosphorylation reactions. Phosphotransferases are further classified according to their acceptor molecule. For example, phosphotransferases under EC 2.7.1 are phosphotransferases with an alcohol group as acceptor. Phosphomutases are isomerases, i.e. enzymes that can catalyze an internal transfer of a phosphate group. Phosphomutases are required in case the phosphorylation of the substrate via phosphotransferase results in a monosaccharide-6-phosphate, like in case of D-mannose or D-glucose for example mannose-6-phosphate and glucose-6-phosphate, respectively. The respective phosphomutase then catalyzes the internal transfer of the phosphate group which results in the conversion of mannose-6-phosphate into mannose-1-phosphate or glucose-6-phosphate into glucose-1-phosphate, respectively.

Kinases are enzymes which form a part of the family of the phosphotransferases. Kinases are enzymes that catalyze the transfer of phosphate groups from high-energy, phosphate-donating molecules to specific substrates. This process is known as phosphorylation, where the substrate gains a phosphate group and the high-energy adenosine triphosphate (ATP) molecule donates a phosphate group. This transesterification produces a phosphorylated substrate and ADP. Thus, in order to obtain a monosaccharide-1-phosphate, suitable kinases like a galactokinase may be applied to obtain galactose 1-phosphate from D-galactose.

With the use of nucleotidyltransferases a nucleoside triphosphate (NTP) and a monosaccharide-1-phosphate can be converted to the respective nucleoside diphosphate (NDP)-monosaccharide. Nucleotidyltransferases are transferase enzymes of phosphorus-containing groups and are classified under EC number 2.7.7. For the different naturally occurring nucleotides nucleotide-specific nucleotidyltransferases are known in the art, e.g. uridyltransferases transfer uridylyl-groups, adenyltransferases transfer adenylyl-groups, guanylyltransferases transfer guanylyl-groups, cytidylyltransferases transfer cytidylyl-groups and thymidilyl-transferases transfer thymidilyl-groups. Thus, nucleotidyltransferases are suitable to catalyze the reaction of monosaccharide-1-phosphates with nucleoside triphosphates, e.g. galactose 1-phosphate with uridine triphosphate (UTP) to obtain UDP-galactose. In case of UDP-galactose a uridylyltransferase is suitable for catalyzing the reaction with uridine triphosphate (UTP).

Uridine diphosphate (UDP)-monosaccharides which relate to naturally occurring UDP-monosaccharides are UDP-galactose, UDP-GalNAc and UDP-GlcNAc. The above described general reaction scheme is not applied to UDP-galactose using uridine triphosphate and galactose 1-phosphate (Gal-1-P) with specific uridylyltransferases, due to the very restricted access to UTP:galactose-1-phosphate uridylyltransferases (EC 2.7.7.10) (see Chem. Commun., 2012, 48, 2728-2730). Instead, UDP-galactose is commonly prepared from UDP-Glucose using galactose-1-phosphate uridylyltransferases (GalT, EC 2.7.7.12) (e.g. see U.S. patent application Ser. No. 09/757,846; Nature Biotech. 1998, 16, 847), thereby requiring a further substrate (UDP-glucose or glucose 1-phosphate) and a further enzyme GalT.

Notwithstanding the aforementioned drawbacks of the UDP-Gal syntheses described in the literature, a further disadvantage of the general reaction scheme to NTP-sugars is based on the fact that the starting materials, in particular the respective nucleoside triphosphates are very expensive and thus the synthesis pathway results in a cost-intensive synthesis of NDP-monosaccharides and in particular of UDP-galactose. As already described above, for UDP-galactose there is a need in the art to provide a cost effective and efficient method for preparation of nucleoside diphosphate monosaccharides, particularly of UDP-galactose from low cost and readily available starting materials.

With regard to UDP-monosaccharides, UDP-galactose relates to naturally occurring activated UDP-sugars in mammals. Therefore UMP has been identified as suitable nucleotide and D-galactose has been identified as suitable monosaccharide for the preparation of UDP-galactose. It should be clear that with regard to an enzyme-catalyzed reaction at least suitable enzymes must be provided. Therefore the inventors have identified UMP and readily available D-galactose as suitable starting materials for the production of UDP-galactose in an enzymatic one-pot cascade reaction.

In order to provide a cost-effective and efficient method for the preparation of UDP-galactose, UMP (uridine monophosphate) and D-galactose were identified as suitable starting materials for the production of UDP-galactose in an enzymatic cascade reaction as depicted in FIG. 1 which consists of (a) the formation of galactose 1-phosphate (Gal-1-P) from D-galactose and adenosine triphosphate (ATP; catalytic amount), (b) the formation of uridine triphosphate (UTP) from UMP and polyphosphate, and (c) the reaction of galactose 1-phosphate with uridine triphosphate (UTP) to UDP-galactose. It was envisioned that UDP-galactose can be produced directly from D-galactose and uridine monophosphate in the presence of a galactokinase, a uridine monophosphate kinase, a polyphosphate kinase, and a glucose-1-phosphate uridylyltransferase.

Surprisingly, the inventors have found that the reaction of galactose 1-phosphate with uridine triphosphate to UDP-galactose can be efficiently catalyzed with a glucose-1-phosphate uridylyltransferase (GalU), an enzyme which is only known for its ability to catalyze the reaction of UTP and α-D-glucose 1-phosphate to diphosphate and UDP-glucose (EC 2.7.7.9). Thus, no further monosaccharide substrate, such as glucose 1-phosphate and no galactose-1-phosphate uridylyltransferase are required for the inventive enzyme cascade. Therefore, the method for producing UDP-Gal according to the present invention is beneficial over the above described methods, since fewer enzymes for the enzyme cascade and fewer expensive starting materials are required, thereby rendering the inventive method more efficient with yields above 99% and less expensive (see Example 2).

Further, the method of the present invention is beneficial over the above described methods known in the art for the enzymatic synthesis of UDP-galactose from D-galactose and uridine triphosphate, since the expensive uridine triphosphate starting material can be avoided and replaced with uridine monophosphate, which results in a cost-effective and efficient method for the preparation of UDP-galactose, as described herein.

Thus, the present invention is directed to a method for producing uridine 5'-diphospho-α-D-galactose comprising the following steps:

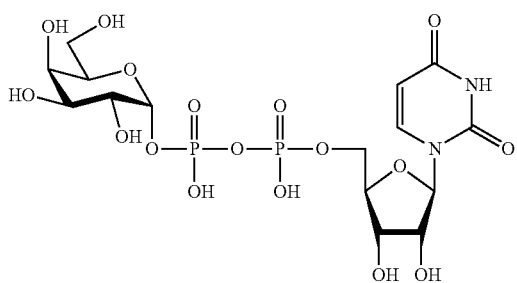

A) providing a solution comprising
   (i) uridine monophosphate and D-galactose represented by the following formulae

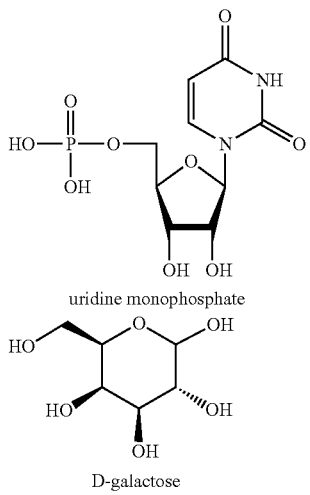

uridine monophosphate

D-galactose (ii) polyphosphate, and adenosine triphosphate; and
   providing a set of enzymes comprising a glucose-1-phosphate uridylyltransferase, a galactokinase, a polyphosphate kinase, and a uridine monophosphate kinase;
B) producing uridine 5'-diphospho-α-D-galactose from uridine monophosphate and D-galactose in the presence of the set of enzymes, polyphosphate, and adenosine triphosphate.

The production step B) of uridine 5'-diphospho-α-D-galactose according to the invention comprises
   (a) forming galactose 1-phosphate (Gal-1-P) from D-galactose and adenosine triphosphate being catalyzed by a galactokinase,
   (b) forming uridine triphosphate (UTP) from uridine monophosphate (UMP), adenosine triphosphate and polyphosphate being catalyzed by a uridine monophosphate kinase and a polyphosphate kinase; and
   (c) reacting galactose 1-phosphate with uridine triphosphate to UDP-galactose in the presence of a glucose-1-phosphate uridylyltransferase.

Apparently, the steps (a) and (b) may be carried out simultaneously or successively. Also, their order may be reverted to (b)→(a)→(c).

Thus, the present invention is directed to a method for producing uridine 5'-diphospho-α-D-galactose comprising the following steps:

A) providing a solution comprising
   (i) uridine monophosphate and D-galactose;
   (ii) polyphosphate, and adenosine triphosphate;
   providing a set of enzymes comprising a glucose-1-phosphate uridylyltransferase, a galactokinase, a polyphosphate kinase, and a uridine monophosphate kinase;
B) producing uridine 5'-diphospho-α-D-galactose from uridine monophosphate and D-galactose in the presence of the set of enzymes, polyphosphate, and adenosine triphosphate by
   (a) forming galactose 1-phosphate (Gal-1-P) from D-galactose and adenosine triphosphate being catalyzed by a galactokinase,
   (b) forming uridine triphosphate (UTP) from uridine monophosphate (UMP), adenosine triphosphate and polyphosphate being catalyzed by a uridine monophosphate kinase and a polyphosphate kinase; and
   (c) reacting galactose 1-phosphate with uridine triphosphate to UDP-galactose in the presence of a glucose-1-phosphate uridylyltransferase.

More specifically, the production step B) of uridine 5'-diphospho-α-D-galactose according to the invention comprises
   (a) forming galactose 1-phosphate (Gal-1-P) from D-galactose and adenosine triphosphate being catalyzed by a galactokinase,
   (b1) forming uridine diphosphate (UDP) from uridine monophosphate and adenosine triphosphate being catalyzed by a uridine monophosphate kinase;
   (b2) forming uridine triphosphate (UTP) from uridine diphosphate and polyphosphate being catalyzed by a polyphosphate kinase; and
   (c) reacting galactose 1-phosphate with uridine triphosphate to UDP-galactose in the presence of a glucose-1-phosphate uridylyltransferase.

Apparently, the step (a) may be carried out before, simultaneously to or after step (b1) or (b2). Thus, the step order may also be reverted to (b1)→(b2)→(a)→(c).

Thus, the present invention is directed to a method for producing uridine 5'-diphospho-α-D-galactose comprising the following steps:
   A) providing a solution comprising
      (i) uridine monophosphate and D-galactose;
      (ii) polyphosphate, and adenosine triphosphate;
      providing a set of enzymes comprising a glucose-1-phosphate uridylyltransferase, a galactokinase, a polyphosphate kinase, and a uridine monophosphate kinase;
   B) producing uridine 5'-diphospho-α-D-galactose from uridine monophosphate and D-galactose in the presence of the set of enzymes, polyphosphate, and adenosine triphosphate by
      (a) forming galactose 1-phosphate (Gal-1-P) from D-galactose and adenosine triphosphate being catalyzed by a galactokinase,
      (b1) forming uridine diphosphate (UDP) from uridine monophosphate and adenosine triphosphate being catalyzed by a uridine monophosphate kinase;
      (b2) forming uridine triphosphate (UTP) from uridine diphosphate and polyphosphate being catalyzed by a polyphosphate kinase; and
      (c) reacting galactose 1-phosphate with uridine triphosphate to UDP-galactose in the presence of a glucose-1-phosphate uridylyltransferase.

The inventive method for producing UDP-galactose has the following significant advantages over the methods described in the prior art:

significant cost reduction with respect to starting materials, i.e. no expensive UDP or UTP is required, the method can be performed in a continuous manner, thereby potentially allowing providing UDP-galactose on a ton scale per year, cell-free process, thereby avoiding adverse GMO aspects (regulation, labelling), direct use of cell-free extracts, no costs for biocatalyst purification, enzymes can be immobilized on low-cost, commercially available and ready to use solid supports, nearly quantitative yield with respect to galactose, high scalability renders the inventive method useful for industrial applications.

In one embodiment the enzymes are immobilized on a solid support. Thus, the present invention is directed to a method for producing uridine 5'-diphospho-α-D-galactose comprising the following steps:

A) providing a solution comprising
  (i) uridine monophosphate and D-galactose;
  (ii) polyphosphate, and adenosine triphosphate; and
  providing a set of enzymes comprising a glucose-1-phosphate uridylyltransferase, a galactokinase, a polyphosphate kinase, and a uridine monophosphate kinase;

B) producing uridine 5'-diphospho-α-D-galactose from uridine monophosphate and D-galactose in the presence of the set of enzymes, polyphosphate, and adenosine triphosphate;

wherein the set of enzymes is immobilized on a solid support. Preferably, the set of enzymes is co-immobilized on a solid support without affecting the enzymatic activity of each enzyme.

A further aspect of the present invention is directed to the galactosylation of molecules and biomolecules including saccharides, proteins, peptides, glycoproteins or glycopeptides, particularly human milk oligosaccharides (HMO) and (monoclonal) antibodies, comprising the steps of:

A) providing a solution comprising
  (i) uridine monophosphate and D-galactose;
  (ii) polyphosphate, and adenosine triphosphate; and
  providing a set of enzymes comprising a glucose-1-phosphate uridylyltransferase, a galactokinase, a polyphosphate kinase, and a uridine monophosphate kinase;

B) producing uridine 5'-diphospho-α-D-galactose from uridine monophosphate and D-galactose in the presence of the set of enzymes, polyphosphate, and adenosine triphosphate; and D) producing a galactosylated saccharide, galactosylated glycopeptide, galactosylated glycoprotein, galactosylated protein, galactosylated peptide or galactosylated small molecule from uridine 5'-diphospho-α-D-galactose and a saccharide, glycopeptide, glycoprotein, protein, peptide or small molecule by forming an O-glycosidic bond between uridine 5'-diphospho-α-D-galactose and an available hydroxyl group of the saccharide, glycopeptide, glycoprotein, protein, peptide or small molecule in the presence of a galactosyltransferase.

In one embodiment of the inventive method for galactosylation, UTP is regenerated from the side product UDP. Therefore, only catalytic amounts of UMP are required. Thus, the inventive method for galactosylation comprises the steps of:

A) providing a solution comprising
  (i) uridine monophosphate and D-galactose;
  (ii) polyphosphate, and adenosine triphosphate; and
  providing a set of enzymes comprising a glucose-1-phosphate uridylyltransferase, a galactokinase, a polyphosphate kinase, and a uridine monophosphate kinase;

B) producing uridine 5'-diphospho-α-D-galactose from uridine monophosphate and D-galactose in the presence of the set of enzymes, polyphosphate, and adenosine triphosphate;

D) producing a galactosylated saccharide, galactosylated glycopeptide, galactosylated glycoprotein, galactosylated protein, galactosylated peptide or galactosylated small molecule from uridine 5'-diphospho-α-D-galactose and a saccharide, glycopeptide, glycoprotein, protein, peptide or small molecule by forming an O-glycosidic bond between uridine 5'-diphospho-α-D-galactose and an available hydroxyl group of the saccharide, glycopeptide, glycoprotein, protein, peptide or small molecule in the presence of a galactosyltransferase; and E) recycling of uridine diphosphate formed in step D) to obtain uridine triphosphate.

Preferably, the set of enzymes is co-immobilized on a solid support without affecting the enzymatic activity of each enzyme. Said solid support can be reused multiple times without affecting the productivity, if the solid support consists of a polymer backbone of high mechanical strength, such as methacrylate functionalized with epoxy groups. Therefore, a further aspect of the present invention is directed to a set of enzymes comprising a glucose-1-phosphate uridylyltransferase, a galactokinase, a polyphosphate kinase, and a uridine monophosphate kinase; wherein the set of enzymes is co-immobilized on a solid support functionalized with epoxy groups. Preferably, the solid support is a methacrylate polymer. Preferably, a galactosyltransferase is co-immobilized with the set of enzymes on the solid support.

DETAILED DESCRIPTION OF THE INVENTION

Definitions

As used herein, the term "polyphosphate" refers to any salts containing several P—O—P bonds generated by corner sharing of six or more phosphate ($PO_4$) tetrahedral, leading to the formation of long chains. The term "$PolyP_n$" is synonymously used, wherein n represents average chain length of the number of phosphate residues, e.g. $PolyP_{25}$ refers to a polyphosphate having about 25 phosphate residues and $PolyP_{14}$ refers to a polyphosphate having about 14 phosphate residues.

As used herein, the term "uridine kinase" or refers to a polypeptide having uridine kinase activity, i.e. a uridine kinase catalyzes the reaction of uridine to uridine 5'-monophosphate in the presence of adenosine triphosphate. The uridine kinase belongs to the EC class 2.7.1.48.

As used herein, the term "polyphosphate kinase" refers to a polypeptide having polyphosphate kinase activity, i.e. a polyphosphate kinase catalyzes the following reactions:

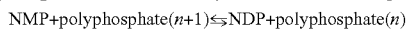

NMP+polyphosphate(n+1)⇌NDP+polyphosphate(n)

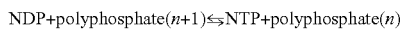

NDP+polyphosphate(n+1)⇌NTP+polyphosphate(n)

with N being a nucleotide such as guanosine, adenosine, uridine etc. and NMP being nucleoside monophosphate, NDP being nucleoside diphosphate and NTP being nucleoside triphosphate.

In case of uridine the polyphosphate kinase catalyzes the following reactions:

ADP+polyphosphate($n$+1)⇌ATP+polyphosphate($n$)

AMP+polyphosphate($n$+1)⇌ADP+polyphosphate($n$)

UDP+polyphosphate($n$+1)⇌UTP+polyphosphate($n$)

The polyphosphate kinase belongs to the EC class 2.7.4.1. Representatives of the polyphosphate kinase enzyme used in the inventive methods described herein include but are not limited to polyphosphate kinase 1 (PPK1), polyphosphate kinase 2 (PPK2), 2-domain polyphosphate kinase 2 (2D-PPK2) and 1-domain polyphosphate kinase 2 (1D-PPK2) and polyphosphate kinase 3 (PPK3).

As used herein, the term "glucose 1-phosphate uridylyltransferase" refers to a polypeptide having a uridylyltransferase activity, i.e. a UTP: α-D-glucose-1-phosphate uridylyltransferase and that catalyzes the following reaction:

Glc-1-P+UTP⇌UDP-Glc+PPi

The glucose 1-phosphate uridylyltransferase (GalU) belongs to EC class 2.7.7.9. As the inventors have found, the glucose 1-phosphate uridylyltransferase also catalyzes the transfer of UTP to α-D-galactose 1-phosphate:

Gal-1-P+UTP⇌UDP-Gal+PPi

As used herein, the term "pyrophosphatase" refers to a polypeptide having pyrophosphatase activity, i.e. a polypeptide that catalyzes the following reaction:

PPi+H$_2$O⇌2Pi wherein PPi refers to pyrophosphate and Pi to phosphate.

The pyrophosphatase belongs to EC classes 3.6.1.1. In this context, the term "diphosphatase" refers to a pyrophosphatase polypeptide which catalyzes the hydrolysis of diphosphate to phosphate.

As used herein, the term "galactokinase" refers to a polypeptide having kinase activity, i.e. a kinase that catalyzes the following phosphorylation to α-D-galactose 1-phosphate:

Gal+ATP⇌α-Gal-1-P+ADP

The galactokinase belongs to the EC class 2.7.1.6.

As used herein, the term "uracil phosphoribosyltransferase" refers to a polypeptide having phosphoribosyltransferase activity, i.e. a transferase that catalyzes the following reaction:

uracil+PRPP⇌UMP+PPi wherein PRPP refers to a phosphorylated pentose, preferably a phosphorylated ribose and most preferably 5-phospho-α-D-ribose 1-diphosphate. Exemplarily, the transferase is, but not limited to, a uracil phosphoribosyltransferase belonging to EC class 2.4.2.9 or an AMP phosphorylase belonging to EC class 2.4.2.57, of which such a transferase activity is also known.

As used herein, the term "UMP synthase" refers to a polypeptide having uridine monophosphate synthetase activity, i.e. a synthase that catalyzes the following reaction:

OMP⇌UMP+CO$_2$ wherein OMP refers to orotidine-5'-phosphate. The term UMP synthase is synonymously used for orotidine 5'-phosphate decarboxylase and this enzyme belongs to EC class 4.1.1.23.

As used herein, the term "orotate phosphoribosyltransferase" refers to a polypeptide having orotate phosphoribosyltransferase activity, i.e. a transferase that catalyzes the following reaction:

orotic acid+PRPP⇌OMP+PPi

The transferase belongs to EC class 2.4.2.10.

As used herein, the term "galactosyltransferase" refers to polypeptide having galactosyltransferase activity, i.e. a polypeptide that catalyzes the transfer of galactose from UDP-Gal to acceptor (bio)molecules. Preferably, acceptors are saccharides, such as glucose or N-acetylglucosamine. Preferably, the galactosyltransferase is a β-galactosyltransferase and more preferably a β-1,4-galactosyltransferase that catalyzes the transfer of galactose from UDP-Gal to acceptor saccharide by forming a β-glycosidic linkage between galactose and 4 position of the acceptor saccharide:

β-Galactosyltransferases are preferred over α-galactosyltransferases as terminal α-galactosyl moieties are naturally not occurring in human and thus may trigger an immune response in terms of antibody reaction against α-galactosyl structures on antibodies etc. Galactosyltransferases belong to the EC class 2.4.1.-.

"Percentage of sequence identity" and "percentage homology" are used interchangeably herein to refer to comparisons among polypeptides, and are determined by comparing two optimally aligned sequences over a comparison window, wherein the portion of the polypeptide sequence in the comparison window may comprise additions or deletions (i.e. gaps) as compared to the reference sequence for optimal alignment of the two sequences. The percentage may be calculated by determining the number of positions at which the identical amino acid residue occurs in both sequences to yield the number of matched positions, dividing the number of matched positions by the total number of positions in the window of comparison and multiplying the result by 100 to yield the percentage of sequence identity. Alternatively, the percentage may be calculated by determining the number of positions at which either the identical amino acid residue occurs in both sequences or an amino acid residue is aligned with a gap to yield the number of matched positions, dividing the number of matched positions by the total number of positions in the window of comparison and multiplying the result by 100 to yield the percentage of sequence identity. Those of skill in the art appreciate that there are many established algorithms available to align two sequences.

"Reference sequence" refers to a defined sequence used as a basis for a sequence comparison. A reference sequence may be a subset of a larger sequence, for example, a segment of a full-length polypeptide sequence. Generally, a reference sequence is at least 20 amino acid residues in length, at least 25 residues in length, at least 50 residues in length, or the full length of the polypeptide. Since two polypeptides may each (1) comprise a sequence (i.e., a portion of the complete sequence) that is similar between the two sequences, and (2) may further comprise a sequence that is divergent between the two sequences, sequence comparisons between two (or more) polypeptides are typically performed by comparing sequences of the two polypeptides over a "comparison window" to identify and compare local regions of sequence similarity. In some embodiments, a "reference sequence" can be based on a primary amino acid sequence, where the reference sequence is a sequence that can have one or more changes in the primary sequence.

As used herein, "saccharide" refers to but not restricted to monosaccharide, disaccharide, trisaccharide, tetrasaccharide, pentasaccharide, hexasaccharide, heptasaccharide, octasaccharide . . . , oligosaccharide, glycan and polysaccharide. The saccharide comprises preferably monosaccharide units selected from: D-Arabinose, D-Lyxose, D-Ribose, D-Xylose, L-Arabinose, L-Lyxose, L-Ribose, L-Xylose, D-Ribulose, D-Xylulose, L-Ribulose, L-Xylulose, D-Deoxyribose, L-Deoxyribose, D-Erythrose, D-Threose, L-glycero-D-manno-Heptose, D-glycero-D-manno-Heptose, D-Allose, D-Altrose, D-Glucose, D-Mannose, D-Gulose, D-Idose, D-Galactose, D-Talose, D-psicose, D-fructose, D-sorbose, D-tagatose, 6-Deoxy-L-altrose, 6-Deoxy-D-talose, D-Fucose, L-Fucose, D-Rhamnose, L-Rhamnose, D-Quinovose, Olivose, Tyvelose, Ascarylose, Abequose, Paratose, Digitoxose, Colitose, D-Glucosamine, D-Galactosamine, D-Mannosamine, D-Allosamine, I-Altrosam ine, D-Gulosamine, L-Idosamine, D-Talosamine, N-Acetyl-D-glucosamine, N-Acetyl-D-galactosamine, N-Acetyl-D-mannosamine, N-Acetyl-D-allosamine, N-Acetyl-L-altrosamine, N-Acetyl-D-gulosamine, N-Acetyl-L-idosamine, N-Acetyl-D-talosamine, N-Acetyl-D-fucosamine, N-Acetyl-L-fucosamine, N-Acetyl-L-rhamnosamine, N-Acetyl-D-quinovosamine, D-Glucuronic acid, D-Galacturonic acid, D-Mannuronic acid, D-Alluronic acid, L-Altruronic acid, D-Guluronic acid, L-Guluronic acid, L-Iduronic acid, D-Taluronic acid, Neuraminic acid, N-Acetylneuraminic acid, N-Glycolylneuraminic acid, Apiose, Bacillosamine, Thevetose, Acofriose, Cymarose, Muramic acid, N-Acetylmuramic acid, N-Glycolylmuramic acid, 3-Deoxy-lyxo-heptulosaric acid, Ketodeoxyoctonic acid, and Ketodeoxynononic acid. Preferably the monosaccharide units belong to the following group of α- and β-D/L-carbohydrates comprising or consisting of: α-D-ribopyranose, α-D-arabinopyranose, α-D-xylopyranose, α-D-lyxopyranose, α-D-allopyranose, α-D-altropyranose, α-D-glucopyranose, α-D-mannpyranose, α-D-glucopyranose, α-D-idopyranose, α-D-galactopyranose, α-D-talopyranose, α-D-psicopyranose, α-D-fructopyranose, α-D-sorbopyranose, α-D-tagatopyranose, α-D-ribofuranose, α-D-arabinofuranose, α-D-xylofuranose, α-D-lyxofuranose, α-D-Allofuranose, α-D-Altrofuranose, α-D-Glucofuranose, α-D-Mannofuranose, α-D-gulofuranose, α-D-idofuranose, α-D-galactofuranose, α-D-talofuranose, α-D-psicofuranose, α-D-fructofuranose, α-D-sorbofuranose, α-D-tagatofuranose, α-D-xylulofuranose, α-D-ribulofuranose, α-D-threofuranose, α-D-rhamnopyranose, α-D-erythrofuranose, α-D-glucosamine, α-D-glucopyranuronic acid, β-D-ribopyranose, β-D-arabinopyranose, β-D-xylopyranose, β-D-lyxopyranose, β-D-allopyranose, β-D-altropyranose, β-D-glucopyranose, β-D-mannpyranose, β-D-glucopyranose, β-D-idopyranose, β-D-galactopyranose, β-D-talopyranose, β-D-psicopyranose, β-D-fructopyranose, β-D-sorbopyranose, β-D-tagatopyranose, β-D-ribofuranose, β-D-arabinofuranose, β-D-xylofuranose, β-D-lyxofuranose, β-D-rhamnopyranose, β-D-allofuranose, β-D-altrofuranose, β-D-glucofuranose, β-D-mannofuranose, β-D-gulofuranose, β-D-idofuranose, β-D-galactofuranose, β-D-talofuranose, β-D-psicofuranose, β-D-fructofuranose, β-D-sorbofuranose, β-D-tagatofuranose, β-D-xylulofuranose, β-D-ribulofuranose, β-D-threofuranose, β-D-erythrofuranose, β-D-glucosamine, β-D-glucopyranuronic acid, α-L-ribopyranose, α-L-arabinopyranose, α-L-xylopyranose, α-L-lyxopyranose, α-L-allopyranose, α-L-altropyranose, α-L-glucopyranose, α-L-mannpyranose, α-L-glucopyranose, α-L-idopyranose, α-L-galactopyranose, α-L-talopyranose, α-L-psicopyranose, α-L-fructopyranose, α-L-sorbopyranose, α-L-tagatopyranose, α-L-rhamnopyranose, α-L-ribofuranose, α-L-arabinofuranose, α-L-xylofuranose, α-L-lyxofuranose, α-L-Allofuranose, α-L-Altrofuranose, α-L-Glucofuranose, α-L-Mannofuranose, α-L-gulofuranose, α-L-idofuranose, α-L-galactofuranose, α-L-talofuranose, α-L-psicofuranose, α-L-fructofuranose, α-L-sorbofuranose, α-L-tagatofuranose, α-L-xylulofuranose, α-L-ribulofuranose, α-L-threofuranose, α-L-erythrofuranose, α-L-glucosamine, α-L-glucopyranuronic acid, β-L-ribopyranose, β-L-arabinopyranose, β-L-xylopyranose, β-L-lyxopyranose, β-L-allopyranose, β-L-altropyranose, β-L-glucopyranose, β-L-mannpyranose, β-L-glucopyranose, β-L-idopyranose, β-L-galactopyranose, β-L-talopyranose, β-L-psicopyranose, β-L-fructopyranose, β-L-sorbopyranose, β-L-tagatopyranose, β-L-ribofuranose, β-L-arabinofuranose, β-L-xylofuranose, β-L-lyxofuranose, β-L-allofuranose, β-L-altrofuranose, β-L-glucofuranose, β-L-mannofuranose, β-L-gulofuranose, β-L-idofuranose, β-L-galactofuranose, β-L-talofuranose, β-L-psicofuranose, β-L-fructofuranose, β-L-sorbofuranose, β-L-tagatofuranose, β-L-xylulofuranose, β-L-ribulofuranose, β-L-threofuranose, β-L-erythrofuranose, β-L-glucosamine, β-L-glucopyranuronic acid, and β-L-rhamnopyranose.

The saccharides are further optionally modified to carry amide, carbonate, carbamate, carbonyl, thiocarbonyl, carboxy, thiocarboxy, ester, thioester, ether, epoxy, hydroxyalkyl, alkylenyl, phenylene, alkenyl, imino, imide, isourea, thiocarbamate, thiourea and/or urea moieties.

As used herein, the term "glycopeptide" refers to a peptide that contains carbohydrate moieties covalently attached to the side chains of the amino acid residues that constitute the peptide. The carbohydrate moieties form side chains and are either O-glycosidic connected to the hydroxy group of a serine or threonine residue or N-glycosidic connected to the amido nitrogen of an asparagine residue.

As used herein, the term "glycoprotein" refers to a polypeptide that contains carbohydrate moieties covalently attached to the side chains of the amino acid residues that constitute the polypeptide. The carbohydrate moieties form side chains and are either O-glycosidic connected to the hydroxy group of a serine or threonine residue or N-glycosidic connected to the amido nitrogen of an asparagine residue.

As used herein, the term "protein" refers to a polypeptide that contains or lacks of carbohydrate moieties covalently attached to the side chains of the amino acid residues that constitute the polypeptide including aglycosylated proteins and glycosylated proteins.

As used herein, the term "peptide" refers to a peptide that contains or lacks of carbohydrate moieties covalently attached to the side chains of the amino acid residues that constitute the peptide, including aglycosylated peptides and glycosylated peptides.

As used herein, the term "therapeutic antibody" refers to an antibody which may be administered to humans or animals to have a desired effect in particular in the treatment of disease. Such therapeutic antibodies will generally be monoclonal antibodies and will generally have been genetically engineered. If the antibody is a recombinant antibody it may be humanised. Alternatively, the therapeutic antibody may be a polyclonal antibody.

As used herein, the term "bioconjugate" refers to a molecular construct consisting of at least two molecules which are covalently bound to each other and wherein at least one of which is a biomolecule, i.e. a molecule present in organisms that are essential to one or more typically biological processes. Exemplarily bioconjugates are carbohydrate conjugate vaccines consisting of a carbohydrate antigen covalently coupled to a carrier protein, and antibody drug conjugates.

As used herein, the term "carbohydrate conjugate vaccine" refers to a conjugate containing a carbohydrate antigen covalently bound to an immunogenic carrier. The carbohydrate antigen can be, but is not limited to, a bacterial capsular saccharide, a saccharide of a viral glycoprotein, a saccharide antigen of sporozoa or parasites, a saccharide antigen of pathogenic fungi, or a saccharide antigen which is specific to cancer cells. The immunogenic carrier can be, but is not limited to, a carrier protein selected from toxoids, including tetanus toxoid (TT), diphtheria toxoid (DT), cross-reaction material 197 ($CRM_{197}$), protein D of non-typeable *H. influenzae*, outer membrane protein complexes of *Neisseria meningitidis* capsular group B (OMPCs), exotoxin A of *P. aeruginosa* (EPA), *C. difficile* toxin A (CDTA), pneumococcal proteins, such as pneumococcal surface protein A (PspA), pneumococcal histidine triad D (PhtD), detoxified pneumolysin (dPly), and spr96/2021, *S. aureus* α toxin and Shiga toxin 1 b.

The term "solid support" as used herein refers to an insoluble, functionalized, material to which enzymes or other reagents may be attached or immobilized, directly or via a linker bearing an anchoring group, allowing enzymes to be readily separated (by washing, filtration, centrifugation, etc.) from excess reagents, soluble reaction products, by-products, or solvents. A solid support can be composed of organic polymers such as polystyrene, polyethylene, polypropylene, polyfluoroethylene, polyethyleneoxy, and polyacrylamide, as well as co-polymers and grafts thereof. A solid support can also be inorganic, such as glass, silica, controlled pore glass (CPG), reverse phase silica or metal, such as gold or platinum. A solid support can also consist of magnetic particles. For an overview of suitable support materials for enzyme immobilization see Zdarta et al. *Catalysts* 2018, 8, 92, and Datta et al. Biotech 2013 3:1-9.

The configuration of a solid support can be in the form of beads, monoliths, spheres, particles, a particle bed, a fiber mat, granules, a gel, a membrane, a hollow-fiber membrane, a mixed-matrix membrane or a surface. Surfaces can be planar, substantially planar, or non-planar. Solid supports can be porous or non-porous, and can have swelling or non-swelling characteristics. A solid support can be configured in the form of a well, depression, or other container, vessel, feature, or location.

Surprisingly, the inventors have found that the reaction of galactose 1-phosphate with uridine triphosphate to UDP-galactose can be efficiently catalyzed with a glucose-1-phosphate uridylyltransferase (GalU), an enzyme which is only known for its ability to catalyze the reaction of UTP and α-D-glucose 1-phosphate to diphosphate and UDP-glucose (EC 2.7.7.9). Thus, no further monosaccharide substrate, such as glucose 1-phosphate and no galactose-1-phosphate uridylyltransferase are required for the inventive enzyme cascade.

Therefore, the method for producing UDP-Gal according to the present invention is beneficial over the methods of the prior art, since fewer enzymes for the enzyme cascade and fewer expensive starting materials are required, thereby rendering the inventive method more efficient with yields above 99% and less expensive (see Example 2).

In one embodiment of the inventive method, higher concentrated reaction mixtures are used in order to reduce process costs. Thus, the concentration of UMP and D-galactose in the solution provided in step A) is preferably in the range of 0.01 mM to 100,000 mM. More preferably, the concentration of UMP and D-galactose is in the range of 0.05 mM to 50,000 mM. More preferably, the concentration of UMP and D-galactose is in the range of 0.1 mM to 30,000 mM. More preferably, the concentration of UMP and D-galactose is in the range of 0.2 mM to 15,000 mM.

Thus, the present invention is directed to a method for producing uridine 5'-diphospho-α-D-galactose comprising the following steps:
   A) providing a solution comprising
      (i) uridine monophosphate and D-galactose;
      (ii) polyphosphate, and adenosine triphosphate;
      providing a set of enzymes comprising a glucose-1-phosphate uridylyltransferase, a galactokinase, a polyphosphate kinase, and a uridine monophosphate kinase;
   B) producing uridine 5'-diphospho-α-D-galactose from uridine monophosphate and D-galactose in the presence of the set of enzymes, polyphosphate, and adenosine triphosphate,
wherein the concentration of uridine monophosphate and D-galactose in the solution provided in step A) is in the range of 0.2 mM to 15,000 mM.

Preferably, the concentration of the enzymes in the set of enzymes is between 0.0001 mg/mL and 100 mg/mL based on the total volume of the solution provided in step A).

As a side product in the reaction of galactose 1-phosphate with uridine triphosphate to UDP-galactose, pyrophosphate (PPi) is formed. Although pyrophosphate is unstable in aqueous solution, it only slowly hydrolyzes into inorganic phosphate (Pi). A high concentration of pyrophosphate lowers the activity of the glucose-1-phosphate uridylyltransferase enzyme involved in the UDP-galactose formation since PPi binds metal ions such as $Mg^{2+}$ and precipitates from the solution. In addition, pyrophosphate is known for its ability to inhibit uridylyl- and guanylyltransferases. The enzyme pyrophosphatase is able to catalyze the hydrolysis of pyrophosphate to phosphate, thereby effectively rendering the UDP-galactose formation irreversible. Thus, in a preferred embodiment of the present invention the set of enzymes further comprises a pyrophosphatase. Therefore, the method for producing uridine 5'-diphospho-α-D-galactose according to the present invention comprises the following steps:
   A) providing a solution comprising
      (i) uridine monophosphate and D-galactose;
      (ii) polyphosphate, and adenosine triphosphate;
      providing a set of enzymes comprising a glucose-1-phosphate uridylyltransferase, a galactokinase, a polyphosphate kinase, a pyrophosphatase, and a uridine monophosphate kinase;
   B) producing uridine 5'-diphospho-α-D-galactose from uridine monophosphate and D-galactose in the presence of the set of enzymes, polyphosphate, and adenosine triphosphate.

Reworded, the inventive method for producing uridine 5'-diphospho-α-D-galactose comprises the following steps:
   A) providing a solution comprising
      (i) uridine monophosphate and D-galactose;
      (ii) polyphosphate, and adenosine triphosphate;
      providing a set of enzymes comprising a glucose-1-phosphate uridylyltransferase, a galactokinase, a polyphosphate kinase, a pyrophosphatase, and a uridine monophosphate kinase;
   B) producing uridine 5'-diphospho-α-D-galactose from uridine monophosphate and D-galactose in the presence of the set of enzymes, polyphosphate, and adenosine triphosphate by
      (a) forming galactose 1-phosphate (Gal-1-P) from D-galactose and adenosine triphosphate being catalyzed by a galactokinase, (b1) forming uridine diphosphate (UDP) from uridine monophosphate and adenosine triphosphate being catalyzed by a uridine monophosphate kinase;
(b2) forming uridine triphosphate (UTP) from uridine diphosphate and polyphosphate being catalyzed by a polyphosphate kinase; and
(c') reacting galactose 1-phosphate with uridine triphosphate to UDP-galactose in the presence of a glucose-1-phosphate uridylyltransferase; and
(c") converting pyrophosphate to phosphate in the presence of a pyrophosphatase.

Preferably, the pyrophosphatase used in the inventive methods described herein is an inorganic pyrophosphatase. Preferably, the pyrophosphatase is an inorganic pyrophosphatase from *Pasteurella multocida* (PmPpA).

Polyphosphate is able to form stable, water-soluble complexes with metal ions (e.g. $Ca^{2+}$, $Mg^{2+}$, $Fe^{2+/3+}$) which were initially dissolved in aqueous media. This effect is called sequestration and prevents the bound metal ions from participating in reactions, particularly enzymatic reactions. Therefore, the sequestered metal ions, particularly $Mg^{2+}$ and $Mn^{2+}$, cannot act as co-factor for the enzymes involved in the inventive methods described herein. As the ability of a particular polyphosphate to sequester a particular metal ion decreases with increasing chain length of the polyphosphate, long-chain polyphosphates are preferred in the present invention. More preferred are polyphosphates having at least 14 phosphate residues. Most preferred are polyphosphates having at least 25 phosphate residues.

Thus, the present invention is directed to a method for producing uridine 5'-diphospho-α-D-galactose comprising the following steps:
A) providing a solution comprising
  (i) uridine monophosphate and D-galactose;
  (ii) polyphosphate, and adenosine triphosphate;
  providing a set of enzymes comprising a glucose-1-phosphate uridylyltransferase, a galactokinase, a polyphosphate kinase, and a uridine monophosphate kinase;
B) producing uridine 5'-diphospho-α-D-galactose from uridine monophosphate and D-galactose in the presence of the set of enzymes, polyphosphate, and adenosine triphosphate, wherein the polyphosphate is a long-chain polyphosphate having at least 25 phosphate residues.

Preferably, the method for producing uridine 5'-diphospho-α-D-galactose comprises the following steps:
A) providing a solution comprising
  (i) uridine monophosphate and D-galactose;
  (ii) polyphosphate, and adenosine triphosphate;
  providing a set of enzymes comprising a glucose-1-phosphate uridylyltransferase, a galactokinase, a polyphosphate kinase, a pyrophosphatase and a uridine monophosphate kinase;
B) producing uridine 5'-diphospho-α-D-galactose from uridine monophosphate and D-galactose in the presence of the set of enzymes, polyphosphate, and adenosine triphosphate;
wherein the polyphosphate is a long-chain polyphosphate having at least 25 phosphate residues.

Preferably, the enzymes are present in a single reaction mixture with the other substrates. The mixture may be homogenous (solution) or heterogeneous. The enzymes may be immobilized on a solid support or not. Thus, the uridine 5'-diphospho-α-D-galactose is produced in a single reaction mixture according to a further aspect of the inventive method.

Thus, the method for producing uridine 5'-diphospho-α-D-galactose comprises the following steps:
A) providing a mixture comprising
  (i) uridine monophosphate and D-galactose;
  (ii) polyphosphate, and adenosine triphosphate; and
  (iii) a set of enzymes comprising a glucose-1-phosphate uridylyltransferase, a galactokinase, a polyphosphate kinase, and a uridine monophosphate kinase;
B) producing uridine 5'-diphospho-α-D-galactose from uridine monophosphate and D-galactose in the presence of the set of enzymes, polyphosphate, and adenosine triphosphate.

Also, the method for producing uridine 5'-diphospho-α-D-galactose comprises the following steps:
A) providing a solution comprising
  (i) uridine monophosphate and D-galactose;
  (ii) polyphosphate, and adenosine triphosphate; and
  (iii) a set of enzymes comprising a glucose-1-phosphate uridylyltransferase, a galactokinase, a polyphosphate kinase, and a uridine monophosphate kinase;
B) producing uridine 5'-diphospho-α-D-galactose from uridine monophosphate and D-galactose in the presence of the set of enzymes, polyphosphate, and adenosine triphosphate.

Reworded, the method for producing uridine 5'-diphospho-α-D-galactose comprises the following steps:
A) providing a mixture comprising
  (i) uridine monophosphate and D-galactose;
  (ii) polyphosphate, and adenosine triphosphate; and
  (iii) at least four enzymes comprising a glucose-1-phosphate uridylyltransferase, a galactokinase, a polyphosphate kinase, and a uridine monophosphate kinase;
B) producing uridine 5'-diphospho-α-D-galactose from uridine monophosphate and D-galactose in the presence of the at least four of enzymes, polyphosphate, and adenosine triphosphate.

Preferably, the method for producing uridine 5'-diphospho-α-D-galactose comprises the following steps:
A) providing a solution comprising
  (i) uridine monophosphate and D-galactose;
  (ii) polyphosphate, and adenosine triphosphate; and
  (iii) a set of enzymes comprising a glucose-1-phosphate uridylyltransferase, a galactokinase, a polyphosphate kinase, optionally a pyrophosphatase, and a uridine monophosphate kinase; and
B) producing uridine 5'-diphospho-α-D-galactose from uridine monophosphate and D-galactose in the presence of the set of enzymes, polyphosphate, and adenosine triphosphate.

Polyphosphate serves as the only energy carrier in the inventive methods described herein and is used as a phosphate source in the regeneration of ATP from ADP using a polyphosphate kinase 3 (PPK3). The regeneration of ATP can be enhanced by adding a 1-domain polyphosphate kinase (1D-PPK), which also catalyzes the phosphorylation of ADP to ATP, preferably a 1-domain polyphosphate kinase 2 (1D-PPK2) to the enzyme cascade of the inventive methods. Moreover, nucleoside phosphates, such as ADP are instable in aqueous media and tend to hydrolyze rapidly. To avoid the loss of ADP by hydrolysis to AMP, a 2-domain polyphosphate kinase (2D-PPK) which catalyzes the phosphorylation of AMP to ADP, preferably a 2-domain polyphosphate kinase 2 (2D-PPK2) can be added along with a 1D-PPK or alone to the inventive enzyme cascade.

Thus, in one embodiment of the present invention the method for producing uridine 5'-diphospho-α-D-galactose comprises the following steps;
- A) providing a solution comprising
  - (i) uridine monophosphate and D-galactose;
  - (ii) polyphosphate, and adenosine triphosphate;
  - providing a set of enzymes comprising a glucose-1-phosphate uridylyltransferase, a galactokinase, a polyphosphate kinase, a uridine monophosphate kinase, and a 1-domain polyphosphate kinase and/or a 2-domain polyphosphate kinase;
- B) producing uridine 5'-diphospho-α-D-galactose from uridine monophosphate and D-galactose in the presence of the set of enzymes, polyphosphate, and adenosine triphosphate.

Preferably, the method for producing uridine 5'-diphospho-α-D-galactose comprises the following steps;
- A) providing a solution comprising
  - (i) uridine monophosphate and D-galactose;
  - (ii) polyphosphate, and adenosine triphosphate;
  - providing a set of enzymes comprising a glucose-1-phosphate uridylyltransferase, a galactokinase, a polyphosphate kinase, a uridine monophosphate kinase, a 1-domain polyphosphate kinase and a 2-domain polyphosphate kinase;
- B) producing uridine 5'-diphospho-α-D-galactose from uridine monophosphate and D-galactose in the presence of the set of enzymes, polyphosphate, and adenosine triphosphate.

Preferably, the method for producing uridine 5'-diphospho-α-D-galactose comprises the following steps;
- A) providing a solution comprising
  - (i) uridine monophosphate and D-galactose;
  - (ii) polyphosphate, and adenosine triphosphate;
  - providing a set of enzymes comprising a glucose-1-phosphate uridylyltransferase, a galactokinase, a polyphosphate kinase, a uridine monophosphate kinase, and a 1-domain polyphosphate kinase;
- B) producing uridine 5'-diphospho-α-D-galactose from uridine monophosphate and D-galactose in the presence of the set of enzymes, polyphosphate, and adenosine triphosphate.

Preferably, the method for producing uridine 5'-diphospho-α-D-galactose comprises the following steps;
- A) providing a solution comprising
  - (i) uridine monophosphate and D-galactose;
  - (ii) polyphosphate, and adenosine triphosphate;
  - providing a set of enzymes comprising a glucose-1-phosphate uridylyltransferase, a galactokinase, a polyphosphate kinase, a uridine monophosphate kinase, and a 2-domain polyphosphate kinase;
- B) producing uridine 5'-diphospho-α-D-galactose from uridine monophosphate and D-galactose in the presence of the set of enzymes, polyphosphate, and adenosine triphosphate.

Preferably, the method for producing uridine 5'-diphospho-α-D-galactose comprises the following steps;
- A) providing a solution comprising
  - (i) uridine monophosphate and D-galactose;
  - (ii) polyphosphate, and adenosine triphosphate;
  - providing a set of enzymes comprising a glucose-1-phosphate uridylyltransferase, a galactokinase, a polyphosphate kinase, a uridine monophosphate kinase, a 1-domain polyphosphate kinase and/or a 2-domain polyphosphate kinase, and optionally a pyrophosphatase;
- B) producing uridine 5'-diphospho-α-D-galactose from uridine monophosphate and D-galactose in the presence of the set of enzymes, polyphosphate, and adenosine triphosphate.

As ATP is continuously regenerated from ADP and polyphosphate in the inventive methods described herein, the production of UDP-galactose can be performed with catalytic amount of ATP. Thus, in one embodiment of the present invention the method for producing uridine 5'-diphospho-α-D-galactose comprises the following steps;
- A) providing a solution comprising
  - (i) uridine monophosphate and D-galactose;
  - (ii) polyphosphate, and adenosine triphosphate in a catalytic amount;
  - providing a set of enzymes comprising a glucose-1-phosphate uridylyltransferase, a galactokinase, a polyphosphate kinase, and a uridine monophosphate kinase;
- B) producing uridine 5'-diphospho-α-D-galactose from uridine monophosphate and D-galactose in the presence of the set of enzymes, polyphosphate, and adenosine triphosphate.

Thus, in one embodiment of the present invention the method for producing uridine 5'-diphospho-α-D-galactose comprises the following steps;
- A) providing a solution comprising
  - (i) uridine monophosphate and D-galactose;
  - (ii) polyphosphate, and adenosine triphosphate in a catalytic amount;
  - providing a set of enzymes comprising a glucose-1-phosphate uridylyltransferase, a galactokinase, a polyphosphate kinase, a uridine monophosphate kinase and a 1-domain polyphosphate kinase and/or a 2-domain polyphosphate kinase;
- B) producing uridine 5'-diphospho-α-D-galactose from uridine monophosphate and D-galactose in the presence of the set of enzymes, polyphosphate, and adenosine triphosphate.

Thus, in one embodiment of the present invention the method for producing uridine 5'-diphospho-α-D-galactose comprises the following steps;
- A) providing a solution comprising
  - (i) uridine monophosphate and D-galactose;
  - (ii) polyphosphate, and adenosine triphosphate in a catalytic amount;
  - providing a set of enzymes comprising a glucose-1-phosphate uridylyltransferase, a galactokinase, a polyphosphate kinase, a uridine monophosphate kinase, and a 1-domain polyphosphate kinase;
- B) producing uridine 5'-diphospho-α-D-galactose from uridine monophosphate and D-galactose in the presence of the set of enzymes, polyphosphate, and adenosine triphosphate.

Thus, in one embodiment of the present invention the method for producing uridine 5'-diphospho-α-D-galactose comprises the following steps;
- A) providing a solution comprising
  - (i) uridine monophosphate and D-galactose;
  - (ii) polyphosphate, and adenosine triphosphate in a catalytic amount;
  - providing a set of enzymes comprising a glucose-1-phosphate uridylyltransferase, a galactokinase, a polyphosphate kinase, a uridine monophosphate kinase, and a 2-domain polyphosphate kinase;

B) producing uridine 5'-diphospho-α-D-galactose from uridine monophosphate and D-galactose in the presence of the set of enzymes, polyphosphate, and adenosine triphosphate.

Thus, in one embodiment of the present invention the method for producing uridine 5'-diphospho-α-D-galactose comprises the following steps;
A) providing a solution comprising
  (i) uridine monophosphate and D-galactose;
  (ii) polyphosphate, and adenosine triphosphate in a catalytic amount;
  providing a set of enzymes comprising a glucose-1-phosphate uridylyltransferase, a galactokinase, a polyphosphate kinase, a uridine monophosphate kinase, a 1-domain polyphosphate kinase and a 2-domain polyphosphate kinase;
B) producing uridine 5'-diphospho-α-D-galactose from uridine monophosphate and D-galactose in the presence of the set of enzymes, polyphosphate, and adenosine triphosphate.

The term "catalytic amount" refers herein to a substoichiometric amount of ATP, i.e. an amount of ATP which is less than the amount of galactose used in the in inventive method. Preferably, a catalytic amount of ATP ranges from 0.000001 to 0.99 moles per mole D-galactose. More preferably, a catalytic amount of ATP ranges from 0.000001 to 0.95 moles per mole D-galactose. More preferably, a catalytic amount of ATP ranges from 0.000001 to 0.9 moles per mole D-galactose. More preferably, a catalytic amount of ATP ranges from 0.000005 to 0.5 moles per mole D-galactose, more preferably from 0.00001 to 0.1 moles per mole D-galactose, more preferably from 0.00001 to 0.05 moles per mole D-galactose, more preferably from 0.00001 to 0.01 moles per mole D-galactose, and most preferably from 0.00001 to 0.001 moles per mole D-galactose.

Thus, in one embodiment of the present invention the method for producing uridine 5'-diphospho-α-D-galactose comprises the following steps;
A) providing a solution comprising
  (i) uridine monophosphate and D-galactose;
  (ii) polyphosphate, and adenosine triphosphate;
  providing a set of enzymes comprising a glucose-1-phosphate uridylyltransferase, a galactokinase, a polyphosphate kinase, and a uridine monophosphate kinase;
B) producing uridine 5'-diphospho-α-D-galactose from uridine monophosphate and D-galactose in the presence of the set of enzymes, polyphosphate, and adenosine triphosphate,
wherein in step A) adenosine triphosphate is added in an amount of 0.000001 moles to 0.9 moles per mole D-galactose, more preferably in an amount of 0.000005 moles to 0.5 moles per mole D-galactose, more preferably in an amount of 0.00001 moles to 0.1 moles per mole D-galactose, more preferably in an amount of 0.00001 moles to 0.05 moles per mole D-galactose, more preferably in an amount of 0.00001 moles to 0.01 moles per mole D-galactose, and most preferably in an amount of 0.00001 moles to 0.001 moles per mole D-galactose.

Thus, in one embodiment of the present invention the method for producing uridine 5'-diphospho-α-D-galactose comprises the following steps;
A) providing a solution comprising
  (i) uridine monophosphate and D-galactose;
  (ii) polyphosphate, and adenosine triphosphate;
  providing a set of enzymes comprising a glucose-1-phosphate uridylyltransferase, a galactokinase, a polyphosphate kinase, a uridine monophosphate kinase, and a 1-domain polyphosphate kinase and/or a 2-domain polyphosphate kinase;
B) producing uridine 5'-diphospho-α-D-galactose from uridine monophosphate and D-galactose in the presence of the set of enzymes, polyphosphate, and adenosine triphosphate,
wherein in step A) adenosine triphosphate is added in an amount of 0.001 moles to 0.9 moles per mole D-galactose, more preferably in an amount of 0.002 moles to 0.8 moles per mole D-galactose, more preferably in an amount of 0.003 moles to 0.7 moles per mole D-galactose, more preferably in an amount of 0.003 moles to 0.5 moles per mole D-galactose, more preferably in an amount of 0.003 moles to 0.2 moles per mole D-galactose, more preferably in an amount of 0.003 moles to 0.1 moles per mole D-galactose, and most preferably in an amount of 0.005 moles to 0.05 moles per mole D-galactose.

Preferably, ATP is present in the solution provided in step A) in a concentration between 0.05 mM and 100 mM, more preferably between 0.1 mM and 90 mM, more preferably between 0.1 mM and 50 mM, more preferably between 0.2 mM and 20 mM, more preferably between 0.2 mM and 10 mM, more preferably between 0.2 mM and 5 mM, and most preferably between 0.5 mM and 3 mM. Thus, in one embodiment of the present invention the method for producing uridine 5'-diphospho-α-D-galactose comprises the following steps;
A) providing a solution comprising
  (i) uridine monophosphate and D-galactose;
  (ii) polyphosphate, and adenosine triphosphate;
  providing a set of enzymes comprising a glucose-1-phosphate uridylyltransferase, a galactokinase, a polyphosphate kinase, and a uridine monophosphate kinase;
B) producing uridine 5'-diphospho-α-D-galactose from uridine monophosphate and D-galactose in the presence of the set of enzymes, polyphosphate, and adenosine triphosphate,
wherein in step A) the concentration of adenosine triphosphate in the solution is in the range of 0.5 mM to 3 mM.

In an alternative embodiment, ADP or AMP can be used instead of ATP in the inventive methods described herein. ATP is generated from AMP or ADP and polyphosphate in situ, so that the production of UDP-galactose can be performed with ADP or AMP as starting materials as well. Thus, in one embodiment of the present invention the method for producing uridine 5'-diphospho-α-D-galactose comprises the following steps;
A) providing a solution comprising
  (i) uridine monophosphate and D-galactose;
  (ii) polyphosphate, and adenosine monophosphate;
  providing a set of enzymes comprising a glucose-1-phosphate uridylyltransferase, a galactokinase, a polyphosphate kinase, and a uridine monophosphate kinase;
B) producing uridine 5'-diphospho-α-D-galactose from uridine monophosphate and D-galactose in the presence of the set of enzymes, polyphosphate, and adenosine triphosphate.

In one embodiment of the present invention the method for producing uridine 5'-diphospho-α-D-galactose comprises the following steps;
A) providing a solution comprising
  (i) uridine monophosphate and D-galactose;
  (ii) polyphosphate, and adenosine diphosphate;

providing a set of enzymes comprising a glucose-1-phosphate uridylyltransferase, a galactokinase, a polyphosphate kinase, a and uridine monophosphate kinase;

B) producing uridine 5'-diphospho-α-D-galactose from uridine monophosphate and D-galactose in the presence of the set of enzymes, polyphosphate, and adenosine triphosphate.

In an alternative embodiment, ATP is used in excess of D-galactose in order to increase the space-time yield. Thus, in one embodiment of the present invention the method for producing uridine 5'-diphospho-α-D-galactose comprises the following steps;
A) providing a solution comprising
(i) uridine monophosphate and D-galactose;
(ii) polyphosphate, and adenosine triphosphate;
providing a set of enzymes comprising a glucose-1-phosphate uridylyltransferase, a galactokinase, a polyphosphate kinase, a uridine monophosphate kinase, and a 1-domain polyphosphate kinase and/or a 2-domain polyphosphate kinase;
B) producing uridine 5'-diphospho-α-D-galactose from uridine monophosphate and D-galactose in the presence of the set of enzymes, polyphosphate, and adenosine triphosphate;
wherein the amount of ATP ranges from 1 to 100 moles per mole D-galactose, more preferably the amount of ATP ranges from 1.2 to 50 moles per mole D-galactose, more preferably the amount of ATP ranges from 1.5 to 20 moles per mole D-galactose and most preferably the amount of ATP ranges from 2 to 10 moles per mole D-galactose Preferably, in the method of the present invention, the resulting solution in step A) has a pH value in a range of 5.0-10.0, preferred 5.5-9.5, more preferred 6.0-9.0, still more preferred 6.5-9.0, still more preferred 7.0-9.0 and most preferred a pH value in the range of 7.5 to 8.5.

Thus, in one embodiment of the present invention the method for producing uridine 5'-diphospho-α-D-galactose comprises the following steps;
A) providing a solution comprising
(i) uridine monophosphate and D-galactose;
(ii) polyphosphate, and adenosine diphosphate in a catalytic amount;
providing a set of enzymes comprising a glucose-1-phosphate uridylyltransferase, a galactokinase, a polyphosphate kinase, a and uridine monophosphate kinase;
B) producing uridine 5'-diphospho-α-D-galactose from uridine monophosphate and D-galactose in the presence of the set of enzymes, polyphosphate, and adenosine triphosphate, wherein the resulting solution in step A) has a pH value in the range of 7.5 to 8.5.

In one embodiment of the present invention the method for producing uridine 5'-diphospho-α-D-galactose comprises the following steps;
A) providing a solution comprising
(i) uridine monophosphate and D-galactose;
(ii) polyphosphate, and adenosine diphosphate in a catalytic amount;
providing a set of enzymes comprising a glucose-1-phosphate uridylyltransferase, a galactokinase, a polyphosphate kinase, a and uridine monophosphate kinase;
B) producing uridine 5'-diphospho-α-D-galactose from uridine monophosphate and D-galactose in the presence of the set of enzymes, polyphosphate, and adenosine triphosphate, wherein the resulting solution in step A) has a pH value of about 8.5.

In one embodiment of the present invention, the solution provided in step A) comprises $Mg^{2+}$ ions as cofactor for the catalytic activity of the set of enzymes. Preferably, $Mg^{2+}$ ions are present in the solution provided in step A) in a concentration between 1 mM and 200 mM, more preferably between 1 mM and 150 mM, more preferably between 2 mM and 150 mM, more preferably between 5 mM and 100 mM, more preferably between 10 mM and 90 mM, more preferably between 15 mM and 80 mM, more preferably between 20 mM and 80 mM and most preferably between 20 mM and 50 mM.

Thus, in one embodiment of the present invention the method for producing uridine 5'-diphospho-α-D-galactose comprises the following steps;
A) providing a solution comprising
(i) uridine monophosphate and D-galactose;
(ii) polyphosphate, and adenosine diphosphate in a catalytic amount;
providing a set of enzymes comprising a glucose-1-phosphate uridylyltransferase, a galactokinase, a polyphosphate kinase, a and uridine monophosphate kinase;
B) producing uridine 5'-diphospho-α-D-galactose from uridine monophosphate and D-galactose in the presence of the set of enzymes, polyphosphate, and adenosine triphosphate, wherein the resulting solution in step A) has a $Mg^{2+}$ concentration in the range of 20 mM and 80 mM, preferably between 20 mM and 50 mM.

The inventive method for producing UDP-galactose can also be carried out with a set of immobilized enzymes. The enzymes are then immobilized on a solid support such that they retain their activity, substrate specificity, stereoselectivity and/or other properties. Suitable solid supports are for instance beads, monoliths, spheres, particles, a particle bed, a fiber mat, granules, a gel, a membrane, a hollow-fiber membrane, a mixed-matrix membrane, a surface or other solid phase material.

In one embodiment, each enzyme, i.e. the glucose-1-phosphate uridylyltransferase, the galactokinase, the polyphosphate kinase, and the uridine monophosphate kinase, is immobilized on a solid support. In a further embodiment, each enzyme, i.e. the glucose-1-phosphate uridylyltransferase, the galactokinase, the polyphosphate kinase, the uridine monophosphate kinase, the 1-domain polyphosphate kinase and/or the 2-domain polyphosphate kinase and optionally the pyrophosphatase, is immobilized on a solid support.

In one embodiment, only some of the enzymes of the set of enzymes are immobilized on a solid support. In a further embodiment only one enzyme selected from the set of enzymes comprising a glucose-1-phosphate uridylyltransferase, a galactokinase, a polyphosphate kinase or a combination of polyphosphate kinases e.g. combination 1D- and 2D-ppk2 and ppk3, a uridine monophosphate kinase, and optionally a pyrophosphatase is immobilized on a solid support. In yet another embodiment, at least one enzyme selected from the set of enzymes comprising a glucose-1-phosphate uridylyltransferase, a galactokinase, a polyphosphate kinase, a uridine monophosphate kinase, and optionally a pyrophosphatase is immobilized on a solid support. Preferably, the polyphosphate kinase is immobilized on a solid support. Preferably, the glucose-1-phosphate uridylyltransferase is immobilized on a solid support. Preferably, the galactokinase is immobilized on a solid support. Preferably, the uridine monophosphate kinase is immobilized on a solid support. Preferably, the pyrophosphatase is immobilized on a solid support.

Thus, the present invention is also directed to a method for producing uridine 5'-diphospho-α-D-galactose comprising the following steps:
A) providing a solution comprising
(i) uridine monophosphate and D-galactose;
(ii) polyphosphate, and adenosine triphosphate;
providing a set of enzymes comprising a glucose-1-phosphate uridylyltransferase, a galactokinase, a polyphosphate kinase, and a uridine monophosphate kinase;
B) producing uridine 5'-diphospho-α-D-galactose from uridine monophosphate and D-galactose in the presence of the set of enzymes, polyphosphate, and adenosine triphosphate,
wherein the set of enzymes is bound or immobilized on a solid support.

Also, the present invention is also directed to a method for producing uridine 5'-diphospho-α-D-galactose comprising the following steps:
A) providing a solution comprising
(i) uridine monophosphate and D-galactose;
(ii) polyphosphate, and adenosine triphosphate;
providing a set of enzymes comprising a glucose-1-phosphate uridylyltransferase, a galactokinase, a polyphosphate kinase, a uridine monophosphate kinase, and a pyrophosphatase;
B) producing uridine 5'-diphospho-α-D-galactose from uridine monophosphate and D-galactose in the presence of the set of enzymes, polyphosphate, and adenosine triphosphate,
wherein the set of enzymes is bound or immobilized on a solid support.

Also, the present invention is also directed to a method for producing uridine 5'-diphospho-α-D-galactose comprising the following steps:
A) providing a solution comprising
(i) uridine monophosphate and D-galactose;
(ii) polyphosphate, and adenosine triphosphate;
providing a set of enzymes comprising a glucose-1-phosphate uridylyltransferase, a galactokinase, a polyphosphate kinase, a uridine monophosphate kinase, a 1-domain polyphosphate kinase and/or a 2-domain polyphosphate kinase, and optionally a pyrophosphatase;
B) producing uridine 5'-diphospho-α-D-galactose from uridine monophosphate and D-galactose in the presence of the set of enzymes, polyphosphate, and adenosine triphosphate,
wherein the set of enzymes is bound or immobilized on a solid support.

Also, the present invention is also directed to a method for producing uridine 5'-diphospho-α-D-galactose comprising the following steps:
A) providing a solution comprising
(i) uridine monophosphate and D-galactose;
(ii) polyphosphate, and adenosine triphosphate;
providing a set of enzymes comprising a glucose-1-phosphate uridylyltransferase, a galactokinase, a polyphosphate kinase, and a uridine monophosphate kinase;
B) producing uridine 5'-diphospho-α-D-galactose from uridine monophosphate and D-galactose in the presence of the set of enzymes, polyphosphate, and adenosine triphosphate,
wherein at least one enzyme of the set of enzymes is immobilized on a solid support.

Preferably the enzymes used in the inventive methods described herein are co-immobilized on a solid support. Immobilization of sequentially acting enzymes within a confined space increases catalytic efficiency of conversion due to dramatic reduction in the diffusion time of the substrate. In addition, the in-situ formation of substrates generates high local concentrations that lead to kinetic enhancements and can equate to substantial cost savings. Co-immobilization is usually achieved by mixing the enzymes prior immobilization on a solid support.

Thus, the present invention is also directed to a method for producing uridine 5'-diphospho-α-D-galactose comprising the following steps:
A) providing a solution comprising
(i) uridine monophosphate and D-galactose;
(ii) polyphosphate, and adenosine triphosphate;
providing a set of enzymes comprising a glucose-1-phosphate uridylyltransferase, a galactokinase, a polyphosphate kinase, and a uridine monophosphate kinase;
B) producing uridine 5'-diphospho-α-D-galactose from uridine monophosphate and D-galactose in the presence of the set of enzymes, polyphosphate, and adenosine triphosphate,
wherein the set of enzymes is co-immobilized on a solid support.

Also, the present invention is also directed to a method for producing uridine 5'-diphospho-α-D-galactose comprising the following steps:
A) providing a solution comprising
(i) uridine monophosphate and D-galactose;
(ii) polyphosphate, and adenosine triphosphate;
providing a set of enzymes comprising a glucose-1-phosphate uridylyltransferase, a galactokinase, a polyphosphate kinase, a uridine monophosphate kinase, and a pyrophosphatase;
B) producing uridine 5'-diphospho-α-D-galactose from uridine monophosphate and D-galactose in the presence of the set of enzymes, polyphosphate, and adenosine triphosphate,
wherein the set of enzymes is co-immobilized on a solid support.

Also, the present invention is also directed to a method for producing uridine 5'-diphospho-α-D-galactose comprising the following steps:
A) providing a solution comprising
(i) uridine monophosphate and D-galactose;
(ii) polyphosphate, and adenosine triphosphate;
providing a set of enzymes comprising a glucose-1-phosphate uridylyltransferase, a galactokinase, a polyphosphate kinase, a uridine monophosphate kinase, a 1-domain polyphosphate kinase and/or a 2-domain polyphosphate kinase, and optionally a pyrophosphatase;
B) producing uridine 5'-diphospho-α-D-galactose from uridine monophosphate and D-galactose in the presence of the set of enzymes, polyphosphate, and adenosine triphosphate,
wherein the set of enzymes is co-immobilized on a solid support.

The present invention is also directed to a method for producing uridine 5'-diphospho-α-D-galactose comprising the following steps:

A) providing a solution comprising
  (i) uridine monophosphate and D-galactose;
  (ii) polyphosphate, and adenosine triphosphate;
  providing a set of enzymes co-immobilized on a solid support comprising a glucose-1-phosphate uridylyltransferase, a galactokinase, a polyphosphate kinase, and a uridine monophosphate kinase;
B) producing uridine 5′-diphospho-α-D-galactose from uridine monophosphate and D-galactose in the presence of the set of enzymes, polyphosphate, and adenosine triphosphate.

Preferably, the method for producing uridine 5′-diphospho-α-D-galactose comprises the following steps:
A) providing a solution comprising
  (i) uridine monophosphate and D-galactose;
  (ii) polyphosphate, and adenosine triphosphate;
  providing a set of enzymes co-immobilized on a solid support comprising a glucose-1-phosphate uridylyltransferase, a galactokinase, a polyphosphate kinase, and a uridine monophosphate kinase;
B) producing uridine 5′-diphospho-α-D-galactose from uridine monophosphate and D-galactose in the presence of the set of enzymes, polyphosphate, and adenosine triphosphate,
wherein the solid support has the form of beads, monoliths, spheres, particles, a particle bed, a fiber mat, granules, a gel, a membrane, a hollow-fiber membrane, a mixed-matrix membrane or a surface. Preferably, the solid support has the form of beads.

In such embodiments, the immobilized enzymes can facilitate the production of uridine 5′-diphospho-α-D-galactose from UMP and D-galactose, and after the reaction is completed the immobilized enzymes are easily retained (e.g., by retaining beads on which the enzymes are immobilized) and then reused or recycled in subsequent runs. Such immobilized biocatalytic processes allow for further efficiency and cost reduction. In addition, the inventive method can be conducted in a continuous manner by passing the feed solution of step A) through a reactor containing the set of enzymes immobilized on a solid support.

Thus, in one embodiment, the method for producing uridine 5′-diphospho-α-D-galactose comprises the following steps:
A) providing a feed solution comprising
  (i) uridine monophosphate and D-galactose;
  (ii) polyphosphate, and adenosine triphosphate;
  providing a set of enzymes co-immobilized on a solid support comprising a glucose-1-phosphate uridylyltransferase, a galactokinase, a polyphosphate kinase, and a uridine monophosphate kinase; wherein the solid support comprising the set of immobilized enzymes is located in a chemical reactor,
B) producing uridine 5′-diphospho-α-D-galactose from uridine monophosphate and D-galactose in the presence of the set of enzymes, polyphosphate, and adenosine triphosphate by continuously passing the feed solution from step A) through the chemical reactor loaded with the solid support comprising the set of immobilized enzymes.

Preferably, the method for producing uridine 5′-diphospho-α-D-galactose comprises the following steps:
A) providing a feed solution comprising
  (i) uridine monophosphate and D-galactose;
  (ii) polyphosphate, and adenosine triphosphate;
  providing a set of enzymes co-immobilized on a solid support comprising a glucose-1-phosphate uridylyltransferase, a galactokinase, a polyphosphate kinase, a uridine monophosphate kinase and a pyrophosphatase; wherein the solid support comprising the set of immobilized enzymes is located in a chemical reactor,
B) producing uridine 5′-diphospho-α-D-galactose from uridine monophosphate and D-galactose in the presence of the set of enzymes, polyphosphate, and adenosine triphosphate by continuously passing the feed solution from step A) through the chemical reactor loaded with the solid support comprising the set of immobilized enzymes.

Preferably, the method for producing uridine 5′-diphospho-α-D-galactose comprises the following steps:
A) providing a feed solution comprising
  (i) uridine monophosphate and D-galactose;
  (ii) polyphosphate, and adenosine triphosphate;
  providing a set of enzymes co-immobilized on a solid support comprising a glucose-1-phosphate uridylyltransferase, a galactokinase, a polyphosphate kinase, a uridine monophosphate kinase, a 1-domain polyphosphate kinase and/or a 2-domain polyphosphate kinase, and optionally a pyrophosphatase; wherein the solid support comprising the set of immobilized enzymes is located in a chemical reactor,
B) producing uridine 5′-diphospho-α-D-galactose from uridine monophosphate and D-galactose in the presence of the set of enzymes, polyphosphate, and adenosine triphosphate by continuously passing the feed solution from step A) through the chemical reactor loaded with the solid support comprising the set of immobilized enzymes.

Methods of enzyme immobilization are well-known in the art. The enzymes can be bound non-covalently or covalently, such as adsorption, covalent binding, ionic binding, metal binding, crosslinking or crystallization. Various methods for conjugation and immobilization of enzymes to solid supports (e.g., resins, membranes, beads, glass, etc.) are well known in the art and described in e.g.: Yi et al., Process Biochemistry 2007, 42, 895; Martin et al., Applied Microbiology and Biotechnology 2007, 76, 843; Koszelewski et al., Journal of Molecular Catalysis B: Enzymatic, 2010, 63, 39; Truppo et al., Org. Process Res. Dev., 2011, 15, 1033; Mateo et al., Biotechnology Progress, 2002, 18, 629. Preferably, the enzymes used in the inventive methods for producing uridine 5′-diphospho-α-D-galactose are covalently bound to the solid support.

The enzymes used in the inventive methods described herein, namely glucose-1-phosphate uridylyltransferase, galactokinase, polyphosphate kinase, uridine monophosphate kinase, 1-domain polyphosphate kinase, 2-domain polyphosphate kinase, and pyrophosphatase are well known to the skilled person and can be obtained by any method well known to the skilled person in the art. Particularly, the enzymes can be overexpressed in, isolated from or prepared by recombinant methods from microbiological cultures comprising bacterial cultures, such as E. coli, virus and phage cultures and eukaryotic cell cultures. The inventive methods described herein are not restricted to enzymes from the sources described in the experimental section. Thus, the inventive method can be performed with the above listed enzymes obtained from various sources using common protein expression or isolation techniques. Further, it is well known to the skilled person to adapt the preparation of the enzymes to the specific applications in which the method is used. For instance, the above listed enzymes can be expressed in *E. coli* by using bacterial growth media of non-animal origin, such as a Luria-Bertani broth comprising tryptone from soy.

In one embodiment the glucose-1-phosphate uridylyltransferase comprises an amino acid sequence as set forth in SEQ ID NO: 4, or an amino acid sequence having at least 80% sequence identity to said sequence. In one embodiment the galactokinase comprises an amino acid sequence as set forth in SEQ ID NO: 1, or an amino acid sequence having at least 80% sequence identity to said sequence. In one embodiment the polyphosphate kinase comprises an amino acid sequence as set forth in SEQ ID NO: 3, or an amino acid sequence having at least 80% sequence identity to said sequence. In one embodiment the uridine monophosphate kinase comprises an amino acid sequence as set forth in SEQ ID NO: 2, or an amino acid sequence having at least 80% sequence identity to said sequence. In one embodiment the 1-domain polyphosphate kinase comprises an amino acid sequence as set forth in SEQ ID NO: 6, or an amino acid sequence having at least 80% sequence identity to said sequence. In one embodiment the 2-domain polyphosphate kinase comprises an amino acid sequence as set forth in SEQ ID NO: 7, or an amino acid sequence having at least 80% sequence identity to said sequence. In one embodiment the pyrophosphatase comprises an amino acid sequence as set forth in SEQ ID NO: 5, or an amino acid sequence having at least 80% sequence identity to said sequence.

Thus, in one embodiment the method for producing uridine 5'-diphospho-α-D-galactose comprises the following steps:
A) providing a solution comprising
  (i) uridine monophosphate and D-galactose
  (ii) polyphosphate, and adenosine triphosphate; and
  providing a set of enzymes comprising a glucose-1-phosphate uridylyltransferase, a galactokinase, a polyphosphate kinase, and a uridine monophosphate kinase;
B) producing uridine 5'-diphospho-α-d-galactose from uridine monophosphate and d-galactose in the presence of the set of enzymes, polyphosphate, and adenosine triphosphate;
wherein the glucose-1-phosphate uridylyltransferase comprises an amino acid sequence as set forth in SEQ ID NO: 4, or an amino acid sequence having at least 80% sequence identity to said sequence; wherein the galactokinase comprises an amino acid sequence as set forth in SEQ ID NO: 1, or an amino acid sequence having at least 80% sequence identity to said sequence; wherein the polyphosphate kinase comprises an amino acid sequence as set forth in SEQ ID NO: 3, or an amino acid sequence having at least 80% sequence identity to said sequence; wherein the uridine monophosphate kinase comprises an amino acid sequence as set forth in SEQ ID NO: 2, or an amino acid sequence having at least 80% sequence identity to said sequence; wherein the 1-domain polyphosphate kinase comprises an amino acid sequence as set forth in SEQ ID NO: 6, or an amino acid sequence having at least 80% sequence identity to said sequence; wherein the 2-domain polyphosphate kinase comprises an amino acid sequence as set forth in SEQ ID NO: 7, or an amino acid sequence having at least 80% sequence identity to said sequence; and wherein the pyrophosphatase comprises an amino acid sequence as set forth in SEQ ID NO: 5, or an amino acid sequence having at least 80% sequence identity to said sequence.

The enzyme-containing solutions obtained from fermentation process, cell homogenization or cell lysis, which are usually centrifuged and filtered to remove cell debris, can be directly used for immobilizing the enzymes on a solid support. Thus, no further purification step or isolation step is required and the fermentation broth, (crude or purified) cell lysate or cell homogenate can be used for immobilizing the enzymes on a solid support such that they retain their activity, substrate specificity, stereoselectivity and/or other properties.

Thus, the present invention is further directed to a method for producing uridine 5'-diphospho-α-D-galactose comprising the following steps:
A) providing a solution comprising
  (i) uridine monophosphate and D-galactose;
  (ii) polyphosphate, and adenosine triphosphate; and
  providing a set of enzymes immobilized on a solid support comprising a glucose-1-phosphate uridylyltransferase, a galactokinase, a polyphosphate kinase, and a uridine monophosphate kinase;
B) producing uridine 5'-diphospho-α-D-galactose from uridine monophosphate and D-galactose in the presence of the set of enzymes, polyphosphate, and adenosine triphosphate;
wherein the set of enzymes is immobilized on a solid support from fermentation broth, crude cell lysate, purified cell lysate or cell homogenate.

Preferably, the method for producing uridine 5'-diphospho-α-D-galactose comprises the following steps:
A) providing a solution comprising
  (i) uridine monophosphate and D-galactose;
  (ii) polyphosphate, and adenosine triphosphate; and
  providing a set of enzymes immobilized on a solid support comprising a glucose-1-phosphate uridylyltransferase, a galactokinase, a polyphosphate kinase, and a uridine monophosphate kinase;
B) producing uridine 5'-diphospho-α-D-galactose from uridine monophosphate and D-galactose in the presence of the set of enzymes, polyphosphate, and adenosine triphosphate;
wherein the set of enzymes is immobilized directly on a solid support from crude cell lysate or cell homogenate.

Preferably, the method for producing uridine 5'-diphospho-α-D-galactose comprises the following steps:
A) providing a solution comprising
  (i) uridine monophosphate and D-galactose;
  (ii) polyphosphate, and adenosine triphosphate; and
  providing a set of enzymes immobilized on a solid support comprising a glucose-1-phosphate uridylyltransferase, a galactokinase, a polyphosphate kinase, and a uridine monophosphate kinase;
B) producing uridine 5'-diphospho-α-D-galactose from uridine monophosphate and D-galactose in the presence of the set of enzymes, polyphosphate, and adenosine triphosphate;
wherein the set of enzymes is immobilized directly on a solid support from fermentation broth without prior purification.

Reworded, the method for producing uridine 5'-diphospho-α-D-galactose comprises the following steps:
A) providing a solution comprising
  (i) uridine monophosphate and D-galactose;
  (ii) polyphosphate, and adenosine triphosphate; and
  providing a set of enzymes immobilized on a solid support comprising a glucose-1-phosphate uridylyltransferase, a galactokinase, a polyphosphate kinase, and a uridine monophosphate kinase;

B) producing uridine 5'-diphospho-α-D-galactose from uridine monophosphate and D-galactose in the presence of the set of enzymes, polyphosphate, and adenosine triphosphate;

wherein the set of enzymes is immobilized directly on a solid support from fermentation supernatant without prior purification.

Preferably, the method for producing uridine 5'-diphospho-α-D-galactose comprises the following steps:
A) providing a solution comprising
  (i) uridine monophosphate and D-galactose;
  (ii) polyphosphate, and adenosine triphosphate; and
  providing a set of enzymes immobilized on a solid support comprising a glucose-1-phosphate uridylyltransferase, a galactokinase, a polyphosphate kinase, and a uridine monophosphate kinase;
B) producing uridine 5'-diphospho-α-D-galactose from uridine monophosphate and D-galactose in the presence of the set of enzymes, polyphosphate, and adenosine triphosphate;

wherein the set of enzymes is co-immobilized on a solid support from fermentation broth, crude cell lysate, purified cell lysate or cell homogenate.

Preferably, the method for producing uridine 5'-diphospho-α-D-galactose comprises the following steps:
A) providing a solution comprising
  (i) uridine monophosphate and D-galactose;
  (ii) polyphosphate, and adenosine triphosphate; and
  providing a set of enzymes immobilized on a solid support comprising a glucose-1-phosphate uridylyltransferase, a galactokinase, a polyphosphate kinase, a pyrophosphatase and a uridine monophosphate kinase;
B) producing uridine 5'-diphospho-α-D-galactose from uridine monophosphate and D-galactose in the presence of the set of enzymes, polyphosphate, and adenosine triphosphate;

wherein the set of enzymes is co-immobilized on a solid support from fermentation broth, crude cell lysate, purified cell lysate or cell homogenate.

Preferably, the method for producing uridine 5'-diphospho-α-D-galactose comprises the following steps:
A) providing a solution comprising
  (i) uridine monophosphate and D-galactose;
  (ii) polyphosphate, and adenosine triphosphate; and
  providing a set of enzymes immobilized on a solid support comprising a glucose-1-phosphate uridylyltransferase, a galactokinase, a polyphosphate kinase, a uridine monophosphate kinase, a 1-domain polyphosphate kinase and/or a 2-domain polyphosphate kinase, and optionally a pyrophosphatase;
B) producing uridine 5'-diphospho-α-D-galactose from uridine monophosphate and D-galactose in the presence of the set of enzymes, polyphosphate, and adenosine triphosphate;

wherein the set of enzymes is co-immobilized on a solid support from fermentation broth, crude cell lysate, purified cell lysate or cell homogenate.

Preferably, the method for producing uridine 5'-diphospho-α-D-galactose comprises the following steps:
A) providing a solution comprising
  (i) uridine monophosphate and D-galactose;
  (ii) polyphosphate, and adenosine triphosphate; and
  providing a set of enzymes comprising a glucose-1-phosphate uridylyltransferase, a galactokinase, a polyphosphate kinase, and a uridine monophosphate kinase;
B) producing uridine 5'-diphospho-α-D-galactose from uridine monophosphate and D-galactose in the presence of the set of enzymes, polyphosphate, and adenosine triphosphate;

wherein at least one enzyme of the set of enzymes is co-immobilized on a solid support from fermentation broth, crude cell lysate, purified cell lysate or cell homogenate.

Preferably, the method for producing uridine 5'-diphospho-α-D-galactose comprises the following steps:
A) providing a solution comprising
  (i) uridine monophosphate and D-galactose;
  (ii) polyphosphate, and adenosine triphosphate; and
  providing a set of enzymes comprising a glucose-1-phosphate uridylyltransferase, a galactokinase, a polyphosphate kinase, a pyrophosphatase and a uridine monophosphate kinase;
B) producing uridine 5'-diphospho-α-D-galactose from uridine monophosphate and D-galactose in the presence of the set of enzymes, polyphosphate, and adenosine triphosphate;

wherein at least one enzyme of the set of enzymes is co-immobilized on a solid support from fermentation broth, crude cell lysate, purified cell lysate or cell homogenate.

Preferably, the method for producing uridine 5'-diphospho-α-D-galactose comprises the following steps:
A) providing a solution comprising
  (i) uridine monophosphate and D-galactose;
  (ii) polyphosphate, and adenosine triphosphate; and
  providing a set of enzymes comprising a glucose-1-phosphate uridylyltransferase, a galactokinase, a polyphosphate kinase, a uridine monophosphate kinase, a 1-domain polyphosphate kinase and/or a 2-domain polyphosphate kinase, and optionally a pyrophosphatase;
B) producing uridine 5'-diphospho-α-D-galactose from uridine monophosphate and D-galactose in the presence of the set of enzymes, polyphosphate, and adenosine triphosphate;

wherein at least one enzyme of the set of enzymes is co-immobilized on a solid support from fermentation broth, crude cell lysate, purified cell lysate or cell homogenate.

Solid supports useful for immobilizing the enzymes used in the method of the present invention include but are not limited to beads or resins comprising polymethacrylate with epoxide functional groups, polymethacrylate with epoxide functional groups, polymethacrylate with amino epoxide functional groups, polymethacrylate with ethylenediamine functional groups, polyacrylic acid with epoxy functional groups, polyacrylic acid with anionic/amino C6 spacer functional groups, polyacrylic acid with anionic/tertiary amine functional groups, polystyrene with anionic/quaternary amine functional groups, polystyrene with cationic/sulphonic functional groups, polyacrylic acid with carboxylic ester functional groups, polystyrene with phenyl functional groups, polymethacrylate with octadecyl functional groups, polystyrene with styrene/methyl functional groups, magnetic silica particles with Ni-NTA functional group, or magnetic nanoparticles with a core of magnetite and a dextran shell with Ni-NTA functional group. While, in principle, any suitable solid support known in the art can be used in the inventive method, Ni agarose beads or Ni NTA agarose resins are not preferred for the reasons as set forth above.

Exemplary solid supports useful for immobilizing the enzymes used in the inventive method include, but are not limited to, sepabeads (Resindion): EC-EP, including EC-EP/S and EC-EP/M, EP112/S, EP112/M, EP113/S, EP113/

M, EP403/M, EP403/S, EC-HFA/M, EC-HFA/S, HFA403/M, HFA403/S, EC-EA/M, EC-EA/S, EP400/SS and EC-HA; including EC-HA/S and EC-HA/M, relizyme (Resindion) EA403/S; immobeads (ChiralVision) Imm150P, IB-COV1, IB-COV2, IB-COV3, IB-ANI1, IB-ANI2, IB-ANI3, IB-ANI4, IB-CAT1, IB-ADS1, IB-ADS2, IB-ADS3 and IB-ADS4; Eupergit (Röhm GmbH & Co. KG); Lifetech™ (Purolite) ECR8215F, ECR8204F, ECR8209F, ECR8285, ECR8409F, ECR8315F, ECR8309F, ECR1030F, 8806F, 8415F, 1091M, 1604; and magnetic particles (micromod GmbH): Nano-mag-D and Sicastar-M-CT.

Preferably, the solid support is composed of a resin or beads selected from: sepabeads (Resindion): EC-EP, EC-EP/S, EC-EP/M, EP112/S, EP112/M, EP113/S, EP113/M, EP403/M, EP403/S, EC-HFA/M, EC-HFA/S, HFA403/M, HFA403/S, EC-EA/M, EC-EA/S, EP400/SS and EC-HA; EC-HA/S, EC-HA/M, relizyme (Resindion) EA403/S; immobeads (ChiralVision) Imm150P, IB-COV1, IB-COV2, IB-COV3, IB-ANI1, IB-ANI2, IB-ANI3, IB-ANI4, IB-CAT1, IB-ADS1, IB-ADS2, IB-ADS3 and IB-ADS4; Eupergit (Röhm GmbH & Co. KG); Lifetech™ (Purolite) ECR8215F, ECR8204F, ECR8209F, ECR8285, ECR8409F, ECR8315F, ECR8309F, ECR1030F, 8806F, 8415F, 1091M, 1604; and magnetic particles (micromod GmbH): Nano-mag-D and Sicastar-M-CT.

More preferably, the solid support is composed of a resin or beads selected from: EC-EP, EP403/M, IB-COV1, IB-COV2, IB-COV3, Eupergit® CM, ECR8215F, ECR8204F, ECR8209F, ECR8285, EP403/S, and EP400/SS.

Thus, the present invention is further directed to a method for producing uridine 5'-diphospho-α-D-galactose comprising the following steps:
  A) providing a solution comprising
    (i) uridine monophosphate and D-galactose;
    (ii) polyphosphate, and adenosine triphosphate;
    providing a set of enzymes immobilized on a solid support comprising a glucose-1-phosphate uridylyltransferase, a galactokinase, a polyphosphate kinase, and a uridine monophosphate kinase;
  B) producing uridine 5'-diphospho-α-D-galactose from uridine monophosphate and D-galactose in the presence of the set of enzymes, polyphosphate, and adenosine triphosphate,
wherein the solid support is composed of a resin or beads selected from: EC-EP, EP403/M, IB-COV1, IB-COV2, IB-COV3, Eupergit® CM, ECR8215F, ECR8204F, ECR8209F, ECR8285, EP403/S, and EP400/SS.

Preferably, the method for producing uridine 5'-diphospho-α-D-galactose comprises the following steps:
  A) providing a solution comprising
    (i) uridine monophosphate and D-galactose;
    (ii) polyphosphate, and adenosine triphosphate;
    providing a set of enzymes immobilized on a solid support comprising a glucose-1-phosphate uridylyltransferase, a galactokinase, a polyphosphate kinase, a pyrophosphatase, and a uridine monophosphate kinase;
  B) producing uridine 5'-diphospho-α-D-galactose from uridine monophosphate and D-galactose in the presence of the set of enzymes, polyphosphate, and adenosine triphosphate,
wherein the solid support is composed of a resin or beads selected from: EC-EP, EP403/M, IB-COV1, IB-COV2, IB-COV3, Eupergit® CM, ECR8215F, ECR8204F, ECR8209F, ECR8285, EP403/S, and EP400/SS.

Preferably, the method for producing uridine 5'-diphospho-α-D-galactose comprises the following steps:
  A) providing a solution comprising
    (i) uridine monophosphate and D-galactose;
    (ii) polyphosphate, and adenosine triphosphate;
    providing a set of enzymes immobilized on a solid support comprising a glucose-1-phosphate uridylyltransferase, a galactokinase, a polyphosphate kinase, a uridine monophosphate kinase, a 1-domain polyphosphate kinase and/or a 2-domain polyphosphate kinase, and optionally a pyrophosphatase;
  B) producing uridine 5'-diphospho-α-D-galactose from uridine monophosphate and D-galactose in the presence of the set of enzymes, polyphosphate, and adenosine triphosphate,
wherein the solid support is composed of a resin or beads selected from: EC-EP, EP403/M, IB-COV1, IB-COV2, IB-COV3, Eupergit® CM, ECR8215F, ECR8204F, ECR8209F, ECR8285, EP403/S, and EP400/SS.

Also, the present invention is directed to a method for producing uridine 5'-diphospho-α-D-galactose comprising the following steps:
  A) providing a solution comprising
    (i) uridine monophosphate and D-galactose;
    (ii) polyphosphate, and adenosine triphosphate;
    providing a set of enzymes immobilized on a solid support comprising a glucose-1-phosphate uridylyltransferase, a galactokinase, a polyphosphate kinase, a uridine monophosphate kinase, a 1-domain polyphosphate kinase and/or a 2-domain polyphosphate kinase, and optionally a pyrophosphatase;
  B) producing uridine 5'-diphospho-α-D-galactose from uridine monophosphate and D-galactose in the presence of the set of enzymes, polyphosphate, and adenosine triphosphate,
wherein the solid support is composed of beads or resins comprising polymethacrylate with epoxide functional groups, polymethacrylate with amino epoxide functional groups, polymethacrylate with ethylenediamine functional groups, polyacrylic acid with epoxy functional groups, polyacrylic acid with anionic/amino C6 spacer functional groups, polyacrylic acid with anionic/tertiary amine functional groups, polystyrene with anionic/quaternary amine functional groups, polystyrene with cationic/sulphonic functional groups, polyacrylic acid with carboxylic ester functional groups, polystyrene with phenyl functional groups, polymethacrylate with octadecyl functional groups, polystyrene with styrene/methyl functional groups, magnetic silica particles with Ni-NTA functional group, or magnetic nanoparticles with a core of magnetite and a dextran shell with Ni-NTA functional group.

In one embodiment, the enzymes are covalently immobilized on a solid support functionalized with epoxy groups as solid support. A solid support such as methacrylate polymer possesses a high mechanical strength which makes it suitable for use in reactors in multiple runs or cycles. The epoxy groups form very stable covalent bonds with the enzymes of the UDP-Gal cascade such that they retain their activity, substrate specificity, stereoselectivity and/or other properties, thereby minimizing the premature wash-off of the enzymes during synthesis.

Therefore, said solid support can be reused in multiple runs or cycles without loss of enzyme activity or without decrease in conversion or reaction yield (see FIG. 15). Thus, the inventors have shown that full conversion of D-galactose and UMP to UDP-galactose can be achieved even if the solid support on which the enzymes are covalently immobilized is reused in multiple cycles.

Preferably, the set of enzymes is co-immobilized on a reusable, mechanically stable solid support, thereby forming a robust solid enzyme preparation.

In the context of the present invention a reusable, mechanically stable solid support is a support which allows its multiple use within the inventive method for producing uridine 5'-diphospho-α-D-galactose, as well as other inventive methods described herein, such that all enzymes co-immobilized on the solid support retain large part of or increase their activity, substrate specificity, stereoselectivity and/or other properties, such that the enzymes are not washed off the solid support, and without significant degradation or abrasion of the solid support due to mechanical stress. Further, the enzymes can be co-immobilized directly from crude cell lysate or crude cell homogenate on the reusable, mechanically stable solid support and the solid support can be used in a large number of cycles (e.g. 20 batch cycles and more), or when the inventive methods described herein are run continuously, the reusable, mechanically stable solid support can be used over a prolonged time. The term "robust solid support" is used synonymously herein for a reusable, mechanically stable solid support that i) allows the co-immobilization of the set of enzymes from crude cell lysate or crude cell homogenate, ii) retains large parts of or increases the activity of all enzymes co-immobilized iii) allows the synthesis of the target product in a large number of cycles (e.g. 20 batch cycles and more), or when the inventive methods described herein are run continuously, the solid support can be used over a prolonged time.

Preferably, the reusable, mechanically stable solid supports can be used in at least 3 cycles, more preferably in at least 4 cycles, more preferably in at least 5 cycles, more preferably in at least 6 cycles, more preferably in at least 7 cycles, more preferably in at least 8 cycles, more preferably in at least 9 cycles, more preferably in at least 10 cycles, more preferably in at least 12 cycles, more preferably in at least 14 cycles, more preferably in at least 16 cycles, more preferably in at least 18 cycles, more preferably in at least 20 cycles, more preferably in at least 25 cycles, more preferably in at least 25 cycles, more preferably in at least 30 cycles, and most preferably in at least 50 cycles of the inventive method described herein.

Thus, a further aspect of the present invention is directed to a set of enzymes comprising a glucose-1-phosphate uridylyltransferase, a galactokinase, a polyphosphate kinase, and a uridine monophosphate kinase; wherein the set of enzymes is co-immobilized on a polymeric solid support having a backbone of high mechanical strength which is functionalized with epoxy groups. Preferably, the set of enzymes is co-immobilized on a methacrylate polymer functionalized with epoxy groups.

Preferably, the set of enzymes further comprises a pyrophosphatase. Preferably, the set of enzymes also comprises a 1-domain polyphosphate kinase and/or a 2-domain polyphosphate kinase. Preferably, the set of enzymes further comprises a pyrophosphatase and a 1-domain polyphosphate kinase and/or a 2-domain polyphosphate kinase.

Preferably, the solid support having a backbone of high mechanical strength has the form of beads. Preferably, the beads have a particle size in the range of 150 μm-300 μm. Preferably, the solid support is porous with a pore diameter between 600 Å-1200 Å. In one embodiment, the solid support is of low porosity having a pore diameter between 300 Å-600 Å. In one embodiment, the solid support is of low porosity having a pore diameter between 450 Å-650 Å. In one embodiment, the solid support is of high porosity having a pore diameter between 1200 Å-1800 Å. In one embodiment, the solid support is further functionalized with butyl groups.

Preferably, the solid support is a porous methacrylate polymer with a pore diameter between 600 Å-1200 Å. In one embodiment, the solid support is a methacrylate polymer of low porosity having a pore diameter between 300 Å-600 Å. In one embodiment, the solid support is a methacrylate polymer of low porosity having a pore diameter between 450 Å-650 Å. In one embodiment, the solid support is a methacrylate polymer of high porosity having a pore diameter between 1200 Å-1800 Å. In one embodiment, the methacrylate polymer is further functionalized with butyl groups.

Preferably, the methacrylate polymer functionalized with epoxy groups is selected from the group consisting of SEPABEADS EC-EP, RELIZYME EP403/M, SEPABEADS EC-HFA/M, RELIZYME HFA403/M, RELIZYME HFA403/S, SEPABEADS EC-HFA/S, RELIZYME EP403/S, RELISORB EP400/SS, Eupergit® CM, Lifetech™ ECR8215F, Lifetech™ ECR8204F, Lifetech™ ECR8209F, Lifetech™ ECR8285, Imm150P, IB-COV1, IB-COV2 and IB-COV3.

Thus, the present invention is also directed to a method for producing uridine 5'-diphospho-α-D-galactose comprising the following steps:
A) providing a solution comprising
  (i) uridine monophosphate and D-galactose;
  (ii) polyphosphate, and adenosine triphosphate;
  providing a set of enzymes comprising a glucose-1-phosphate uridylyltransferase, a galactokinase, a polyphosphate kinase, and a uridine monophosphate kinase;
B) producing uridine 5'-diphospho-α-D-galactose from uridine monophosphate and D-galactose in the presence of the set of enzymes, polyphosphate, and adenosine triphosphate,
wherein the set of enzymes is covalently immobilized on a solid support functionalized with epoxy groups. Preferably, the solid support is a methacrylate polymer functionalized with epoxy groups.

Also, the present invention is directed to a method for producing uridine 5'-diphospho-α-D-galactose comprising the following steps:
A) providing a solution comprising
  (i) uridine monophosphate and D-galactose;
  (ii) polyphosphate, and adenosine triphosphate;
  providing a set of enzymes comprising a glucose-1-phosphate uridylyltransferase, a galactokinase, a polyphosphate kinase, a uridine monophosphate kinase, and a pyrophosphatase;
B) producing uridine 5'-diphospho-α-D-galactose from uridine monophosphate and D-galactose in the presence of the set of enzymes, polyphosphate, and adenosine triphosphate,
wherein the set of enzymes is covalently immobilized on a solid support functionalized with epoxy groups. Preferably the solid support is a methacrylate polymer functionalized with epoxy groups.

Also, the present invention is directed to a method for producing uridine 5'-diphospho-α-D-galactose comprising the following steps:
A) providing a solution comprising
  (i) uridine monophosphate and D-galactose;
  (ii) polyphosphate, and adenosine triphosphate;
  providing a set of enzymes comprising a glucose-1-phosphate uridylyltransferase, a galactokinase, a polyphosphate kinase, a uridine monophosphate kinase, a 1-domain polyphosphate kinase and/or a 2-domain polyphosphate kinase, and optionally a pyrophosphatase;

B) producing uridine 5'-diphospho-α-D-galactose from uridine monophosphate and D-galactose in the presence of the set of enzymes, polyphosphate, and adenosine triphosphate, wherein the set of enzymes is covalently immobilized on a solid support functionalized with epoxy groups. Preferably the solid support is a methacrylate polymer functionalized with epoxy groups.

Preferably, the solid support has the form of beads. Preferably, the beads have a particle size in the range of 150 μm-300 μm. Preferably, the solid support is porous with a pore diameter between 600 Å-1200 Å. In one embodiment, the solid support is of low porosity having a pore diameter between 300 Å-600 Å. In one embodiment, the solid support is of low porosity having a pore diameter between 450 Å-650 Å. In one embodiment, the solid support is of high porosity having a pore diameter between 1200 Å-1800 Å. In one embodiment, the solid support is further functionalized with butyl groups.

Preferably, the solid support is a methacrylate polymer in form of beads. Preferably, the beads have a particle size in the range of 150 μm-300 μm. Preferably, the methacrylate polymer is porous with a pore diameter between 600 Å-1200 Å. In one embodiment, the methacrylate polymer is of low porosity having a pore diameter between 300 Å-600 Å. In one embodiment, the methacrylate polymer is of low porosity having a pore diameter between 450 Å-650 Å. In one embodiment, the methacrylate polymer is of high porosity having a pore diameter between 1200 Å-1800 Å. In one embodiment, the methacrylate polymer is further functionalized with butyl groups.

In a further embodiment of the present invention, the method for producing uridine 5'-diphospho-α-D-galactose comprises the additional step C):

C) isolating the uridine 5'-diphospho-α-D-galactose.

In a further embodiment of the present invention, the method for producing uridine 5'-diphospho-α-D-galactose comprises the additional step C):

C) isolating the uridine 5'-diphospho-α-D-galactose by ion exchange chromatography.

Thus, the present invention is further directed to a method for producing uridine 5'-diphospho-α-D-galactose comprising the following steps:

A) providing a solution comprising
   (i) uridine monophosphate and D-galactose;
   (ii) polyphosphate, and adenosine triphosphate;
   providing a set of enzymes comprising a glucose-1-phosphate uridylyltransferase, a galactokinase, a polyphosphate kinase, and a uridine monophosphate kinase;

B) producing uridine 5'-diphospho-α-D-galactose from uridine monophosphate and D-galactose in the presence of the set of enzymes, polyphosphate, and adenosine triphosphate, C) isolating the uridine 5'-diphospho-α-D-galactose.

Preferably, the set of enzymes further comprises a pyrophosphatase. Preferably, the set of enzymes further comprises a 1-domain polyphosphate kinase and/or a 2-domain polyphosphate kinase. Preferably, the set of enzymes further comprises a pyrophosphatase and a 1-domain polyphosphate kinase and/or a 2-domain polyphosphate kinase.

Thus, in one embodiment the method for producing uridine 5'-diphospho-α-D-galactose comprises the following steps:

A) providing a solution comprising
   (i) uridine monophosphate and D-galactose;
   (ii) polyphosphate, and adenosine triphosphate;
   providing a set of enzymes comprising a glucose-1-phosphate uridylyltransferase, a galactokinase, a polyphosphate kinase, and a uridine monophosphate kinase;

B) producing uridine 5'-diphospho-α-D-galactose from uridine monophosphate and D-galactose in the presence of the set of enzymes, polyphosphate, and adenosine triphosphate, C) isolating the uridine 5'-diphospho-α-D-galactose.

wherein the set of enzymes is immobilized or co-immobilized on a solid support.

In one embodiment the method for producing uridine 5'-diphospho-α-D-galactose comprises the following steps:

A) providing a solution comprising
   (i) uridine monophosphate and D-galactose;
   (ii) polyphosphate, and adenosine triphosphate;
   providing a set of enzymes comprising a glucose-1-phosphate uridylyltransferase, a galactokinase, a polyphosphate kinase, and a uridine monophosphate kinase;

B) producing uridine 5'-diphospho-α-D-galactose from uridine monophosphate and D-galactose in the presence of the set of enzymes, polyphosphate, and adenosine triphosphate, C) isolating the uridine 5'-diphospho-α-D-galactose.

wherein the set of enzymes is co-immobilized on a solid support from cell lysate.

Preferably, the polyphosphate is a long-chain polyphosphate having at least 25 phosphate residues.

Preferably, the concentration of UMP and D-galactose in the solution provided in step A) is in the range of 0.2 mM to 15,000 mM.

Preferably, the set of enzymes further comprises a pyrophosphatase. Preferably, the set of enzymes further comprises a 1-domain polyphosphate kinase and/or a 2-domain polyphosphate kinase. Preferably, the set of enzymes further comprises a pyrophosphatase and a 1-domain polyphosphate kinase and/or a 2-domain polyphosphate kinase.

In one embodiment of the present invention, uridine 5'-diphospho-α-D-galactose is produced from uridine and D-galactose. Thus, uridine monophosphate in step A) of the inventive methods is obtained from uridine, adenosine phosphate and a uridine kinase enzyme. Thus, the method for producing uridine 5'-diphospho-α-D-galactose comprises the following steps:

A) providing a solution comprising
   (i') uridine and D-galactose;
   (ii) polyphosphate, and adenosine triphosphate;
   providing a set of enzymes comprising a uridine kinase, a glucose-1-phosphate uridylyltransferase, a galactokinase, a polyphosphate kinase, and a uridine monophosphate kinase;

B) producing uridine 5'-diphospho-α-D-galactose from uridine and D-galactose in the presence of the set of enzymes, polyphosphate, and adenosine triphosphate.

Preferably, the set of enzymes further comprises a pyrophosphatase. Preferably, the set of enzymes further comprises a 1-domain polyphosphate kinase and/or a 2-domain polyphosphate kinase. Preferably, the set of enzymes further comprises a pyrophosphatase and a 1-domain polyphosphate kinase and/or a 2-domain polyphosphate kinase. Preferably, the set of enzymes is immobilized or co-immobilized on a solid support. Preferably, the set of enzymes is directly co-immobilized on a solid support from fermentation broth, crude cell lysate, purified cell lysate or cell homogenate.

Preferably, the concentration of uridine and D-galactose in the solution provided in step A) is in the range of 0.2 mM to 15,000 mM.

In one embodiment of the present invention, uridine 5'-diphospho-α-D-galactose is produced from uracil, 5-phospho-α-D-ribose 1-diphosphate (PRPP) and D-galactose. Thus, uridine monophosphate in step A) of the inventive methods is obtained from uracil, 5-phospho-α-D-ribose 1-diphosphate and a uracil phosphoribosyltransferase enzyme. Thus, the method for producing uridine 5'-diphospho-α-D-galactose comprises the following steps:
A) providing a solution comprising
(i') uracil, phospho-α-D-ribose 1-diphosphate, and D-galactose;
(ii) polyphosphate, and adenosine triphosphate;
providing a set of enzymes comprising a uracil phosphoribosyltransferase, a glucose-1-phosphate uridylyltransferase, a galactokinase, a polyphosphate kinase, and a uridine monophosphate kinase;
B) producing uridine 5'-diphospho-α-D-galactose from uridine monophosphate and D-galactose in the presence of the set of enzymes, polyphosphate, and adenosine triphosphate.

Preferably, the set of enzymes further comprises a pyrophosphatase. Preferably, the set of enzymes further comprises a 1-domain polyphosphate kinase and/or a 2-domain polyphosphate kinase. Preferably, the set of enzymes further comprises a pyrophosphatase and a 1-domain polyphosphate kinase and/or a 2-domain polyphosphate kinase. Preferably, the set of enzymes is immobilized or co-immobilized on a solid support.

In one embodiment of the present invention, uridine 5'-diphospho-α-D-galactose is produced from orotic acid, 5-phospho-α-D-ribose 1-diphosphate (PRPP) and D-galactose. Orotic acid is phosphorylated in the presence of an orotate phosphoribosyltransferase and the formed oritidine 5'-phosphate (OMP) is decarboxylated to uridine monophosphate by a UMP synthase. Thus, uridine monophosphate in step A) of the inventive methods is obtained from orotic acid, 5-phospho-α-D-ribose 1-diphosphate, an orotate phosphoribosyltransferase and a UMP synthase enzyme. Thus, the method for producing uridine 5'-diphospho-α-D-galactose comprises the following steps:
A) providing a solution comprising
(i') orotic acid, phospho-α-D-ribose 1-diphosphate, and D-galactose;
(ii) polyphosphate, and adenosine triphosphate;
providing a set of enzymes comprising an orotate phosphoribosyltransferase, a UMP synthase, a glucose-1-phosphate uridylyltransferase, a galactokinase, a polyphosphate kinase, and a uridine monophosphate kinase;
B) producing uridine 5'-diphospho-α-D-galactose from uridine monophosphate and D-galactose in the presence of the set of enzymes, polyphosphate, and adenosine triphosphate.

Preferably, the set of enzymes further comprises a pyrophosphatase. Preferably, the set of enzymes further comprises a 1-domain polyphosphate kinase and/or a 2-domain polyphosphate kinase. Preferably, the set of enzymes further comprises a pyrophosphatase and a 1-domain polyphosphate kinase and/or a 2-domain polyphosphate kinase. Preferably, the set of enzymes is immobilized or co-immobilized on a solid support.

Reworded, the method for producing uridine 5'-diphospho-α-D-galactose comprises the following steps:
A) providing a solution comprising
(i') uridine monophosphate, and D-galactose;
(ii) polyphosphate, and adenosine triphosphate;
providing a set of enzymes comprising a glucose-1-phosphate uridylyltransferase, a galactokinase, a polyphosphate kinase, and a uridine monophosphate kinase;
B) producing uridine 5'-diphospho-α-D-galactose from uridine monophosphate and D-galactose in the presence of the set of enzymes, polyphosphate, and adenosine triphosphate;
wherein uridine monophosphate in step A) is obtained from uridine, adenosine triphosphate and a uridine kinase; or uracil, 5-phospho-α-D-ribose 1-diphosphate and a uracil phosphoribosyltransferase.

Galactosylated Saccharide, Galactosylated Glycopeptide, Galactosylated Glycoprotein, Galactosylated Protein, Galactosylated Peptide, Galactosylated Bioconjugate or Galactosylated Small Molecule In a further aspect of the present invention the inventive methods described herein are useful for producing galactosylated saccharide, galactosylated glycopeptide, galactosylated glycoprotein galactosylated protein, galactosylated peptide or galactosylated small molecule.

Thus, in one embodiment of the present invention the method for producing a galactosylated saccharide, galactosylated glycopeptide, galactosylated glycoprotein, galactosylated protein, galactosylated peptide, galactosylated bioconjugate or galactosylated small molecule comprises the following steps:
A) providing a solution comprising
(i) uridine monophosphate and D-galactose;
(ii) polyphosphate, and adenosine triphosphate; and
providing a set of enzymes comprising a glucose-1-phosphate uridylyltransferase, a galactokinase, a polyphosphate kinase, and a uridine monophosphate kinase;
B) producing uridine 5'-diphospho-α-D-galactose from uridine monophosphate and D-galactose in the presence of the set of enzymes, polyphosphate, and adenosine triphosphate.
D) producing a galactosylated saccharide, galactosylated glycopeptide, galactosylated glycoprotein, galactosylated protein, galactosylated peptide, galactosylated bioconjugate or galactosylated small molecule from uridine 5'-diphospho-α-D-galactose and a saccharide, glycopeptide, glycoprotein, protein, peptide, bioconjugate or small molecule by forming an O-glycosidic bond between uridine 5'-diphospho-α-D-galactose and an available hydroxyl group of the saccharide, glycopeptide, glycoprotein, protein, peptide, bioconjugate or small molecule in the presence of a galactosyltransferase.

Thus, in one embodiment of the present invention the method for producing a galactosylated saccharide, galactosylated glycopeptide, galactosylated glycoprotein galactosylated protein, galactosylated peptide, galactosylated bioconjugate or galactosylated small molecule comprises the following steps:
A) providing a solution comprising
(i) uridine monophosphate and D-galactose;
(ii) polyphosphate, and adenosine triphosphate; and
providing a set of enzymes comprising a glucose-1-phosphate uridylyltransferase, a galactokinase, a polyphosphate kinase, a pyrophosphatase, and a uridine monophosphate kinase;
B) producing uridine 5'-diphospho-α-D-galactose from uridine monophosphate and D-galactose in the presence of the set of enzymes, polyphosphate, and adenosine triphosphate.
D) producing a galactosylated saccharide, galactosylated glycopeptide, galactosylated glycoprotein, galactosylated protein, galactosylated peptide, galactosylated bioconjugate or galactosylated small molecule from uridine 5'-diphospho-α-D-galactose and a saccharide, glycopeptide, glycoprotein, protein, peptide, bioconjugate or small molecule by forming an O-glycosidic bond between uridine 5'-diphospho-α-D-galactose and an available hydroxyl group of the saccharide, glycopeptide, glycoprotein, protein, peptide, bioconjugate or small molecule in the presence of a galactosyltransferase.

Thus, in one embodiment of the present invention the method for producing a galactosylated saccharide, galactosylated glycopeptide, galactosylated glycoprotein galactosylated protein, galactosylated peptide, galactosylated bioconjugate or galactosylated small molecule comprises the following steps:
A) providing a solution comprising
  (i) uridine and D-galactose;
  (ii) polyphosphate, and adenosine triphosphate; and
  providing a set of enzymes comprising a uridine kinase, a glucose-1-phosphate uridylyltransferase, a galactokinase, a polyphosphate kinase, a pyrophosphatase, and a uridine monophosphate kinase;
B) producing uridine 5'-diphospho-α-D-galactose from uridine and D-galactose in the presence of the set of enzymes, polyphosphate, and adenosine triphosphate.
D) producing a galactosylated saccharide, galactosylated glycopeptide, galactosylated glycoprotein, galactosylated protein, galactosylated peptide, galactosylated bioconjugate or galactosylated small molecule from uridine 5'-diphospho-α-D-galactose and a saccharide, glycopeptide, glycoprotein, protein, peptide, bioconjugate or small molecule by forming an O-glycosidic bond between uridine 5'-diphospho-α-D-galactose and an available hydroxyl group of the saccharide, glycopeptide, glycoprotein, protein, peptide, bioconjugate or small molecule in the presence of a galactosyltransferase.

in one embodiment of the present invention the method for producing a galactosylated saccharide, galactosylated glycopeptide, galactosylated glycoprotein galactosylated protein, galactosylated peptide, galactosylated bioconjugate or galactosylated small molecule comprises the following steps:
A) providing a solution comprising
  (i) uridine monophosphate and D-galactose;
  (ii) polyphosphate, and adenosine triphosphate; and
  providing a set of enzymes comprising a glucose-1-phosphate uridylyltransferase, a galactokinase, a polyphosphate kinase, a pyrophosphatase, and a uridine monophosphate kinase;
B) producing uridine 5'-diphospho-α-D-galactose from uridine monophosphate and D-galactose in the presence of the set of enzymes, polyphosphate, and adenosine triphosphate.
D) producing a galactosylated saccharide, galactosylated glycopeptide, galactosylated glycoprotein, galactosylated peptide, galactosylated bioconjugate or galactosylated small molecule from uridine 5'-diphospho-α-D-galactose and a saccharide, glycopeptide, glycoprotein, protein, peptide, bioconjugate or small molecule by forming an O-glycosidic bond between uridine 5'-diphospho-α-D-galactose and an available hydroxyl group of the saccharide, glycopeptide, glycoprotein, protein, peptide, bioconjugate or small molecule in the presence of a galactosyltransferase, wherein in step A) adenosine triphosphate is added in an amount of 0.001 moles to 0.9 moles per mole D-galactose, more preferably in an amount of 0.002 moles to 0.8 moles per mole D-galactose, more preferably in an amount of 0.003 moles to 0.7 moles per mole D-galactose, more preferably in an amount of 0.003 moles to 0.5 moles per mole D-galactose, more preferably in an amount of 0.003 moles to 0.2 moles per mole D-galactose, more preferably in an amount of 0.003 moles to 0.1 moles per mole D-galactose, and most preferably in an amount of 0.005 moles to 0.05 moles per mole D-galactose.

Thus, in one embodiment of the present invention the method for producing a galactosylated saccharide, galactosylated glycopeptide, galactosylated glycoprotein galactosylated protein, galactosylated peptide, galactosylated bioconjugate or galactosylated small molecule comprises the following steps:
A) providing a solution comprising
  (i) uridine monophosphate and D-galactose;
  (ii) polyphosphate, and adenosine triphosphate; and
  providing a set of enzymes comprising a glucose-1-phosphate uridylyltransferase, a galactokinase, a polyphosphate kinase, a uridine monophosphate kinase, a 1-domain polyphosphate kinase and/or a 2-domain polyphosphate kinase, and optionally a pyrophosphatase;
B) producing uridine 5'-diphospho-α-D-galactose from uridine monophosphate and D-galactose in the presence of the set of enzymes, polyphosphate, and adenosine triphosphate;
D) producing a galactosylated saccharide, galactosylated glycopeptide, galactosylated glycoprotein, galactosylated protein, galactosylated peptide, galactosylated bioconjugate or galactosylated small molecule from uridine 5'-diphospho-α-D-galactose and a saccharide, glycopeptide, glycoprotein, protein, peptide, bioconjugate or small molecule by forming an O-glycosidic bond between uridine 5'-diphospho-α-D-galactose and an available hydroxyl group of the saccharide, glycopeptide, glycoprotein, protein, peptide, bioconjugate or small molecule in the presence of a galactosyltransferase.

The galactosyltransferase catalyzes the reaction of UDP-galactose with an available hydroxyl group of a saccharide, glycopeptide, glycoprotein, protein, peptide, bioconjugate or small molecule, thereby forming a galactosylated saccharide, galactosylated glycopeptide, galactosylated glycoprotein, a galactosylated protein, a galactosylated peptide, galactosylated bioconjugate or a galactosylated small molecule and uridine diphosphate (UDP) as side product. UDP being an intermediate product formed in step B), specifically in step (b1) can then be reused or recycled.

Thus, in one embodiment of the present invention the method for producing a galactosylated saccharide, galactosylated glycopeptide, galactosylated glycoprotein galactosylated protein, galactosylated peptide, galactosylated bioconjugate or galactosylated small molecule comprises the following steps:

A) providing a solution comprising
  (i) uridine monophosphate and D-galactose;
  (ii) polyphosphate, and adenosine triphosphate;
  providing a set of enzymes comprising a glucose-1-phosphate uridylyltransferase, a galactokinase, a polyphosphate kinase, and a uridine monophosphate kinase;
B) producing uridine 5'-diphospho-α-D-galactose from uridine monophosphate and D-galactose in the presence of the set of enzymes, polyphosphate, and adenosine triphosphate by
  (a) forming galactose 1-phosphate (Gal-1-P) from D-galactose and adenosine triphosphate being catalyzed by a galactokinase,
  (b1) forming uridine diphosphate (UDP) from uridine monophosphate and adenosine triphosphate being catalyzed by a uridine monophosphate kinase;
  (b2) forming uridine triphosphate (UTP) from uridine diphosphate and polyphosphate being catalyzed by a polyphosphate kinase; and
  (c) reacting galactose 1-phosphate with uridine triphosphate to UDP-galactose in the presence of a glucose-1-phosphate uridylyltransferase;
D) producing a galactosylated saccharide, galactosylated glycopeptide, galactosylated glycoprotein, galactosylated protein, galactosylated peptide, galactosylated bioconjugate or galactosylated small molecule from uridine 5'-diphospho-α-D-galactose and a saccharide, glycopeptide, glycoprotein, protein, peptide, bioconjugate or small molecule by forming an O-glycosidic bond between uridine 5'-diphospho-α-D-galactose and an available hydroxyl group of the saccharide, glycopeptide, glycoprotein, protein, peptide, bioconjugate or small molecule in the presence of a galactosyltransferase; and
E) recycling the in-situ formed uridine diphosphate to form uridine triphosphate.

Thus, in one embodiment of the present invention the method for producing a galactosylated saccharide, galactosylated glycopeptide, galactosylated glycoprotein galactosylated protein, galactosylated peptide, galactosylated bioconjugate or galactosylated small molecule comprises the following steps:

A) providing a solution comprising
  (i) uridine monophosphate and D-galactose;
  (ii) polyphosphate, and adenosine triphosphate;
  providing a set of enzymes comprising a glucose-1-phosphate uridylyltransferase, a galactokinase, a polyphosphate kinase, and a uridine monophosphate kinase;
B) producing uridine 5'-diphospho-α-D-galactose from uridine monophosphate and D-galactose in the presence of the set of enzymes, polyphosphate, and adenosine triphosphate by
  (a) forming galactose 1-phosphate (Gal-1-P) from D-galactose and adenosine triphosphate being catalyzed by a galactokinase,
  (b1) forming uridine diphosphate (UDP) from uridine monophosphate and adenosine triphosphate being catalyzed by a uridine monophosphate kinase;
  (b2) forming uridine triphosphate (UTP) from uridine diphosphate and polyphosphate being catalyzed by a polyphosphate kinase; and
  (c') reacting galactose 1-phosphate with uridine triphosphate to UDP-galactose in the presence of a glucose-1-phosphate uridylyltransferase; and
  (c") converting pyrophosphate to phosphate in the presence of a pyrophosphatase;
D) producing a galactosylated saccharide, galactosylated glycopeptide, galactosylated glycoprotein, galactosylated protein, galactosylated peptide, galactosylated bioconjugate or galactosylated small molecule from uridine 5'-diphospho-α-D-galactose and a saccharide, glycopeptide, glycoprotein, protein, peptide, bioconjugate or small molecule by forming an O-glycosidic bond between uridine 5'-diphospho-α-D-galactose and an available hydroxyl group of the saccharide, glycopeptide, glycoprotein, protein, peptide, bioconjugate or small molecule in the presence of a galactosyltransferase; and
E) recycling the in-situ formed uridine diphosphate to form uridine triphosphate.

Due to the recycling of the by-product uridine diphosphate in the inventive galactosylation methods described herein, lower amounts of UMP are required in the solution provided in step A). Thus, in one embodiment, the molar ratio of UMP to D-galactose is between 0.0001 and 0.999, more preferably between 0.0005 and 0.995, more preferably between 0.001 and 0.995, more preferably between 0.002 and 0.99 and most preferably between 0.005 and 0.98. In one embodiment, the molar ratio of UMP to D-galactose is 0.05. In one embodiment, the molar ratio of UMP to D-galactose is 0.1. In one embodiment, the molar ratio of UMP to D-galactose is 0.2. In one embodiment, the molar ratio of UMP to D-galactose is 0.5.

In another embodiment, the molar ratio of UMP to D-galactose is between 1 and 10, more preferably between 1.2 and 8, more preferably between 1.5 and 7, more preferably between 1.6 and 6 and most preferably between 2 and 5. In one embodiment, the molar ratio of UMP to D-galactose is 1.5. In one embodiment, the molar ratio of UMP to D-galactose is 2. In one embodiment, the molar ratio of UMP to D-galactose is 5. In one embodiment, the molar ratio of UMP to D-galactose is 10.

Preferably, the method for producing a galactosylated saccharide, a galactosylated glycopeptide, a galactosylated glycoprotein, a galactosylated protein, a galactosylated peptide, a galactosylated bioconjugate or a galactosylated small molecule comprises the following steps:

A) providing a solution comprising
  (i) uridine monophosphate and D-galactose;
  (ii) polyphosphate, and adenosine triphosphate; and
  providing a set of enzymes comprising a glucose-1-phosphate uridylyltransferase, a galactokinase, a polyphosphate kinase, and a uridine monophosphate kinase;
B) producing uridine 5'-diphospho-α-D-galactose from uridine monophosphate and D-galactose in the presence of the set of enzymes, polyphosphate, and adenosine triphosphate;
D) producing a galactosylated saccharide, galactosylated glycopeptide, galactosylated glycoprotein, galactosylated protein, galactosylated peptide, galactosylated bioconjugate or galactosylated small molecule from uridine 5'-diphospho-α-D-galactose and a saccharide, glycopeptide, glycoprotein, protein, peptide, biomolecule or small molecule by forming an O-glycosidic bond between uridine 5'-diphospho-α-D-galactose and an available hydroxyl group of the saccharide, glycopeptide, glycoprotein, protein, peptide, biomolecule or small molecule in the presence of a galactosyltransferase, F) isolating the galactosylated saccharide, galactosylated glycopeptide, galactosylated glycoprotein, galactosylated protein, galactosylated peptide, galactosylated bioconjugate or galactosylated small molecule.

Preferably, the method for producing a galactosylated saccharide, a galactosylated glycopeptide, a galactosylated glycoprotein, a galactosylated protein, a galactosylated peptide, a galactosylated bioconjugate or a galactosylated small molecule comprises the following steps:
  A) providing a solution comprising
    (i) uridine monophosphate and D-galactose;
    (ii) polyphosphate, and adenosine triphosphate; and
    providing a set of enzymes comprising a glucose-1-phosphate uridylyltransferase, a galactokinase, a polyphosphate kinase, a uridine monophosphate kinase, a 1-domain polyphosphate kinase and/or a 2-domain polyphosphate kinase, and optionally a pyrophosphatase;
  B) producing uridine 5'-diphospho-α-D-galactose from uridine monophosphate and D-galactose in the presence of the set of enzymes, polyphosphate, and adenosine triphosphate;
  D) producing a galactosylated saccharide, galactosylated glycopeptide, galactosylated glycoprotein, galactosylated protein, galactosylated peptide, galactosylated bioconjugate or galactosylated small molecule from uridine 5'-diphospho-α-D-galactose and a saccharide, glycopeptide, glycoprotein, protein, peptide, bioconjugate or small molecule by forming an O-glycosidic bond between uridine 5'-diphospho-α-D-galactose and an available hydroxyl group of the saccharide, glycopeptide, glycoprotein, protein, peptide, bioconjugate or small molecule in the presence of a galactosyltransferase,
  F) isolating the galactosylated saccharide, galactosylated glycopeptide, galactosylated glycoprotein, galactosylated protein, galactosylated peptide, galactosylated bioconjugate or galactosylated small molecule.

Preferably, the method for producing a galactosylated saccharide, a galactosylated glycopeptide, a galactosylated glycoprotein, a galactosylated protein, a galactosylated peptide, a galactosylated bioconjugate or a galactosylated small molecule comprises the following steps:
  A) providing a solution comprising
    (i) uridine monophosphate and D-galactose;
    (ii) polyphosphate, and adenosine triphosphate; and
    providing a set of enzymes comprising a glucose-1-phosphate uridylyltransferase, a galactokinase, a polyphosphate kinase, a uridine monophosphate kinase, a 1-domain polyphosphate kinase and/or a 2-domain polyphosphate kinase, and optionally a pyrophosphatase;
  B) producing uridine 5'-diphospho-α-D-galactose from uridine monophosphate and D-galactose in the presence of the set of enzymes, polyphosphate, and adenosine triphosphate;
  C) isolating the uridine 5'-diphospho-α-D-galactose; and
  D) producing a galactosylated saccharide, galactosylated glycopeptide, galactosylated glycoprotein, galactosylated protein, galactosylated peptide, galactosylated bioconjugate or galactosylated small molecule from uridine 5'-diphospho-α-D-galactose and a saccharide, glycopeptide, glycoprotein, protein, peptide, bioconjugate or small molecule by forming an O-glycosidic bond between uridine 5'-diphospho-α-D-galactose and an available hydroxyl group of the saccharide, glycopeptide, glycoprotein, protein, peptide, bioconjugate or small molecule in the presence of a galactosyltransferase,
  F) isolating the galactosylated saccharide, galactosylated glycopeptide, galactosylated glycoprotein, galactosylated protein, galactosylated peptide, galactosylated bioconjugate or galactosylated small molecule.

Preferably, the polyphosphate is a long-chain polyphosphate having at least 25 phosphate residues.

Preferably, the concentration of UMP and D-galactose in the solution provided in step A) is in the range of 0.02 mM to 50,000 mM. More preferably, the concentration of UMP and D-galactose is in the range of 0.2 mM to 15,000 mM.

Preferably, the concentration of the enzymes in the set of enzymes is between 0.0001 mg/mL and 100 mg/mL based on the total volume of the solution provided in step A).

Preferably, ATP is present in the solution provided in step A) in a concentration between 0.05 mM and 100 mM, more preferably between 0.1 mM and 90 mM, more preferably between 0.1 mM and 50 mM, more preferably between 0.2 mM and 20 mM, more preferably between 0.2 mM and 10 mM, more preferably between 0.2 mM and 5 mM, and most preferably between 0.5 mM and 3 mM.

Preferably, the resulting solution in step A) has a pH value in a range of 5.0-10.0, preferred 5.5-9.5, more preferred 6.0-9.0, still more preferred 6.5-9.0, still more preferred 7.0-9.0 and most preferred a pH value in the range of 7.5 to 8.5.

Preferably, $Mg^{2+}$ ions are present in the solution provided in step A) in a concentration between 1 mM and 100 mM, more preferably between 1 mM and 90 mM, more preferably between 2 mM and 90 mM, more preferably between 5 mM and 90 mM, more preferably between 10 mM and 90 mM, more preferably between 15 mM and 80 mM, more preferably between 20 mM and 80 mM and most preferably between 20 mM and 50 mM.

Preferably, the method for producing a galactosylated saccharide, a galactosylated glycopeptide, a galactosylated glycoprotein, a galactosylated protein, a galactosylated peptide, a galactosylated bioconjugate or a galactosylated small molecule comprises the following steps:
  A) providing a solution comprising
    (i) uridine monophosphate and D-galactose;
    (ii) polyphosphate, and adenosine triphosphate; and
    providing a set of enzymes comprising a glucose-1-phosphate uridylyltransferase, a galactokinase, a polyphosphate kinase, and a uridine monophosphate kinase;
  B) producing uridine 5'-diphospho-α-D-galactose from uridine monophosphate and D-galactose in the presence of the set of enzymes, polyphosphate, and adenosine triphosphate; and
  D) producing a galactosylated saccharide, galactosylated glycopeptide, galactosylated glycoprotein, galactosylated protein, galactosylated peptide, galactosylated bioconjugate or galactosylated small molecule from uridine 5'-diphospho-α-D-galactose and a saccharide, glycopeptide, glycoprotein, protein, peptide, bioconjugate or small molecule by forming an O-glycosidic bond between uridine 5'-diphospho-α-D-galactose and an available hydroxyl group of the saccharide, glycopeptide, glycoprotein, protein, peptide, bioconjugate or small molecule in the presence of a galactosyltransferase;
wherein at least one enzyme of the set of enzymes or the galactosyltransferase is immobilized on a solid support.

Preferably, the set of enzymes further comprises a pyrophosphatase. Preferably, the set of enzymes also comprises a 1-domain polyphosphate kinase and/or a 2-domain polyphosphate kinase. Preferably, the set of enzymes further comprises a pyrophosphatase and a 1-domain polyphosphate kinase and/or a 2-domain polyphosphate kinase. Preferably, each enzyme of the set of enzymes and the galactosyltransferase are co-immobilized on the solid support.

In one embodiment galactosylated milk saccharides are produced by the inventive methods described herein. Thus, in one embodiment the inventive method comprises the following steps:
  A) providing a solution comprising
    (i) uridine monophosphate and D-galactose;
    (ii) polyphosphate, and adenosine triphosphate; and
    providing a set of enzymes comprising a glucose-1-phosphate uridylyltransferase, a galactokinase, a polyphosphate kinase, and a uridine monophosphate kinase;
  B) producing uridine 5'-diphospho-α-D-galactose from uridine monophosphate and D-galactose in the presence of the set of enzymes, polyphosphate, and adenosine triphosphate; and
  D) producing a galactosylated milk saccharide from uridine 5'-diphospho-α-D-galactose and a milk saccharide by forming an O-glycosidic bond between uridine 5'-diphospho-α-D-galactose and an available hydroxyl group of the milk saccharide, in the presence of a galactosyltransferase.

Preferably, the galactosylated milk saccharide is a human milk oligosaccharide.

Preferably the galactosylated milk saccharides are selected from the group comprising Lacto-N-biose, Lacto-N-triose, 3'-Galactosyl lactose, Lacto-N-tetraose, Lacto-N-neotetraose, Lacto-N-neohexaose, Lacto-N-hexaose, Lacto-N-neooctaose, Lacto-N-neooctaose, para-Lacto-N-neohexaose, Lacto-N-neodecaose, 2'-fucosyllactose, 2',3-Difucosyllactose, Lacto-N-fucopentaose I, Lacto-N-fucopentaose II, Lacto-N-fuconeopentaose III, Lacto-N-difucohexaose I, F-p-Lacto-N-neohexaose, F-Lacto-N-neohexaose I, F-Lacto-N-neohexaose II, DF-Lacto-N-neohexaose, a1,2-Fucosylated lacto-N-neohexaose I, a1,2-Difucosylated lacto-N-neohexaose, α1,2-1,3Difucosylated lacto-N-neohexaose I, α1,2-1,3Difucosylated lacto-N-neohexaose II, α1,2-1,3Trifucosylated lacto-N-neohexaose I, α1,2-1,3Trifucosylated lacto-N-neohexaose II, α1,2-1,3-Tetrafucosylated lacto-N-neohexaose, 3-Fucosyllactose, Lacto-N-neofucopentaose I, Lacto-N-neofucopentaose V, Lacto-N-neofucopentaose II, Lacto-N-neodifucohexaose II, Lacto-N-difucohexaose II, α1,3-fucosylated lacto-N-triose II, Difucosylated para-Lacto-N-neohexaose, α2,3-Sialyllactose, α2,3-Sialyl-lacto-N-biose, α2,6-Sialyllactose, α2,6-Sialyllacto-N-tetraose, α2,6-Sialyllacto-N-neotetraose, α2,6-Sialyllacto-N-neohexaose (see FIG. 14).

In one embodiment galactosylated carbohydrate conjugate vaccines are produced by the inventive methods described herein. Thus, in one embodiment the inventive method comprises the following steps:
  A) providing a solution comprising
    (i) uridine monophosphate and D-galactose;
    (ii) polyphosphate, and adenosine triphosphate; and
    providing a set of enzymes comprising a glucose-1-phosphate uridylyltransferase, a galactokinase, a polyphosphate kinase, and a uridine monophosphate kinase;
  B) producing uridine 5'-diphospho-α-D-galactose from uridine monophosphate and D-galactose in the presence of the set of enzymes, polyphosphate, and adenosine triphosphate; and
  D) producing a galactosylated carbohydrate conjugate vaccine from uridine 5'-diphospho-α-D-galactose and a carbohydrate conjugate vaccine by forming an O-glycosidic bond between uridine 5'-diphospho-α-D-galactose and an available hydroxyl group of the carbohydrate antigen of the conjugate vaccine, in the presence of a galactosyltransferase.

Preferably, the carbohydrate conjugate vaccine is a $CRM_{197}$ conjugate selected from a pneumococcal saccharide, a H. influenzae type B saccharide, and a N. meningitidis serotype A, C, W or Y saccharide; a TT conjugate selected from a pneumococcal saccharide, a H. influenzae type B saccharide, and a N. meningitidis serotype A, C, W or Y saccharide; a DT conjugate selected from a pneumococcal saccharide, a H. influenzae type B saccharide, and a N. meningitidis serotype A, C, W or Y saccharide, a pneumococcal saccharide protein D conjugate, or a H. influenzae type B saccharide OMPC conjugate, wherein the pneumococcal saccharide is preferably selected from serotypes 1, 3, 4, 5, 6A, 6B, 7F, 9V, 14, 18C, 19A, 19F and 23F.

In one embodiment galactosylated antibody drug conjugates are produced by the inventive methods described herein. Thus, in one embodiment the inventive method comprises the following steps:
  A) providing a solution comprising
    (i) uridine monophosphate and D-galactose;
    (ii) polyphosphate, and adenosine triphosphate; and
    providing a set of enzymes comprising a glucose-1-phosphate uridylyltransferase, a galactokinase, a polyphosphate kinase, and a uridine monophosphate kinase;
  B) producing uridine 5'-diphospho-α-D-galactose from uridine monophosphate and D-galactose in the presence of the set of enzymes, polyphosphate, and adenosine triphosphate; and
  D) producing a galactosylated antibody drug conjugate from uridine 5'-diphospho-α-D-galactose and an antibody drug conjugate by forming an O-glycosidic bond between uridine 5'-diphospho-α-D-galactose and an available hydroxyl group of the antibody drug conjugate, in the presence of a galactosyltransferase.

Preferably, the antibody-drug conjugate comprises a monoclonal antibody and a cytotoxic agent.

In a preferred embodiment, galactosylated therapeutic proteins are produced by the inventive methods described herein (FIG. 13A+13B). Thus, in one embodiment the inventive method comprises the following steps:
  A) providing a solution comprising
    (i) uridine monophosphate and D-galactose;
    (ii) polyphosphate, and adenosine triphosphate; and
    providing a set of enzymes comprising a glucose-1-phosphate uridylyltransferase, a galactokinase, a polyphosphate kinase, and a uridine monophosphate kinase;
  B) producing uridine 5'-diphospho-α-D-galactose from uridine monophosphate and D-galactose in the presence of the set of enzymes, polyphosphate, and adenosine triphosphate; and
  D) producing a galactosylated therapeutic protein from uridine 5'-diphospho-α-D-galactose and a therapeutic protein by forming an O-glycosidic bond between uridine 5'-diphospho-α-D-galactose and an available hydroxyl group of a saccharide of therapeutic protein, in the presence of a galactosyltransferase.

Preferably, the therapeutic protein is a protein of the immunoglobulin superfamily. Preferably, the protein of the immunoglobulin superfamily and is an antibody. Preferably, the antibody is a monoclonal antibody including bispecific monoclonal antibodies and antibody-based drugs. Preferably, the antibody is not fully galactosylated. Preferably the therapeutic protein is selected from the group consisting of:

3F8, 8H9, Arcitumomab, Ascrinvacumab, Aselizumab, Atezolizumab, Atidortoxumab, Atinuma, Atorolimumab, Avelumab, Azintuxizumab vedotin, Bapineuzumab, Basiliximab, Bavituximab, BCD-100, Bectumomab, Begelomab, Belantamab mafodotin, Belimumab, Bemarituzuma, Benralizumab, Berlimatoxumab, Bermekimab, Bersanlimab, Bertilimumab, Besilesomab, Bevacizumab, Bezlotoxumab, Biciromab, Bimagrumab, Bimekizumab, Birtamimab, Bivatuzumab mertansine, Bleselumab, Blinatumomab, Blontuvetmab, Blosozumab, Bococizumab, Brazikumab, Brentuximab vedotin, Briakinumab, Brodalumab, Brolucizumab, Brontictuzumab, Burosumab, Cabiralizumab, Camidanlumab tesirine, Camrelizumab, Canakinumab, Cantuzumab mertansine, Cantuzumab ravtansine, Caplacizumab, Capromab pendetide, Carlumab, Carotuximab, Catumaxomab, cBR96-doxorubicin immunoconjugate, Cedelizumab, Cemiplimab, Cergutuzumab amunaleukin, Certolizumab pegol, Cetrelimab, Cetuximab, Cibisatamab, Cirmtuzumab, Citatuzumab bogatox, Cixutumumab, Clazakizumab, Clenoliximab, Clivatuzumab tetraxetan, Codrituzumab, Cofetuzumab pelidotin, Coltuximab ravtansine, Conatumumab, Concizumab, Cosfroviximab, CR6261, Crenezumab, Crizanlizumab, Crotedumab, Cusatuzumab, Dacetuzumab, Daclizumab, Dalotuzumab, Dapirolizumab pegol, Daratumumab, Dectrekumab, Demcizumab, Denintuzumab mafodotin, Denosumab, Depatuxizumab mafodotin, Derlotuximab biotin, Detumomab, Dezamizumab, Dinutuximab, Diridavumab, Domagrozumab, Dorlimomab aritox, Dostarlima, Drozitumab, DS-8201, Duligotuzumab, Dupilumab, Durvalumab, Dusigitumab, Duvortuxizumab, Ecromeximab, Eculizumab, Edobacomab, Edrecolomab, Efalizumab, Efungumab, Eldelumab, Elezanumab, Elgemtumab, Elotuzumab, Elsilimomab, Emactuzumab, Emapalumab, Emibetuzumab, Emicizumab, Enapotamab vedotin, Enavatuzumab, Enfortumab vedotin, Enlimomab pegol, Enoblituzumab, Enokizumab, Enoticumab, Ensituximab, Epitumomab cituxetan, Epratuzumab, Eptinezumab, Erenumab, Erlizumab, Ertumaxomab, Etaracizumab, Etigilimab, Etrolizumab, Evinacumab, Evolocumab, Exbivirumab, Fanolesomab, Faralimomab, Faricimab, Farletuzumab, Fasinumab, FBTA05, Felvizumab, Fezakinumab, Fibatuzumab, Ficlatuzumab, Figitumumab, Firivumab, Flanvotumab, Fletikumab, Flotetuzumab, Fontolizumab, Foralumab, Foravirumab, Fremanezumab, Fresolimumab, Frovocimab, Frunevetmab, Fulranumab, Futuximab, Galcanezumab, Galiximab, Gancotama, Ganitumab, Gantenerumab, Gatipotuzumab, Gavilimomab, Gedivumab, Gemtuzumab ozogamicin, Gevokizumab, Gilvetmab, Gimsilumab, Girentuximab, Glembatumumab vedotin, Golimumab, Gomiliximab, Gosuranemab, Guselkumab, Ianalumab, Ibalizumab, IBI308, Ibritumomab tiuxetan, Icrucumab, Idarucizumab, Ifabotuzumab, Igovomab, Iladatuzumab vedotin, IMAB362, Imalumab, Imaprelimab, Imciromab, Imgatuzumab, Inclacumab, Indatuximab ravtansine, Indusatumab vedotin, Inebilizumab, Infliximab, Inolimomab, Inotuzumab ozogamicin, Intetumumab, Iomab-B, Ipilimumab, Iratumumab, Isatuximab, Iscalimab, Istiratumab, Itolizumab, Ixekizumab, Keliximab, Labetuzumab, Lacnotuzumab, Ladiratuzumab vedotin, Lampalizumab, Lanadelumab, Landogrozumab, Laprituximab emtansine, Larcaviximab, Lebrikizumab, Lemalesomab, Lendalizumab, Lenvervimab, Lenzilumab, Lerdelimumab, Leronlimab, Lesofavumab, Letolizumab, Lexatumumab, Libivirumab, Lifastuzumab vedotin, Ligelizumab, Lilotomab satetraxetan, Lintuzumab, Lirilumab, Lodelcizumab, Lokivetmab, Loncastuximab tesirine, Lorvotuzumab mertansine, Losatuxizumab vedotin, Lucatumumab, Lulizumab pegol, Lumiliximab, Lumretuzumab, Lupartumab amadotin, Lutikizumab, Mapatumumab, Margetuximab, Marstacima, Maslimomab, Matuzumab, Mavrilimumab, Mepolizumab, Metelimumab, Milatuzumab, Minretumomab, Mirikizumab, Mirvetuximab soravtansine, Mitumomab, Modotuximab, Mogamulizumab, Monalizumab, Morolimumab, Mosunetuzumab, Motavizumab, Moxetumomab pasudotox, Muromonab-CD3, Nacolomab tafenatox, Namilumab, Naptumomab estafenatox, Naratuximab emtansine, Narnatumab, Natalizumab, Navicixizumab, Navivumab, Naxitamab, Nebacumab, Necitumumab, Nemolizumab, NEOD001, Nerelimomab, Nesvacumab, Netakimab, Nimotuzumab, Nirsevimab, Nivolumab, Nofetumomab merpentan, Obiltoxaximab, Obinutuzumab, Ocaratuzumab, Ocrelizumab, Odulimomab, Ofatumumab, Olaratumab, Oleclumab, Olendalizumab, Olokizumab, Omalizumab, Omburtamab, OMS721, Onartuzumab, Ontuxizumab, Onvatilimab, Opicinumab, Oportuzumab monatox, Oregovomab, Orticumab, Otelixizumab, Otilimab, Otlertuzumab, Oxelumab, Ozanezumab, Ozoralizumab, Pagibaximab, Palivizumab, Pamrevlumab, Panitumumab, Pankomab, Panobacumab, Parsatuzumab, Pascolizumab, Pasotuxizumab, Pateclizumab, Patritumab, PDR001, Pembrolizumab, Pemtumomab, Perakizumab, Pertuzumab, Pexelizumab, Pidilizumab, Pinatuzumab vedotin, Pintumomab, Placulumab, Plozalizumab, Pogalizumab, Polatuzumab vedotin, Ponezumab, Porgaviximab, Prasinezumab, Prezalizumab, Priliximab, Pritoxaximab, Pritumumab, PRO 140, Quilizumab, Racotumomab, Radretumab, Rafivirumab, Ralpancizumab, Ramucirumab, Ranevetmab, Ranibizumab, Ravagalimab, Ravulizumab, Raxibacumab, Refanezumab, Regavirumab, Relatlimab, Remtolumab, Reslizumab, Rilotumumab, Rinucumab, Risankizumab, Rituximab, Rivabazumab pegol, Rmab, Robatumumab, Roledumab, Romilkimab, Romosozumab, Rontalizumab, Rosmantuzumab, Rovalpituzumab tesirine, Rovelizumab, Rozanolixizumab, Ruplizumab, SA237, Sacituzumab govitecan, Samalizumab, Samrotamab vedotin, Sarilumab, Satralizumab, Satumomab pendetide, Secukinumab, Selicrelumab, Seribantumab, Setoxaximab, Setrusumab, Sevirumab, SGN-CD19A, SHP647, Sibrotuzumab, Sifalimumab, Siltuximab, Simtuzumab, Siplizumab, Sirtratumab vedotin, Sirukumab, Sofituzumab vedotin, Solanezumab, Solitomab, Sonepcizumab, Sontuzumab, Spartalizumab, Stamulumab, Sulesomab, Suptavumab, Sutimlimab, Suvizumab, Suvratoxumab, Tabalumab, Tacatuzumab tetraxetan, Tadocizumab, Talacotuzumab, Talizumab, Tamtuvetmab, Tanezumab, Taplitumomab paptox, Tarextumab, Tavolimab, Tefibazumab, Telimomab aritox, Telisotuzumab vedotin, Tenatumomab, Teneliximab, Teplizumab, Tepoditamab, Teprotumumab, Tesidolumab, Tetulomab, Tezepelumab, TGN1412, Tibulizumab, Tigatuzumab, Tildrakizumab, Timigutuzumab, Timolumab, Tiragotumab, Tislelizumab, Tisotumab vedotin, TNX-650, Tocilizumab, Tomuzotuximab, Toralizumab, Tosatoxumab, Tositumomab, Tovetumab, Tralokinumab, Trastuzumab, Trastuzumab emtansine, TRBS07, Tregalizumab, Tremelimumab, Trevogrumab, Tucotuzumab celmoleukin, Tuvirumab, Ublituximab, Ulocuplumab, Urelumab, Urtoxazumab, Ustekinumab, Utomilumab, Vadastuximab talirine, Vanalimab, Vandortuzumab vedotin, Vantictumab, Vanucizumab, Vapaliximab, Varisacumab, Varlilumab, Vatelizumab, Vedolizumab, Veltuzumab, Vepalimomab, Vesencumab, Visilizumab, Vobarilizumab, Volociximab, Vonlerolizumab, Vopratelimab, Vorsetuzumab mafodotin, Votumumab, Vunakizumab, Xentuzumab, XMAB-5574, Zalutumumab, Zanolimumab, Zatuximab, Zenocutuzumab, Ziralimumab, Zolbetuximab (=IMAB36, Claudiximab), and Zolimomab aritox.

Preferably, the set of enzymes further comprises a pyrophosphatase. Preferably, the set of enzymes also comprises a 1-domain polyphosphate kinase and/or a 2-domain polyphosphate kinase. Preferably, the set of enzymes further comprises a pyrophosphatase and a 1-domain polyphosphate kinase and/or a 2-domain polyphosphate kinase. Preferably, each enzyme of the set of enzymes and the galactosyltransferase are co-immobilized on the solid support.

In a preferred embodiment the inventive method comprises the following steps:
A) providing a solution comprising
  (i) uridine monophosphate and D-galactose;
  (ii) polyphosphate, and adenosine triphosphate; and
  providing a set of enzymes comprising a glucose-1-phosphate uridylyltransferase, a galactokinase, a polyphosphate kinase, and a uridine monophosphate kinase;
B) producing uridine 5'-diphospho-α-D-galactose from uridine monophosphate and D-galactose in the presence of the set of enzymes, polyphosphate, and adenosine triphosphate; and
D) producing a galactosylated antibody from uridine 5'-diphospho-α-D-galactose and an antibody by forming an O-glycosidic bond between uridine 5'-diphospho-α-D-galactose and an available hydroxyl group of a saccharide of the antibody, in the presence of a β-1,4-galactosyltransferase.

In a preferred embodiment the inventive method comprises the following steps:
A) providing a solution comprising
  (i) uridine monophosphate and D-galactose;
  (ii) polyphosphate, and adenosine triphosphate; and
  providing a set of enzymes comprising a glucose-1-phosphate uridylyltransferase, a galactokinase, a polyphosphate kinase, and a uridine monophosphate kinase;
B) producing uridine 5'-diphospho-α-D-galactose from uridine monophosphate and D-galactose in the presence of the set of enzymes, polyphosphate, and adenosine triphosphate; and
D) producing a galactosylated antibody from uridine 5'-diphospho-α-D-galactose and an antibody by forming an O-glycosidic bond between uridine 5'-diphospho-α-D-galactose and an available hydroxyl group of a saccharide of the antibody, in the presence of a β-1,4-galactosyltransferase; and
E) recycling the in-situ formed uridine diphosphate to form uridine triphosphate.

Due to the recycling of the by-product uridine diphosphate in the inventive galactosylation methods described herein, lower amounts of UMP are required in the solution provided in step A). Thus, in one embodiment, the molar ratio of UMP to D-galactose is between 0.0001 and 0.999, more preferably between 0.0005 and 0.995, more preferably between 0.001 and 0.995, more preferably between 0.002 and 0.99 and most preferably between 0.005 and 0.98. In one embodiment, the molar ratio of UMP to D-galactose is 0.05. In one embodiment, the molar ratio of UMP to D-galactose is 0.1. In one embodiment, the molar ratio of UMP to D-galactose is 0.2. In one embodiment, the molar ratio of UMP to D-galactose is 0.5.

In another embodiment, the molar ratio of UMP to D-galactose is between 1 and 10, more preferably between 1.2 and 8, more preferably between 1.5 and 7, more preferably between 1.6 and 6 and most preferably between 2 and 5. In one embodiment, the molar ratio of UMP to D-galactose is 1.5. In one embodiment, the molar ratio of UMP to D-galactose is 2. In one embodiment, the molar ratio of UMP to D-galactose is 5. In one embodiment, the molar ratio of UMP to D-galactose is 10.

DESCRIPTION OF THE FIGURES

FIG. 4A: shows the reaction time course of all measured compounds.

FIG. 4B: shows the HPAEC-UV chromatogram of the feed solution after 0 min reaction time.

FIG. 4C: shows the HPAEC-UV chromatogram of aliquots taken after a reaction time of 370 min.

FIG. 5A: shows the reaction time course of all measured compounds.

FIG. 5B: shows the HPAEC-UV chromatogram of the feed solution after 0 min reaction time.

FIG. 5C: shows the HPAEC-UV chromatogram of aliquots taken after a reaction time of 540 min.

FIG. 10: shows electropherogram (CGE-LIF analysis) of Rituximab (A) and galactosylated Rituximab (B) prepared by the inventive method.

FIG. 14: shows exemplary galactosylated human milk saccharides.

FIG. 17 shows educts, intermediates and product formed in the UDP-Gal scale-up experiment of Example I in direct comparison with small-scale run. (A) uridine; (B) UDP-Gal; (C) UMP; (D) UDP; (E) UTP; (F) ADP; (G) ATP; and (H) AMP.

FIG. 18 shows (A) chromatogram of reaction products containing LNnT and (B) MS/MS spectrum of the reaction product.

Figure 1:
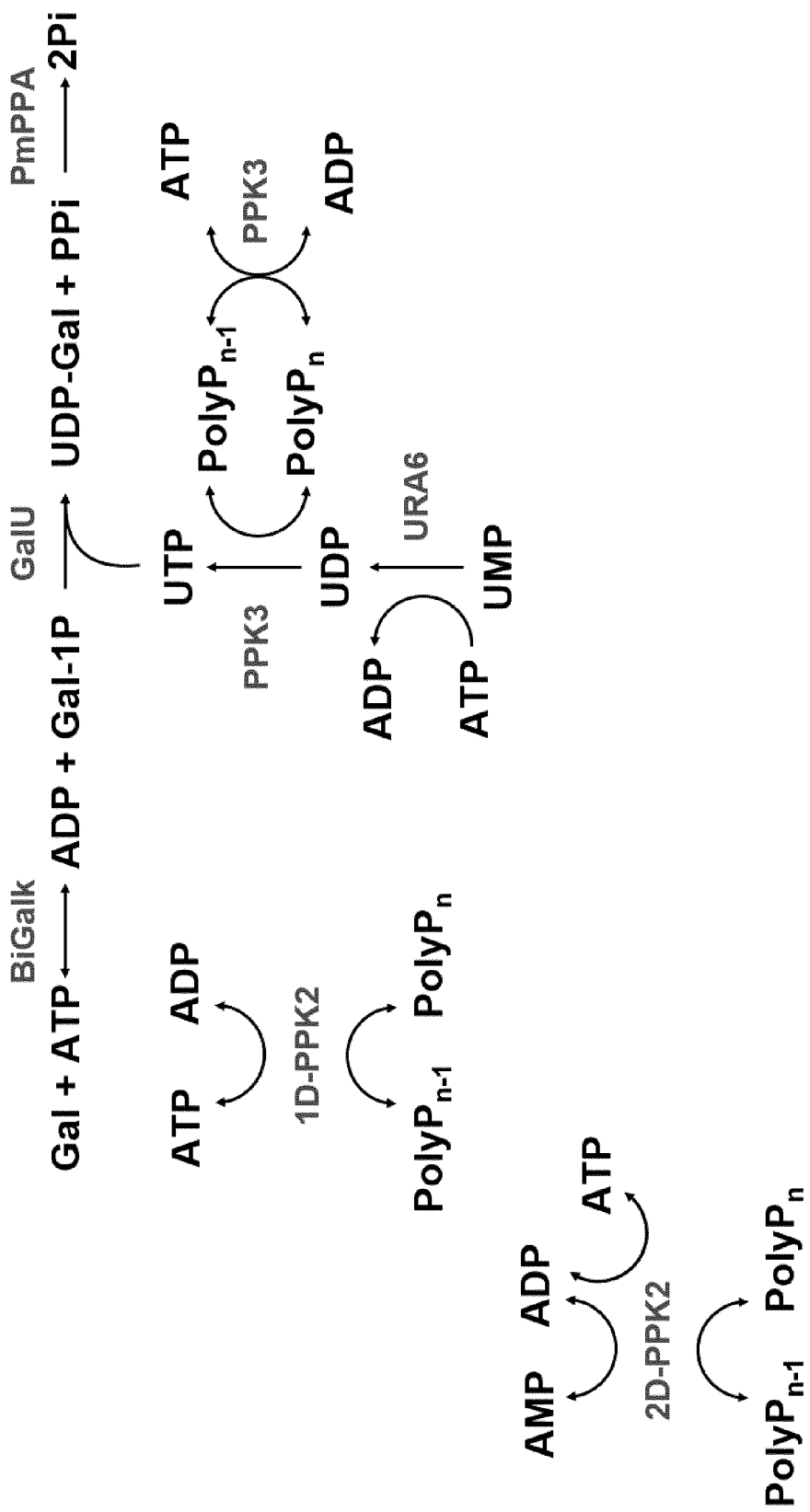
FIG. 1: shows the multi-enzyme cascade through which UDP-galactose is enzymatically synthesized from low-cost substrates galactose, polyphosphate and UMP. The reaction cascade consists of (a) the formation of galactose-1-phosphate (Gal-1P) from D-galactose and ATP, (b) the formation of uridine triphosphate (UTP) from UMP and polyphosphate, and (c) the reaction of galactose-1-phosphate with uridine triphosphate to UDP-galactose. Optionally an inorganic diphosphatase (PmPpa) can added to the reaction cascade in order to hydrolyze pyrophosphate $PP_i$ which inhibits the enzyme glucose 1-phosphate uridylyltransferase. The cascade can also be extended by adding a 1D-PPK2 to assist the conversion of ADP to ATP. Also, the cascade can be extended by adding a 2D-PPK2 in order to activate phosphorylation of AMP to ADP. Moreover, the cascade can be extended by adding a 1D-PPK2 and a 2DPPK2 in order to inhibit frequent hydrolysis of adenosine phosphates.
Figure 2:
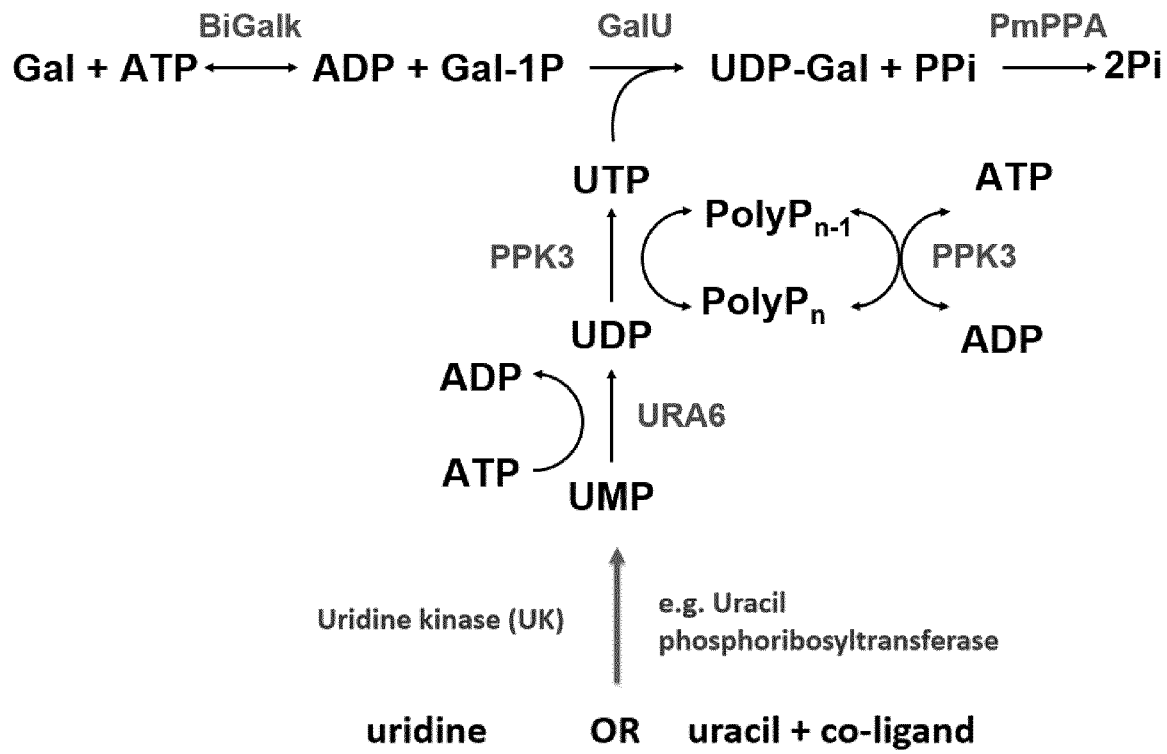
FIG. 2: shows an exemplary reaction scheme of the inventive method for producing UDP-galactose starting from uridine or uracil and 5-phospho-α-D-ribose 1-diphosphate. The formation of UMP from uridine is catalyzed by uridine kinase and the formation of UMP from uracil is catalyzed by uracil phosphoribosyltransferase.

The following examples are included to demonstrate preferred embodiments of the invention. It should be appreciated by those skilled in the art that the techniques disclosed in the examples, which follow represent techniques discovered by the inventor to function well in the practice of the invention, and thus can be considered to constitute preferred modes for its practice. However, those skilled in the art should, in light of the present disclosure, appreciate that many changes can be made in the specific embodiments, which are disclosed and still obtain a like or similar result without departing from the spirit and scope of the invention.

Further modifications and alternative embodiments of various aspects of the invention will be apparent to those skilled in the art in view of this description. Accordingly, this description is to be construed as illustrative only and is for the purpose of teaching those skilled in the art the general manner of carrying out the invention. It is to be understood that the forms of the invention shown and described herein are to be taken as examples of embodiments. Elements and materials may be substituted for those illustrated and described herein, parts and processes may be reversed, and certain features of the invention may be utilized independently, all as would be apparent to one skilled in the art after having the benefit of this description of the invention. Changes may be made in the elements described herein without departing from the spirit and scope of the invention as described in the following claims.

EXAMPLES

Abbreviations and Acronyms
ADP adenosine 5'-diphosphate
AMP adenosine 5'-monophosphate
ATP adenosine 5'-triphosphate
dH$_2$O deionized water
IPTG isopropyl β-D-thiogalactopyranoside
LGTB Lacto-N-neotetraose biosynthesis glycosyltransferase
UDP uridine 5'-diphosphate
UMP uridine 5'-monophosphate
UTP uridine 5'-triphosphate
GTP guanosine 5'-triphosphate
PolyP polyphosphate
PPi pyrophosphate
Pi phosphate
PPK2 polyphosphate kinase 2
PPK3 polyphosphate kinase 3
1D-PPK2 1-domain polyphosphate kinase 2
2D-PPK2 2-domain polyphosphate kinase 2
GalU glucose 1-phosphate uridylyltransferase
GalT UDP-galactosyltransferase
BiGalK galactokinase
GalK galactokinase
URA6 uridine monophosphate kinase
UPP uracil phosphoribosyltransferase
PmPpA *Pasteurella multocida* inorganic pyrophosphatase
Chemicals & Reagents Unless otherwise stated, all chemicals and reagents were acquired from Sigma-Aldrich, and were of the highest purity available. Solid supports were obtained from Resindion, ChiralVision, Röhm GmbH & Co. KG and micromod GmbH.

Example 1: Preparation of Enzymes

The genes encoding for the enzymes BiGalK, URA6, PPK3, GalU, 1D-PPK2, 2D-PPK2 and PmPpA were cloned into standard expression vectors as listed in Table 1.

TABLE 1

Enzymes used in this example

| Enzyme | Abbreviation | EC class | Origin | SEQ ID |
|---|---|---|---|---|
| glucose 1-phosphate uridylyltransferase | GalU | 2.7.7.9 | E. coli K-12 MG1655 | 4 |
| Galactokinase | BiGalk | 2.7.1.6 | Bifidobacterium infantis ATCC 15697 | 1 |
| Polyphosphate kinase 3 | PPK3 | 2.7.4.1 | Ruegeria pomeroyi | 3 |
| Uridine monophosphate kinase | URA6 | 2.7.4.14 | Arabidopsis thaliana | 2 |
| Inorganic diphosphatase | PmPpa | 3.6.1.1 | Pasteurella multocida Pm70 | 5 |
| 1-domain polyphosphate kinase 2 | 1D-PPk2 | 2.7.4.1 | Pseudomonas aeruginosa | 6 |
| 2-domain polyphosphate kinase 2 | 2D-PPK2 | 2.7.4.1 | Pseudomonas aeruginosa | 7 |

Transformation, Cultivation, Expression

For all gene expressions E. coli BL21 Gold (DE3) was used as a host organism unless stated otherwise.

Gene Expression: One-Enzyme, One-Cultivation (Expression Mode A).

Plasmids and Stock Cultures

Stock solutions of E. coli cultures carrying the plasmids (pET28a with kanamycin resistance) with the gene sequences of GalU, PPK3, URA6, PmPpa, 1D-PPK2 were available from earlier studies (see [1, 2]). The stock solutions contained 50% glycerol and were kept at −20° C.

Gene synthesis and cloning of the gene sequence of BiGalK into expression vector pET100/D-TOPO with an antibiotic resistance against ampicillin were carried out by a commercial supplier and according to earlier published literature [3].

The purchased plasmid was transferred into E. coli by transferring 1 µl of the plasmid stock solution into a culture E. coli BL21 Gold (DE3). The solution was than kept on ice for 1 h, followed by heat shocking the cells for 1 min at 42° C. Subsequently, 500 µL of LB media were added and the mix was incubated for 20 min at 37° C. followed by centrifuging the solution at 6000 g and 4° C. for 10 min. The supernatant was discarded and the cell pellet dissolved in 100 µl deionized $H_2O$ ($dH_2O$.) and spread on LB agar plates containing ampicillin. The agar plate was incubated at 37° C. Stock solutions of E. coli cells containing the plasmid were generated in 2 mL slant media.

Enzyme Expression

For heterologous gene expression, aliquots were removed from the stock solutions and spread on LB agar plates containing the according antibiotic. The plates were cultivated overnight at 37° C. Single cultures were used to inoculate precultures (containing 50 µg/mL kanamycin and 100 µg/mL ampicillin, respectively) in shaker flasks with baffles. Cultures were typically grown to an $OD_{600}$ of about 4.2. Main expression cultures containing 50 µg/mL kanamycin and 100 µg/mL ampicillin, respectively, were typically inoculated with 1% preculture and cultivated at 37° C. to an $OD_{600}$ of around 0.6-0.8. The temperature was then changed to 16-20° C. and the expression was induced with typically 0.4 mM IPTG. After, typically, 20 h. The cultures were harvested typically by 6000 xg for 30 min at 4° C. Media used were autoinduction (AI) media, LB and TB media. More details on the media used in the experiments are given in table 2 below.

TABLE 2

The content of growth media for E. coli is detailed. All media were autoclaved before use.

| Media | Content |
|---|---|
| Luria-Bertani (LB) | 10 g tryptone<br>5 g yeast extract<br>5 g NaCl<br>in 1 L $dH_2O$ |
| Terrific broth (TB) | 24 g yeast extract<br>12 g tryptone<br>5 g glycerol<br>89 mM Phosphate buffer (added after autoclaving)<br>in 1 L $dH_2O$ |
| Auto induction (AI) | See [5] |
| Slant | 20 g tryptone<br>10 g yeast extract<br>in 1 L $dH_2O$ with glycerol (50% v/v) |

Enzyme Purification

The plasmids pET28a and pET100/D-TOPO harbor a N-terminal His6-tag and the enzyme are, thus, purified with Ion metal affinity chromatography using the ÄKTA™ start system and HisTrap High-Performance or Fast-Flow columns (1 mL column volume) from GE Healthcare. For the purification of enzymes the cells were lysed by sonication in lysis buffer (50 mM HEPES (pH 7.5), 10 mM $Mg^{2+}$, 300 mM NaCl, 10 mM imidazole and 5% glycerol).

Imidazole (500 mM) was used as eluent in isocratic elutions (50 mM HEPES (pH 7.5), 10 mM $Mg^{2+}$, 300 mM NaCl, 500 mM imidazole and 5% glycerol). Standard conditions as recommended by the manufactures were used. After purification the enzyme concentrations were tested by BCA assays and evaluated by SDS-gels.

Gene Expression: All Enzymes, One Cultivation (Expression Mode B).

For the gene expression described in this section the LOBSTR E. coli expression strain (based on E. coli BL21 Gold (DE3)) from Kerafast Inc was used. Two gene sequences were cloned into one specific expression vector each. An E. coli strain was created carrying all three expression plasmids.

Cloning

The resistance markers and restriction sites for the used expression vectors are detailed in Table 3.

pACZDuet vector harboring the gene sequences for URA6 and PPK3 was bought from a commercial supplier. The gene sequences of GalU and PmPpA were cut by enzymatic digestion form isolated pET28a vectors and cloned into pCDFDuet expression vector. Standard protocols for enzymatic digestion, PCR and ligation were used for the cloning. GalK from pET100-D/TOPO and NahK from pET28a were cloned into expression vector pRSFDuet1. Empty expression vectors pCDFDuet and pRSFDuet1 were purchased from a commercial supplier.

The gene constructs were confirmed by gene sequencing by a commercial supplier.

TABLE 3

Gene sequences with restriction sites and expression vector for Expression Mode B.

| Template | Restriction sites | Destination vector (Res.) |
|---|---|---|
| GalK | NcoI, NotI | pRSFDuet1 (kanamycin) |
| GalU | NcoI, NotI | |
| PmPpA | NdeI, KpnI | pCDFDuet (spectinomycin) |
| URA6 | NcoI, NotI | |
| PPK3 | NdeI, KpnI | pACYCDuet (chloramphenicol) |

Transformation

All plasmids were transformed into LOBSTR E. coli cells by heat shock (as described in the "Gene expression: One enzyme, one cultivation" section) and then plated on LB agar plates containing all selection markers (chloramphenicol, spectinomycin, kanamycin). Thus, only those cells carrying all three vectors could grow on the agar plates.

Enzyme Expression

For the expression described here TB media was used containing the following concentrations of antibiotics (34 µg/mL chloramphenicol, 50 µg/mL spectinomycin, and 30 µg/mL kanamycin). The cells were precultured in 15 mL at 30° C. overnight, and main cultures of 200 mL were inoculated with 1% preculture and cultivated at 30° C. up to $OD_{600}$=0.8. The temperature was lowered to 16° C. and the expression was induced by adding 0.5 mM IPTG. After 20 h the cells were harvested by centrifuging at 6000 xg for 30 min at 4° C. Cell were lysed by sonication in lysis buffer (50 mM HEPES (pH 7.5), 10 mM $Mg^{2+}$, 300 mM NaCl, 10 mM imidazole and 5% glycerol).

Purification

Figure 3:
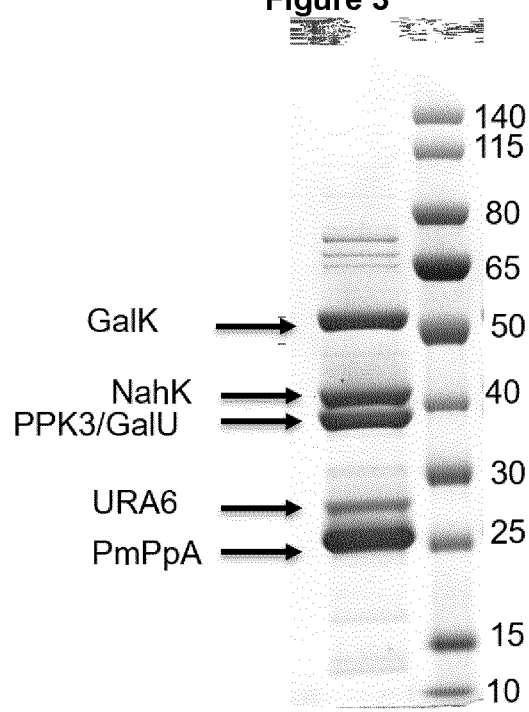
FIG. 3: shows the SDS-gel of the purified enzyme mix obtained by Expression mode B.

As described in the section "Gene expression: One enzyme, one cultivation". The enzyme concentrations were tested by the BCA assay and the purification was evaluated by a SDS-gel (see FIG. 3).

Measurements

High-performance anion exchange chromatography (HPAEC) with UV (260 nm) and pulsed amperometric detection (PAD) was utilized to measure concentrations of reactants. For analyte separation and quantification, a step gradient elution method was developed and validated. Chromatographic separation was performed at a system flow of 0.5 mL/min using a non-porous pellicular column CarboPac™ PA1 (250×2 mm). The HPAEC system (ICS5000) as well as all columns, components and software were purchased from Thermo Scientific (Waltham, USA).

Saccharides on antibodies were analyzed by PNGase F treatment and CGE-LIF analysis. Standard protocols were followed for the analysis.

Example 2: Homogeneous Preparation of UDP-Galactose—Experiments A, B and C

Purified enzymes from the Expression mode B were used for these experiments. The synthesis was carried out without 1D-PPK2 (Experiment A, see FIG. 1 for the pathway) and with 1D-PPK2 (Experiment B). The reaction volumes were 12 µL for Experiment A and 34 µL for Experiment B in HEPES (pH 7.5) buffered aqueous solutions. The reaction temperature was 30° C. The amount of purified enzymes used was 400 µg. Initial substrate, buffer, co-factor concentrations and the amount of enzymes used are detailed in Table 4.

Reaction aliquots for reaction time course measurements were quenched as follows. For Experiment A 2 µL of the reaction were aliquoted and diluted in 298 µL of 90° C. $dH_2O$, for Experiment B 5 µL were diluted in 315 µL of 90° C. $dH_2O$.

TABLE 4

Substrate, co-factor and buffer concentrations as well as amount of enzymes used in Experiment A and B.

| Compound | Experiment A | Experiment B | Experiment C |
|---|---|---|---|
| HEPES (mM) | 35 | 25 | 50 |
| $MgCl_2$ (mM) | 13 | 10 | |
| Purified enzyme mix (µg) | 400 | 400 | various |
| 1D-PPK2 (µg) | — | 5.2 | various |
| UMP (mM) | 3.5 | 2.8 | 2.5 |
| ATP (mM) | 1.8 | 1.3 | 2 |
| D-galactose (mM) | 3.5 | 2.8 | 2.5 |
| $PolyP_{25}$ (mM) | 5 | 3.75 | 6 |

The reaction time course of Experiment A is shown in FIG. 4A-C. After 370 min a UDP-galactose yield of 100% was achieved with respect to UMP and galactose. This result shows that this combination of enzymes can achieve full conversion of substrates to UDP-galactose. There is no apparent enzyme inhibition and no side reactions take place. AMP is detected showing that ADP is partly hydrolyzed.

The reaction time course of Experiment B is shown in FIG. 5A-C. After 540 min a UDP-galactose yield of 100% was achieved with respect to UMP and galactose. This result shows that this combination of enzymes can achieve full conversion of substrates to UDP-galactose. There is no apparent enzyme inhibition and no side reactions take place. However, no AMP was detected showing that in the presence of 1D-PPK2, ADP was converted back to ATP fast enough before detectable amounts of ADP were hydrolyzed to AMP (see Experiment A).

In Experiment C various enzyme concentrations were tested and the effect of this combination on the productivity was investigated. Enzymes were expressed as detailed in the section "Gene expression: One enzyme, one cultivation (Expression mode A)". The reaction volumes were 100 µl. Reactions were quenched after a reaction time of 14 h by taking an aliquot of 20 µl and diluting it in 480 µl $dH_2O$ (90° C.).

TABLE 5

Enzyme concentrations used for the 4 reactions in Experiment C.

| Enzyme | Series 1 (µg) | Series 2 (µg) | Series 3 (µg) | Series 4 (µg) |
|---|---|---|---|---|
| Galk | 300 | 300 | 300 | 300 |
| URA6 | 300 | 300 | 300 | 300 |
| PPK3 | 440 | 440 | 440 | 440 |
| GalU | 870 | 870 | 870 | 870 |
| PmPpA | 440 | 440 | 440 | 440 |
| 1D-PPK2 | 0 | 6.5 | 0 | 6.5 |
| 2D-PPK2 | 0 | 0 | 160 | 160 |

Figure 6:
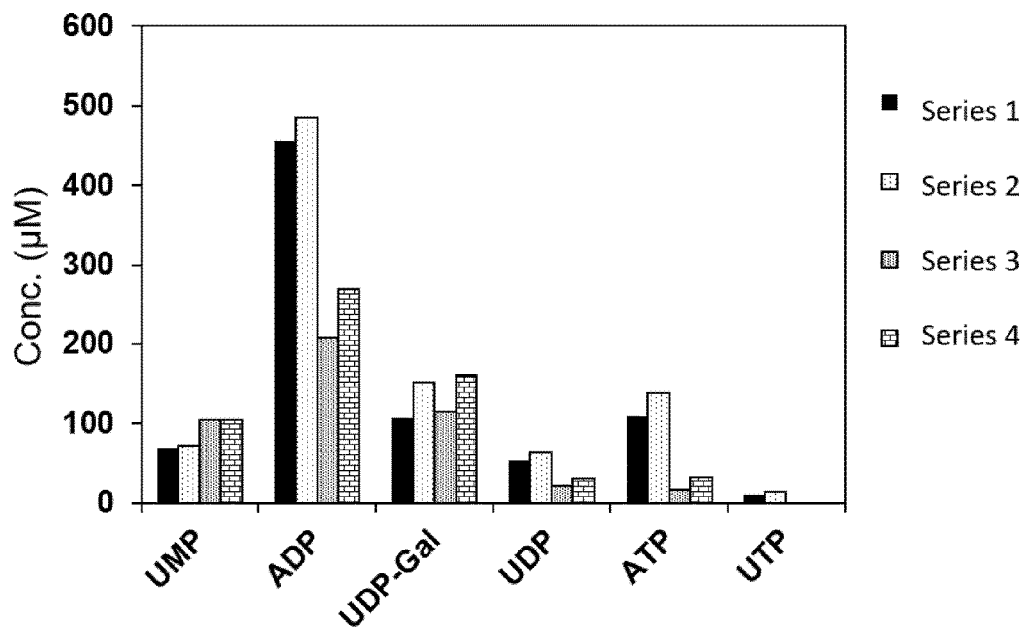
FIG. 6: shows substrate, metabolite and product concentrations after a reaction time of 14 h as measured by HPAEC-UV/PAD.

Results of Experiment C are depicted in FIG. 6. UDP-galactose was successfully formed in all reactions.

Example 3: Heterogeneous Preparation of UDP-Galactose—Experiment D

Figure 7:
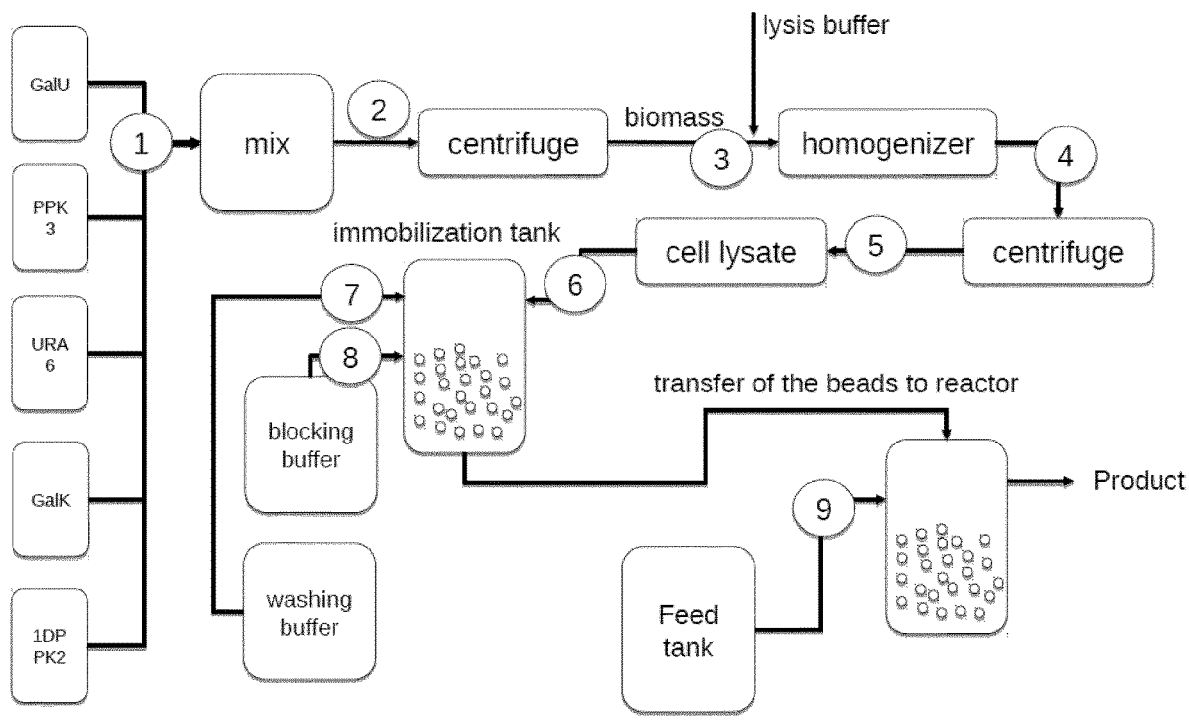
FIG. 7: shows a workflow scheme for the complete UDP-galactose cascade starting from mixing the biomasses containing the overexpressed enzymes to carrying out the synthesis reaction of UDP-galactose on a solid support. The workflow is also suitable for screening various solid supports for enzyme immobilization.

In Experiment D, a wide range of commercially available solid supports (Table 7) were screened for the co-immobilization of the enzymes used in the inventive UDP-galactose synthesis (see FIG. 1) and their effect on the synthesis of UDP-galactose was evaluated. As depicted in FIG. 7, the following protocol was used for the experiment: Biomasses from different cultivations were mixed together [see FIG. 7, step 1] and centrifuged 6000 xg for 30 min at 4° C. [step 2]. The composition of cultures used is detailed in Table 8. Cell pellets were resuspended in 60 mL buffer A [step 3] (see Table 6). Cells were lysed by sonication [step 4]. After sonication—the slurry was centrifuged 12 000 xg for 45 min at 4° C. [step 5] to remove cell debris, followed by filtration through 1.2 µm and 0.8 µm filters. After centrifugation, the supernatant was removed and kept on ice. A given mass of each immobilizer (see Table 8) was added to a 2 mL low-binding tube. After approximately 2 h of incubation with buffer A, the supernatant was removed. Afterwards, 0.5 mL of cell lysate were added to each tube and incubated overnight (~12 h) at 4° C. [step 6]. The beads were washed (3 times) with lysis buffer B [step 7] and blocking buffer (2 M glycine) was added followed by incubation for 24 h [step 8]. Afterwards, the blocking buffer was discarded and the beads were washed with buffer B (see Table 6) three times.

Figure 8:
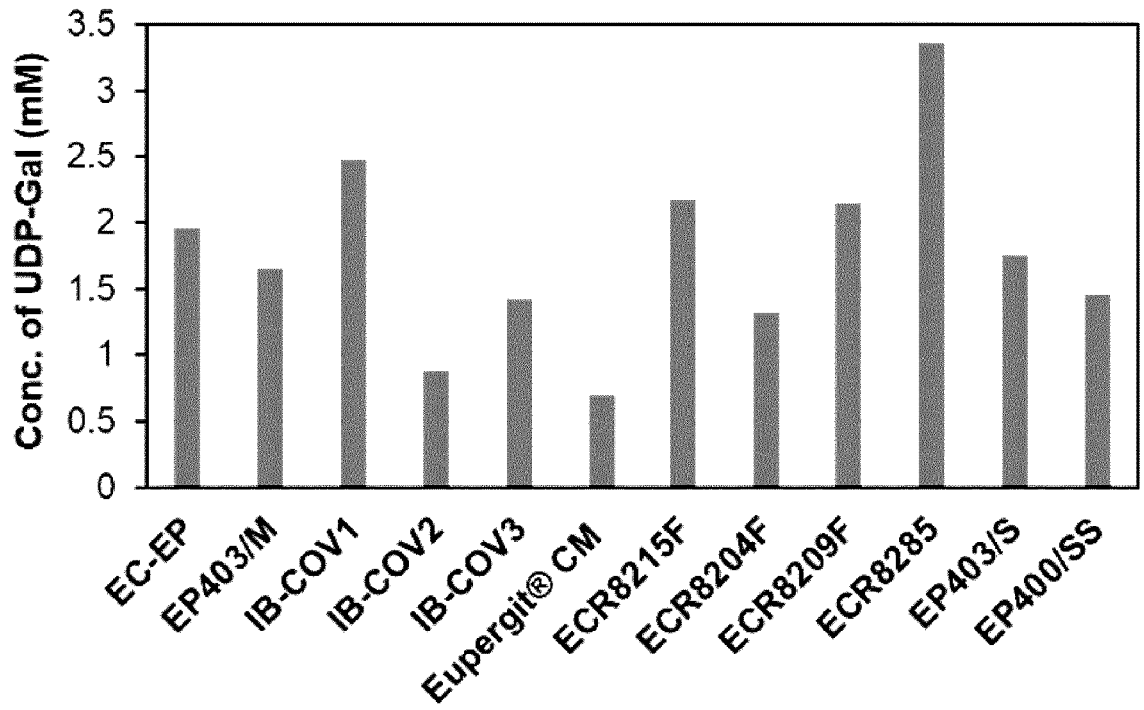
FIG. 8: Results of the solid support screening of the UDP-galactose synthesis. Concentrations were measured by HPAEC-UV.
Figure 9:
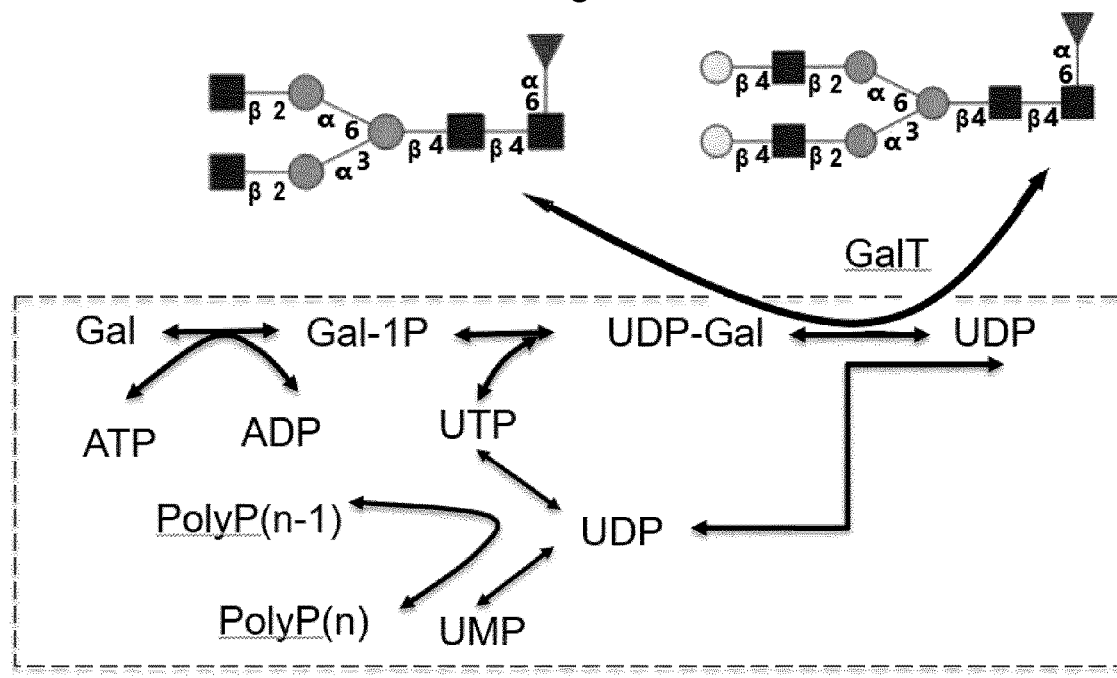
FIG. 9: shows the reaction scheme of the UDP-galactose cascade coupled to GalT to glycoengineer commercial antibodies such as Rituximab or Herceptin.

To test the multi-enzyme cascade on various enzyme loaded beads, 100 µL of the feed solution (see Table 9) containing substrates was transferred to each tube containing the beads. The reactions were carried out for around 20 h at 30° C. and under shaking (400 rpm). The UDP-galactose concentrations were then measured by HPAEC-UV/PAD. The results are depicted in FIG. 8. It is shown that the enzymes are active when co-immobilized on a wide variety of commercially available beads.

TABLE 6

Buffer compositions for Experiment D.

|  | Buffer A | Buffer B |
| --- | --- | --- |
| HEPES pH 7.5 (mM) | 75 | 200 |
| MgCl$_2$ (mM) | 20 | 20 |
| NaCl (mM) | 300 | 500 |
| Glycerol (% v/v) | 5 | 5 |
| Protease Inhibitor (Roche, EDTA-free "cOmplete ™") | 3 tablets | 3 tablets |

TABLE 7

Table of solid supports tested in Experiment D.

| Solid support | Mass used in Experiment D (mg) |
| --- | --- |
| EC-EP | 66 |
| EP403/M | 68 |
| IB-COV1 | 53 |
| IB-COV2 | 58 |
| IB-COV3 | 50 |
| Eupergit ® CM | 49 |
| ECR8215F | 52 |
| ECR8204F | 51 |
| ECR8209F | 52 |
| ECR8285 | 52 |
| EP403/S | 54 |
| EP400/SS | 62 |

TABLE 8

Overall volumes of cultures containing the overexpressed enzymes in E. coli used for Experiment D.

|  | AI media (mL) | LB media (mL) | TB media (mL) |
| --- | --- | --- | --- |
| GalK | 160 | 80 |  |
| PPK3 |  | 80 | 120 |
| URA6 |  |  | 120 |
| GalU |  | 200 |  |
| PmPpa |  | 40 |  |
| 1D-PPK2 |  |  | 80 |

TABLE 9

Concentrations of the feed solution used in Experiment D.

| Compound | Conc. (mM) |
| --- | --- |
| Galactose | 4.5 |
| UMP | 10.1 |
| ATP | 30 |
| PolyP$_{25}$ | 30 |
| MgCl$_2$ | 57 |
| HEPES (pH 7.5) | 100 |

Example 4: Galactosylation of Antibodies—Experiments F and G

In Experiment F and G the UDP-galactose cascade immobilized on solid support ECR8285 was coupled to a soluble UDP-galactosyltransferase (GalT) bought from Sigma-Aldrich to galactosylate the commercially available antibody Rituximab (purchased from Evidentic GmbH).

Pretests

In pretests (Experiment E) the glycoprofile of Rituximab was analyzed by PNGase F digest and CGE-LIF (see section "Measurements"). The results are depicted in FIG. 10A. It can be seen that only a small fraction of the glycans of the Fc-region of the antibody are fully galactosylated. To engineer the glycoprofile of the antibody, 100 µg Rituximab were incubated with bought UDP-Gal (purchased from Sigma-Aldrich, Order no. U4500) 25 milliunits of GalT (from Sigma-Aldrich, Order no. G5507) in 50 mM HEPES and 10 mM MnCl$_2$ overnight at 30° C. The results are depicted in FIG. 10B. The CGE-LIF analysis showed that after the reaction all detected glycans were galactosylated.

Coupling the cascade to GalT

One-Stage Coupling

Figure 11:
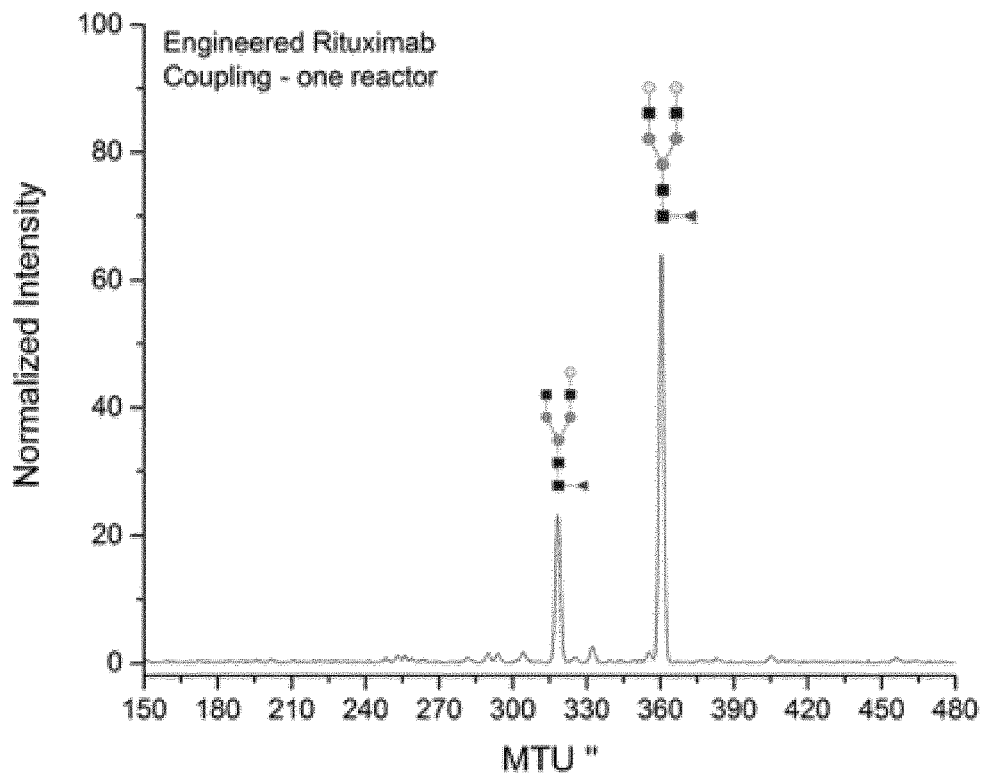
FIG. 11: shows electropherogram (CGE-LIF analysis) of Rituximab galactosylated in a one stage process of the inventive method.

In Experiment F feed solution (250 µL, see Table 9) was added to the ECR8285 beads (52 mg of solid support, weight measured before enzymes were immobilized on the bead) (from Experiment D) harboring the immobilized cascade. Immediately afterwards, 100 µg of Rituximab, GalT (25 milliunits) and 10 mM of MnCl$_2$ were added. After an incubation time of 24 h at 30° C. and shaking at 550 rpm, the supernatant of the reaction was then analyzed by PNGase F digest and CGE-LIF analysis (see section "Measurements"). The results are depicted in FIG. 11. It can be seen that all glycans were galactosylated. Most glycans are fully galactosylated while the smaller fraction exhibited only one galactose moiety on one of the two branches, indicating that achieving full galactosylation is a matter of incubation time and optimization of reactions conditions, i.e. reactant concentrations, respectively.

Figure 13A:
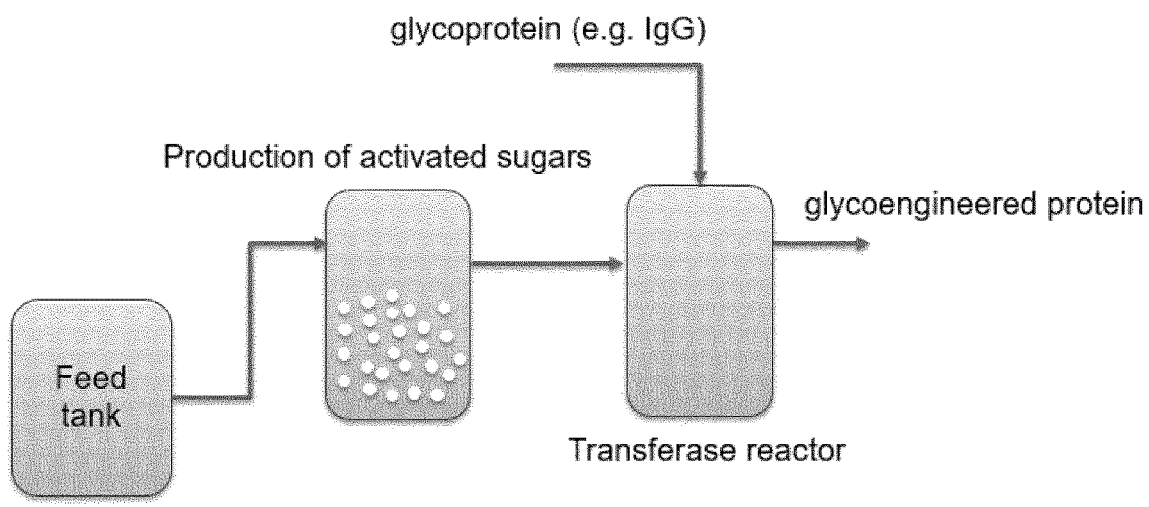
FIG. 13A: shows a process scheme for the inventive galactosylation of molecules, such as glycoproteins or antibodies, in a two reactor setup.
Figure 13B:
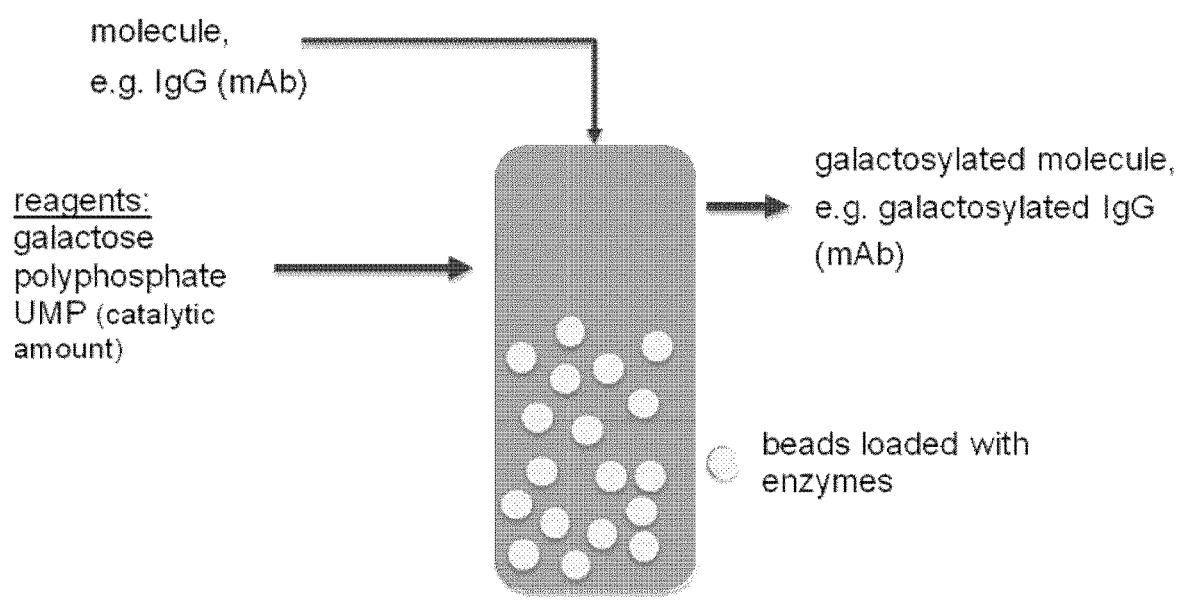
FIG. 13B: shows a process scheme for the inventive galactosylation of molecules, such as glycoproteins or antibodies, in a one-step one reactor setup. D-Galactose polyphosphate and UMP in catalytic amounts are added to a reactor containing a substrate to be galactosylated, beads loaded with the enzymes of the inventive UDP-Gal cascade and a galactosyltransferase. The galactosyltransferase may also be present in solution and not immobilized on the beads. Only catalytic amounts of UMP are required since the UDP-Gal consumed in the galactosylation reaction is continuously regenerated in the presence of the beads loaded with the enzymes of the inventive UDP-Gal cascade, galactose and polyphosphate.
Figure 15:
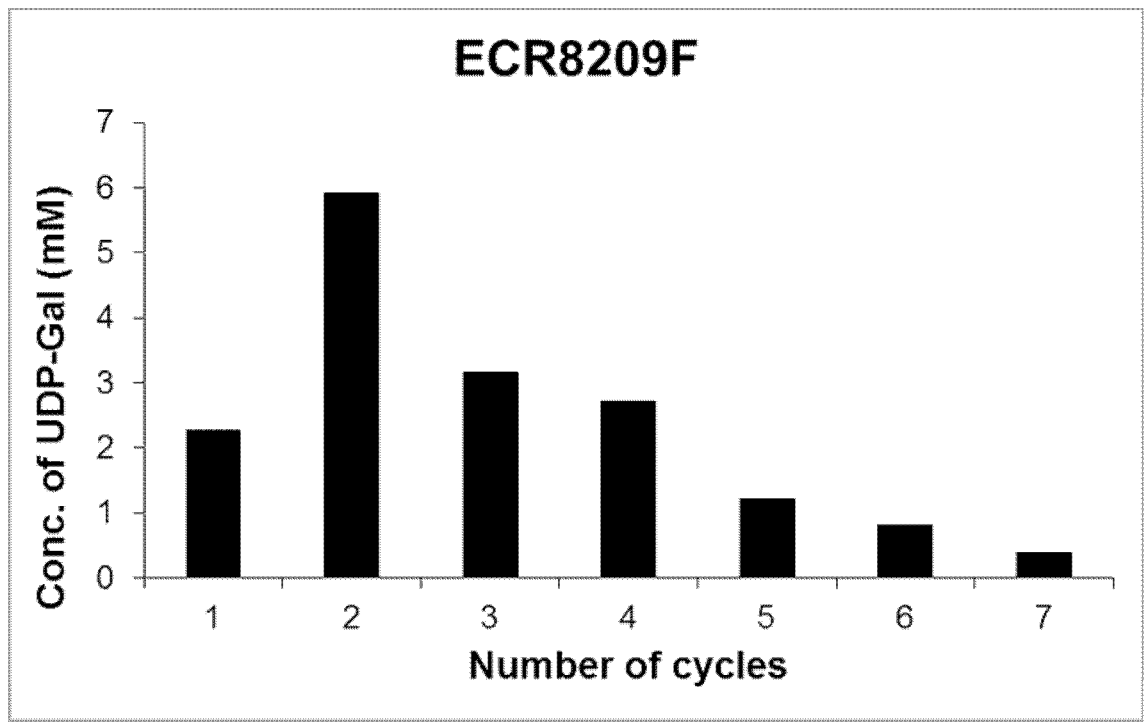
FIG. 15: shows exemplarily the reusability of UDP-Gal enzyme cascade co-immobilized on methacrylate beads functionalized with epoxy groups.

Two-Stage Coupling—See FIG. 13

In Experiment G, 100 μg Rituximab were galactosylated in a two stage process. In the first stage the enzyme cascade immobilized on ECR8285 was used to produce UDP-galactose. 52 mg of the beads (weight measured before enzymes were immobilized) were incubated with the feed solution (100 μL) at 30° C. for 24 h. In the second stage the supernatant was transferred to another reactor containing 100 μg Rituximab, 25 miliunits GalT and 10 mM MnCl$_2$.

Figure 12:
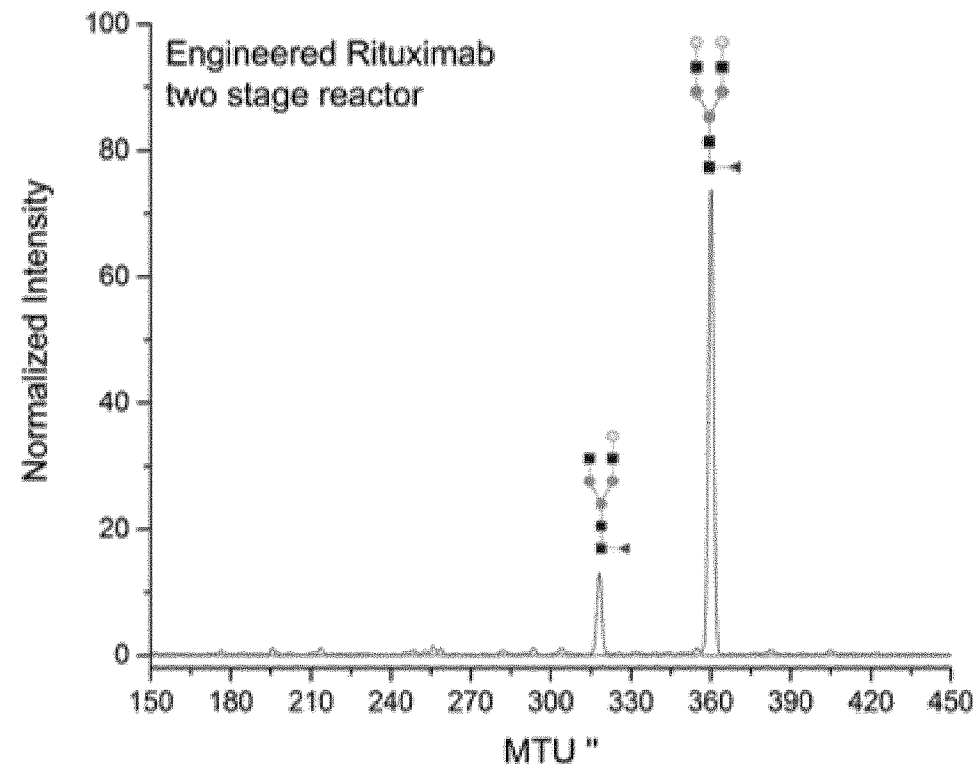
FIG. 12: shows electropherogram (CGE-LIF analysis) of Rituximab galactosylated in a two stage process of the inventive method.

The reactants were then incubated at 30° C. and 550 rpm for around 24 h. The supernatant of reaction was analyzed by PNGase F digest and CGE-LIF analysis (see section "Measurements") (see FIG. 12). Identical to Experiment F, all glycans were galactosylated with most glycans exhibiting galactose moieties on both branches, indicating that achieving full galactosylation is a matter of incubation time and optimization of reactions conditions, i.e. reactant concentrations, respectively.

Example 5: Synthesis of UDP-Gal Starting from Uridine—Experiments H, I, J and K

Production and Purification of the Enzymes

The list of the plasmid used in this study is shown in Table 10. LOBSTR E. coli competent cells (Kerafast, US) were used as the expression host. Cells were transformed based on heat-shock protocol. The fermentation carried out in TB media supplement with 1.5 mM MgSO$_4$ and corresponding antibiotics. The cells were cultivated at 37° C. until OD$_{600}$ of 0.8-1.0, afterwards, induction carried out with 0.4 mM IPTG, followed by 20-24 h cultivation at 16° C. All the chemicals used are from Carbosynth Ltd.

At the end of the cultivation, cells were harvested by centrifugation (7000×g, 20 minutes) and cell pellets were resuspended in lysis buffer (50 mM MOPS buffer, 300 mM NaCl, 10 mM MgCl$_2$, 10 mM imidazole and 5% glycerol at pH 7.4) and were disrupted by high-pressure homogenization (Maximator, Germany) (3 times passage at 800-1000 psi. Enzymes were purified using immobilized metal affinity chromatography (ÄKTAstart, GE Health care Life Sciences, Uppsala, Sweden) in combination with 1 mL or 5 mL HisTrap HP (GE Health care Life Sciences, Sweden) columns. The binding buffer contained 50 mM MOPS buffer, 300 mM NaCl, 10 mM MgCl$_2$, 10 mM imidazole and 5% glycerol at pH 7.4. And the elution buffer consisted of 50 mM MOPS buffer, 300 mM NaCl, 10 mM MgCl$_2$, 250 mM imidazole and 5% glycerol at pH 7.4.

To remove imidazole from the elution buffer and to concentrate the enzyme solution, buffer exchange was performed with Amicon® Ultra-15 Centrifugal Filter Unit—3 KDa MW cutoff (Merck, Germany). The exchange buffer contained 50 mM MOPS buffer, 300 mM NaCl, 10 mM MgCl$_2$, 5% glycerol at pH 7.4. Afterwards, the retentate solution (concentrated enzyme) was mixed 1:1 with glycerol to have the final enzyme solution in 50% glycerol. Enzymes were stored at −20° C.

TABLE 10

Enzymes used in this example.

| Gene | Abbr. | Enzyme | Uniprot. No. | Origin | Plasmid | SEQ ID No |
|---|---|---|---|---|---|---|
| galK | GALK | Galactokinase | B3DTF0 | Bifidobacterium longum | pET100/D-TOPO | 8 |
| galu | GALU | UTP-glucose-1-phosphate uridylyltransferase | P0AEP3 | Escherichia coli (strain K12) | pET-28a(+) | 4 |
| ppa | PmPpA | Inorganic diphosphatase | P57918 | Pasteurella multocida | pET-28a(+) | 5 |
| udk | UDK | uridine/cytidine kinase | P0A8F4 | Escherichia coli (strain K12) | pET-28a(+) | 9 |
| UMK3 | URA6 | UMP/CMP kinase | O04905 | Arabidopsis thaliana | pACYCDuet | 2 |
| SPO1727 | PPK3 | NDP kinase/polyP$_n$ kinase | Q5LSN8 | Ruegeria pomeroyi | pACYCDuet | 3 |

Experiment H—Synthesis of UDP-Gal Starting from Uridine Using Purified Enzymes

Figure 16:
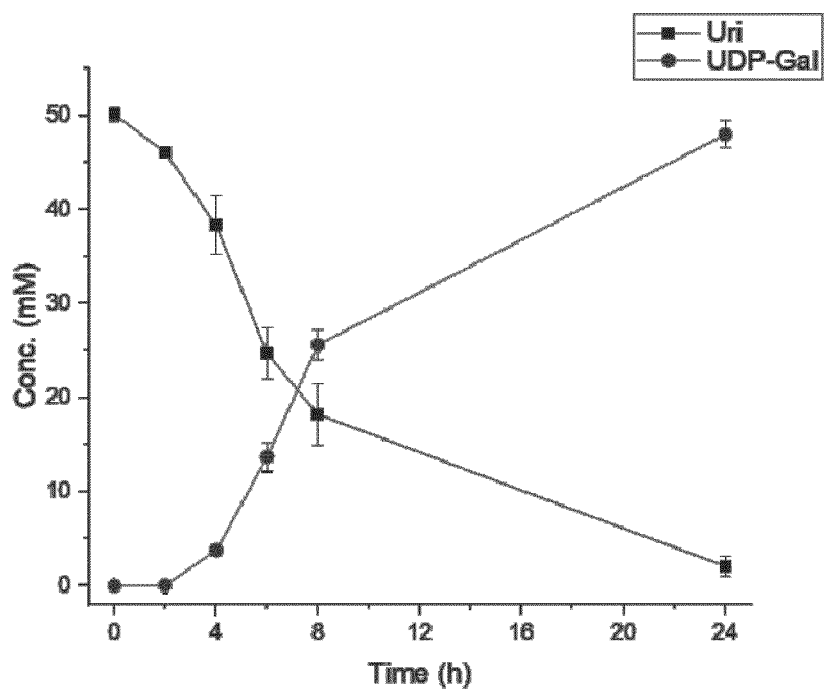
FIG. 16 shows intermediates and product formed in the UDP-Gal cascade of Experiment H. (A) UDP-Gal and uridine; (B) UMP, UDP and UTP; (C) ADP, AMP and ATP. The experiments were carried out in triplicate; error bars represent standard deviation.

The reactions contained 150 mM Tris-HCl (pH 8.5), 75 mM MgCl$_2$, 52 mM uridine, 54 mM Gal, 0.6 mM ATP, 20 mM PolyP$_n$, 0.07 μg/μL UDK, 0.12 μg/μL URA6/PPK3, 0.17 μg/μL GALK, 0.12 μg/μL GALU, 0.06 μg/μL PmPpa in the total volume of 250 μL. The successful production of UDP-Gal and concentration of intermediates are shown in FIG. 16. Yields are approaching 100% after 24 hours.

Experiment I—Large Scale Production of UDP-Gal from Uridine and Gal Using Cell Lysate For the preparation of cell-lysate the following biomasses were mixed: UDK, 3.46 g; URA6/PPK3, 5.20 g; GALK, 5.54 g; GALU, 5.70 g; PmPpA, 1.7 g in 120 mL of 50 mM HEPES buffer (pH 8.1), 400 mM NaCl, and 5% glycerol. The mixture was passed three times through a high-pressure homogenizer. The cell-free extract was centrifuged at 10,000×g for 45 min. Afterwards, small scale (200 μL) preliminary experiments were carried out to find a suitable lysate amount for the UDP-Gal synthesis. It was found out 10% of v/v of cell lysate is sufficient to perform the synthesis. These findings were directly used for the 1 liter scale synthesis which correlate to 5000× scaling factor.

To carry out the 1 liter experiment, a spinner flask equipped with a propeller type impeller was chosen to mimic the condition of a stirred tank reactor. The synthesis conditions were as follows: 150 mM Tris-HCl (pH 8.5), 58 mM uridine, 55 mM Gal, 6.2 mM ATP, 20 mM PolyP$_n$, and 75 mM MgCl$_2$. The reaction was carried out at 37° C. and 60 rpm. To understand the effect of the scale-up on the performance of the cascade, a parallel 200 μL experiment was carried out. The time courses of cascade intermediates are shown in FIG. 17.

Experiment J—One-Pot Production of Lacto-N-Neotetraose (LNnT)

In these experiments, HMOS are synthesized using recombinant Leloir glycosyltransferases and nucleotide sugar modules (UDP-Gal and UDP-GlcNAc). The nucleotide sugar is synthesized first and subsequently, the reaction mixture is combined with the glycosyltransferases and substrates to produce the target HMO.

UDP-Gal was produced based on the condition described in Table 11. All the reactions were carried out with an incubation time of around 24 hours, 550 rpm shaking at 37° C. Afterwards, 75 µL of the reaction module containing the product UDP-Gal was transferred to a new vial containing 0.2 µg/µL LGTB (Lacto-N-neotetraose biosynthesis glycosyltransferase, from *Neisseria meningitidis* serogroup B (strain MC58), expressed in *E. coli* BL21), 20 units of alkaline phosphatase (AP), 150 µL of Lacto-N-triose (LNT II), and 156 mM of MES buffer (pH 5.5). The chromatogram of the reaction product and MS/MS results, after overnight incubation, are shown in the FIG. 18.

TABLE 11

Reaction conditions for production of UDP-Gal.

| Reaction Mixture | Concentration |
|---|---|
| UDK | 0.06 µg/µL |
| URA6/PPK3 | 0.1 µg/µL |
| GALK | 0.16 µg/µL |
| GALU | 0.12 µg/µL |
| PPA | 0.06 µg/µL |
| Gal | 52 mM |
| Uridine | 50 mM |
| ATP | 2.5 mM |
| PolyP$_{25}$ | 20 mM |
| Tris-HCl (8.5) | 150 mM |
| MgCl$_2$ | 75 mM |
| Total Volume | 20 mL |

Experiment K—One-Pot Production of Para-Lacto-N-Neohexaose (Para-LNnH)

Figure 19:
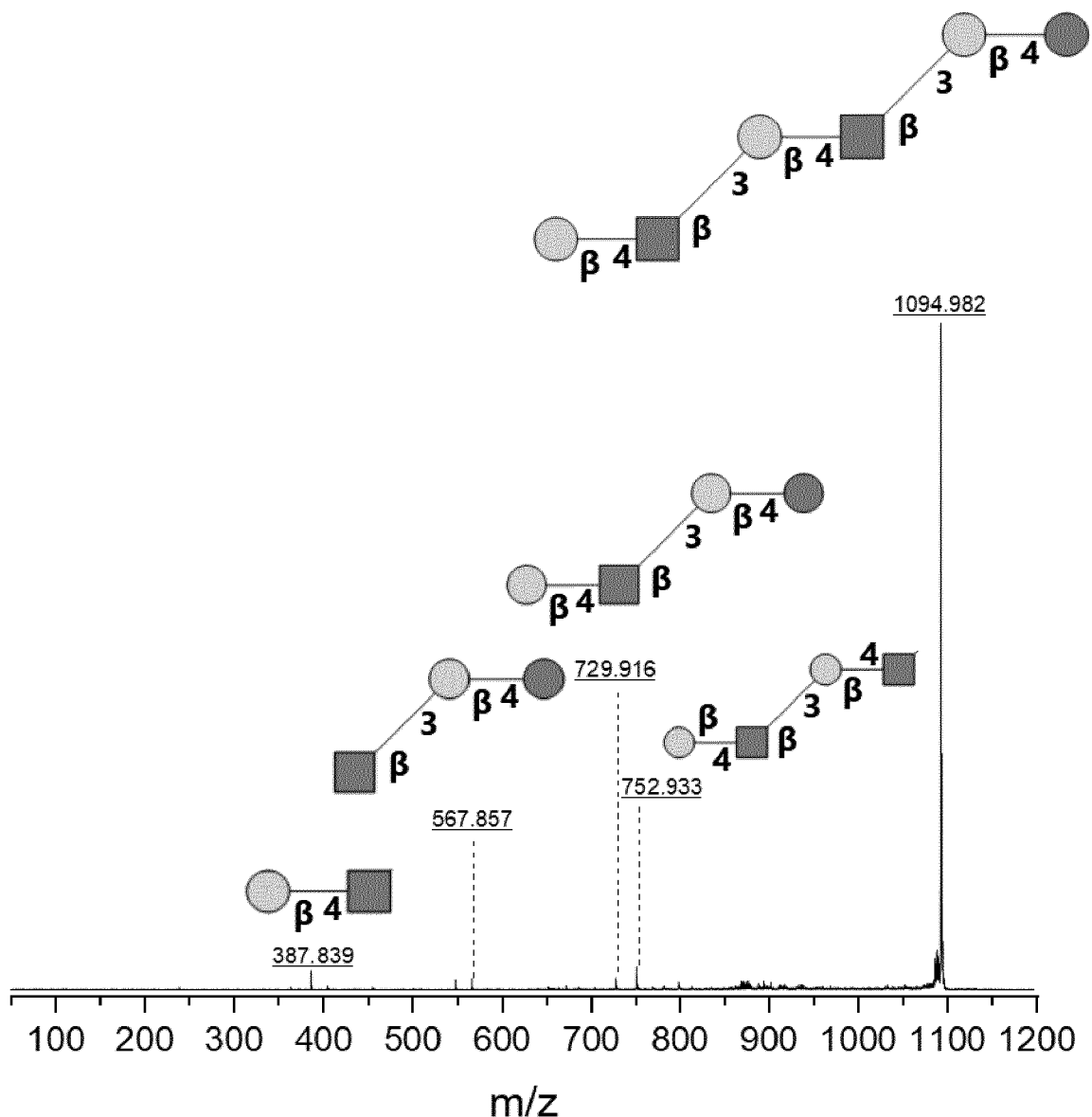
FIG. 19 shows the MS/MS spectrum of the reaction product of the formation of para-Lacto-N-neohexaose (para-LNnH) (experiment K).

50 µL of a para-Lacto-N-neopentaose containing solution was mixed with 40 µL of the UDP-Gal reaction mixture as listed in Table 11 containing UDP-Gal as a reaction product, and 20 units of AP and 0.2 µg/µL of LGTB in MES buffer (240 mM-pH 6.5) in a total volume of 210 µL. The MS/MS spectrum of the reaction product is shown in FIG. 19.

REFERENCES

1. Mahour, R., et al., *Establishment of a five-enzyme cell-free cascade for the synthesis of uridine diphosphate N-acetylglucosamine.* Journal of Biotechnology, 2018. 283: p. 120-129.
2. Rexer, T. F. T., et al., *One pot synthesis of GDP-mannose by a multi-enzyme cascade for enzymatic assembly of lipid-linked oligosaccharides.* Biotechnology and Bioengineering, 2018. 115(1): p. 192-205.
3. Li, L., et al., *A highly efficient galactokinase from Bifidobacterium infantis with broad substrate specificity.* Carbohydrate Research, 2012. 355: p. 35-39.
4. Warnock, D., et al., *In vitro galactosylation of human IgG at 1 kg scale using recombinant galactosyltransferase.* Biotechnology and Bioengineering, 2005. 92(7): p. 831-842.
5. Li, Z., et al., *Simple defined autoinduction medium for high-level recombinant protein production using T7-based Escherichia coli expression systems.* Applied Microbiology and Biotechnology, 2011. 91(4): p. 1203.

The invention claimed is:

1. A method for producing uridine 5'-diphospho-a-D-galactose comprising the following steps:

A) providing a solution comprising
   (i) uridine monophosphate and D-galactose represented by the following formulae

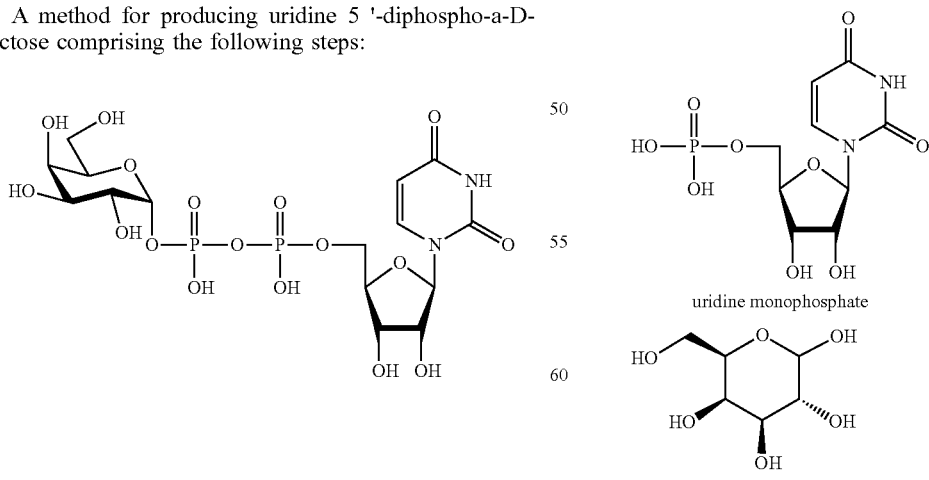

uridine monophosphate

D-galactose (ii) polyphosphate, and adenosine triphosphate; and
providing a set of enzymes comprising a glucose-1-phosphate uridylyltransferase, a galactokinase, a polyphosphate kinase, and a uridine monophosphate kinase;

B) producing uridine 5'-diphospho-α-D-galactose from uridine monophosphate and D-galactose in the presence of the set of enzymes, polyphosphate, and adenosine triphosphate.

2. The method according to claim 1, wherein the set of enzymes further comprises a pyrophosphatase.

3. The method according to claim 1, wherein the set of enzymes further comprises a one-domain polyphosphate kinase 2.

4. The method according to claim 1, wherein the set of enzymes further comprises a two-domain polyphosphate kinase 2.

5. The method according to claim 1, wherein at least one enzyme of the set of enzymes is immobilized on a solid support.

6. The method according to claim 1, wherein the set of enzymes is co-immobilized on a solid support.

7. The method according to claim 6, wherein the set of enzymes is directly co-immobilized on a solid support from fermentation broth, crude cell lysate, purified cell lysate or cell homogenate.

8. The method according to claim 1, wherein the concentration of uridine monophosphate and D-galactose in the solution provided in A) is in the range of 0.2 mM to 15,000 mM.

9. The method according to claim 1, wherein the polyphosphate is a long-chain polyphosphate having at least 25 phosphate residues.

10. The method according to claim 1, wherein the uridine 5'-diphospho-α-D-galactose is produced in a single reaction mixture.

11. The method according to claim 1, wherein the uridine monophosphate in A) is obtained from uridine, adenosine triphosphate and a uridine kinase; or from uracil, 5-phospho-α-D-ribose 1-diphosphate and a uracil phosphoribosyltransferase; or from orotic acid, 5-phospho-α-D-ribose 1-diphosphate, an orotate phosphoribosyltransferase and a UMP transferase.

12. The method according to claim 1, further comprising producing a galactosylated saccharide, galactosylated glycopeptide, galactosylated glycoprotein galactosylated protein, galactosylated peptide, galactosylated bioconjugate or galactosylated small molecule from uridine 5'-diphospho-α-D-galactose and a saccharide, glycopeptide, glycoprotein, protein, peptide, bioconjugate or small molecule by forming an O-glycosidic bond between uridine 5'-diphospho-α-D-galactose and an available hydroxyl group of the saccharide, glycopeptide, glycoprotein, protein, peptide, bioconjugate or small molecule in the presence of a galactosyltransferase.

13. The method according to claim 12, wherein the saccharide, glycopeptide, glycoprotein, protein, peptide, bioconjugate or small molecule is an antibody or a monoclonal antibody; or a human milk oligosaccharide or a bioconjugate.

14. The method according to claim 12, further comprising recycling of uridine diphosphate formed from the producing a GlcNAcylated saccharide, a GlcNAcylated glycopeptide, a GlcNAcylated glycoprotein, a GlcNAcylated protein, a GlcNAcylated peptide, a GlcNAcylated bioconjugate or a GlcNAcylated small molecule from uridine 5'-diphospho-N-acetylglucosamine and a saccharide, glycopeptide, glycoprotein, protein, peptide, bioconjugate or small molecule by forming an O-glycosidic bond between uridine 5'-diphospho-N-acetylglucosamine and an available hydroxyl group of the saccharide, glycopeptide, glycoprotein, protein, peptide, bioconjugate or small molecule in the presence of an N-acetylglucosaminyltransferase to obtain uridine triphosphate.

15. The method according to claim 12, wherein the saccharide, glycopeptide, glycoprotein, protein, peptide, bioconjugate or small molecule is a carbohydrate conjugate vaccine or an antibody drug conjugate.

\* \* \* \* \*